(12) United States Patent
Kamm et al.

(10) Patent No.: US 9,121,847 B2
(45) Date of Patent: Sep. 1, 2015

(54) THREE-DIMENSIONAL MICROFLUIDIC PLATFORMS AND METHODS OF USE THEREOF

(75) Inventors: Roger D. Kamm, Cambridge, MA (US); Seok Chung, Somerville, MA (US); Vernella V. Vickerman-Kelley, Cambridge, MA (US)

(73) Assignee: Massachussetts Institute of Technology, Cambridge, MA (US)

( * ) Notice: Subject to any disclaimer, the term of this patent is extended or adjusted under 35 U.S.C. 154(b) by 506 days.

(21) Appl. No.: 12/936,954

(22) PCT Filed: Apr. 3, 2009

(86) PCT No.: PCT/US2009/039434
§ 371 (c)(1),
(2), (4) Date: Jan. 3, 2011

(87) PCT Pub. No.: WO2009/126524
PCT Pub. Date: Oct. 15, 2009

(65) Prior Publication Data
US 2011/0159522 A1 Jun. 30, 2011

Related U.S. Application Data

(60) Provisional application No. 61/123,344, filed on Apr. 8, 2008.

(51) Int. Cl.
*C12M 1/34* (2006.01)
*G01N 33/50* (2006.01)
*C12Q 1/02* (2006.01)
*B01L 3/00* (2006.01)

(52) U.S. Cl.
CPC .............. *G01N 33/5029* (2013.01); *C12Q 1/02* (2013.01); *G01N 33/5082* (2013.01); *B01L 3/5027* (2013.01); *G01N 2333/515* (2013.01)

(58) Field of Classification Search
None
See application file for complete search history.

(56) References Cited

U.S. PATENT DOCUMENTS

| 6,197,575 | B1 | 3/2001 | Griffith et al. |
|---|---|---|---|
| 2003/0049839 | A1 | 3/2003 | Romero-Ortega et al. |
| 2003/0175824 | A1 | 9/2003 | Pishko et al. |
| 2004/0059299 | A1 | 3/2004 | Moller |
| 2004/0084811 | A1 | 5/2004 | Beebe et al. |
| 2004/0106192 | A1 | 6/2004 | Jeon et al. |
| 2004/0142411 | A1 | 7/2004 | Kirk et al. |
| 2004/0178071 | A1 | 9/2004 | Harrison et al. |
| 2004/0259177 | A1 | 12/2004 | Lowery et al. |
| 2005/0008675 | A1 | 1/2005 | Bhatia et al. |
| 2005/0079985 | A1 | 4/2005 | Shasho |
| 2005/0169962 | A1 | 8/2005 | Bhatia et al. |
| 2005/0260745 | A1 | 11/2005 | Domansky et al. |
| 2006/0136182 | A1* | 6/2006 | Vacanti et al. ............... 703/11 |
| 2006/0154361 | A1* | 7/2006 | Wikswo et al. ............ 435/289.1 |
| 2006/0263241 | A1 | 11/2006 | Beebe et al. |
| 2007/0008609 | A1 | 1/2007 | Ohtsuki et al. |
| 2007/0015274 | A1 | 1/2007 | Shuler et al. |
| 2007/0099294 | A1 | 5/2007 | Yang et al. |
| 2007/0122896 | A1 | 5/2007 | Shuler et al. |
| 2007/0128715 | A1 | 6/2007 | Vukasinovic et al. |
| 2007/0178582 | A1 | 8/2007 | Koser |
| 2007/0224172 | A1* | 9/2007 | Hendriks et al. ............. 424/93.7 |
| 2011/0186165 | A1* | 8/2011 | Borenstein et al. ........... 137/833 |

FOREIGN PATENT DOCUMENTS

| KR | 2007033685 | 3/2007 |
|---|---|---|
| WO | WO-03/091730 | 11/2003 |
| WO | WO-2004/038367 | 5/2004 |
| WO | WO-2004/038368 | 5/2004 |
| WO | WO-2004/059299 | 7/2004 |
| WO | WO-2004/083867 | 9/2004 |
| WO | WO-2005/079985 | 9/2005 |
| WO | WO-2006/052223 | 5/2006 |
| WO | WO-2007/008609 | 1/2007 |
| WO | WO-2007/139511 | 12/2007 |
| WO | WO-2008-040015 A2 | 4/2008 |

OTHER PUBLICATIONS

International Search Report and Written Opinion from PCT/US2009/039434 dated Feb. 2, 2010.
Editor of Annals of Biomedical Engineering, "March Editorial," Annals of Biomedical Engineering, 38(3):557 (Mar. 2010).
PowerPoint Presentation by Roger Kamm at the 5th International Biofluids Symposium at CalTech on Mar. 28, 2008, entitled "Microfluidic platforms for studies of angiogenesis, cell migration, and cell-cell interactions," pp. 1-31.
Supplemental European Search Report dated Aug. 13, 2013, in EP 09731255.7.
Office Action dated Mar. 20, 2014, in EP 09731255.7.
Chung et al., "Cell migration into scaffolds under co-culture conditions in a microfluidic platform," Lab Chip, 9:269-275 (2009).
Chung et al., "Microfluidic Platforms for Studies of Angiogenesis, Cell Migration, and Cell-Cell Interactions," Annals of Biomedical Engineering, 38(3):1164-1177 (2010).
Shamloo et al., "Endothelial cell polarization and chemotaxis in a microfluidic device," Lab Chip, 8:1291-1299 (2008).
Supplementary European Search Report dated Aug. 13, 2013, from EP 09 73 1255.
Bayless et al., "RGD-Dependent Vacuolation and Lumen Formation Observed during Endothelial Cell Morphogenesis in Three-Dimensional Fibrin Matrices Involves the $\alpha_v\beta_3$ and $\alpha_5\beta_1$ Integrins," Am. J. Pathol., 156(5):1673-1683 (2000).
Carmeliet et al., "Angiogenesis in cancer and other diseases," Nature, 407(6801):249-257 (2000).
Carmeliet, P., "Angiogenesis in life, disease and medicine," Nature, 438(7070):932-936 (2005).
Carmeliet, P., "Mechanisms of angiogenesis and artheriogenesis," Nat. Med. 6(4):389-395 (2000).
Cavallaro et al., "Endothelial cadherins and tumor angiogenesis," Exp. Cell Res., 312(5):659-667 (2006).
Chicurel et al., "Cell biology. Cell migration research is on the move." Science, 295(5555):606-609 (2002).
Coultas et al., "Endothelial cells and VEGF in vascular development." Nature, 438(7070):937-945 (2005).

(Continued)

*Primary Examiner* — Ann Lam
(74) *Attorney, Agent, or Firm* — Foley Hoag LLP

(57) ABSTRACT

Provided are methods and devices for formation and study of three-dimensional biological systems, including prokaryotic and eukaryotic cell migration, proliferation, and differentiation.

27 Claims, 36 Drawing Sheets

(56) References Cited

OTHER PUBLICATIONS

Davis et al., "Capillary morphogenesis during human endothelial cell invasion of three-dimensional collagen matrices," In Vitro Cell Dev. Biol. Anim., 36(8):513-519 (2000).

DiMilla et al., "Measurement of Individual Cell Migration Parameters for Human Tissue Cells," AIChE Journal, 38(7):1092-1104 (1992).

Ferrara et al., "Angiogenesis as a therapeutic target," Nature, 438(7070):967-974 (2005).

Gerhardt et al., "VEGF guides angiogenic sprouting utilizing endothelial tip cell filopodia," J. Cell Biol., 161(6):1163-1177 (2003).

Gerthoffer et al., "Mechanisms of Vascular Smooth Muscle Cell Migration," Circ. Res., 100:607-621 (2007).

Ghajar et al., "Mesenchymal stem cells enhance angiogenesis in mechanically viable prevascularized tissues via early matrix metalloproteinase upregulation," Tissue Eng., 12(10):2875-2888 (2006).

Helm et al., "Synergy between interstitial flow and VEGF directs capillary morphogenesis in vitro through a gradient amplification mechanism," PNAS, 102(44):15779-15784 (2005).

Hendrix et al., "A simple quantitative assay for studying the invasive potential of high and low human metastic variants," Cancer Lett., 38(1-2):137-147 (1987).

Huang et al., "Cell tension, matrix mechanics, and cancer development," Cancer Cell, 8(3):175-176 (2005).

Jain et al., "Quantitative angiogenesis assays: progress and problems," Nat. Med., 3(11):1203-1208 (1997).

Jeon et al., "Neutrophil chemotaxis in linear and complex gradients of interleukin-8 formed in a microfabricated device," Nat. Biotechnol., 20(8):826-830 (2002).

Lamalice et al., "Endothelial Cell Migration During Angiogenesis," Circ. Res., 100:782-794 (2007).

Mace et al., "HOXA3 induces cell migration in endothelial and epithelial cells promoting angiogenesis and wound repair," J. Cell Sci., 118:2567-2577 (2005).

Montesano et al., "In Vitro Rapid Organization of Endothelial Cells into Capillary-like Networks Is Promoted by Collagen Matrices," J. Cell Biol., 97:1648-1652 (1983).

Nakayasu et al., "Formation of capillary-like tubes by vascular endothelial cells cocultivated with keratocytes," Invest. Opthalmol. Vis. Sci., 33(11):3050-3057 (1992).

Rojas et al., "Vacuolar-type H+—ATPases at the plasma membrane regulate pH and cell migration in microvascular endothelial cells," Am. J. Physiol. Heart Circ. Physiol., 291:H1147-H1157 (2006).

Rutkowski et al., "A driving force for change: interstitial flow as a morphoregulator." Trends Cell Biol., 17(1):44-50 (2007).

Sagnella et al., "Human microvascular endothelial cell growth and migration on biomimetic surfactant polymers," Biomaterials, 25(7-8):1249-1259 (2004).

Selmeczi et al., "Cell Motility as Presistent Random Motion: Theories from Experiments," Biophysical Journal, 89:912-931 (2005).

Shiu et al., "The role of mechanical stresses in angiogenesis," Crit. Rev. Biomed. Eng., 33(5):431-510 (2005).

Shizukuda et al., "Vascular Endothelial Growth Factor-Induced Endothelial Cell Migration and Proliferation Depend on a Nitric Oxide-Mediated Decrease in Protein Kinase Cδ Activity," Circ. Res., 85:247-256 (1999).

Sieminski et al., "The relative magnitudes of endothelial force generation and matrix stiffness modulate capillary morphogenesis in vitro," Exp. Cell Res., 297(2):574-584 (2004).

Sudo et al., "Transport-mediated angiogenesis in 3D epithelial coculture," FASEB J. 23(7):2155-2164 (2009).

Suresh, S., "Biomechanics and biophysics of cancer cells," Acta Biomater., 3(4):413-438 (2007).

Vickerman et al., "Design, Fabrication and Implementation of a Novel Multi Parameter Control Microfluidic Platform for Three-Dimensional Cell Culture and Real-Time Imaging," Lap Chip, 8(9):1468-1477 (2008).

Walker et al., "A passive pumping method for microfluidic devices," Lab Chip, 2(3):131-134 (2002).

Wenger et al., "Modulation of in vitro angiogenesis in a three-dimensional spheroidal coculture model for bone tissue engineering," Tissue Eng., 10(9-10):1536-1547 (2004).

Yamaguchi et al., "Cell migration in tumors," Curr. Opin. Cell Biol., 17(5):559-564 (2005).

Yamamura et al., "Effects of the mechanical properties of collagen gel on the in vitro formation of microvessel networks by endothelial cells," Tissue Eng., 13(7):1443-1453 (2007).

Yancopoulos et al., "Vascular-specific growth factors and blood vessel formation," Nature, 407(6801):242-248 (2000).

Zhao et al., "Morphological Observation and In Vitro Angiogenesis Assay of Endothelial Cells Isolated From Human Cerebral Cavernouse Malformations," Stoke, 38:1313-1319 (2007).

Diao et al., "A Three-Channel Microfluidic Device for Generating Static Linear Gradients and its Application to The Quantitative Analysis of Bacterial Chemotaxis," Lab Chip, 6:381-388 (2006).

Saadi et al., "Generation of Stable Concentration Gradients in 2D and 3D Environments Using a Microfludic Ladder Chamber," Biomed Microdevices, 9:627-635 (2007).

\* cited by examiner

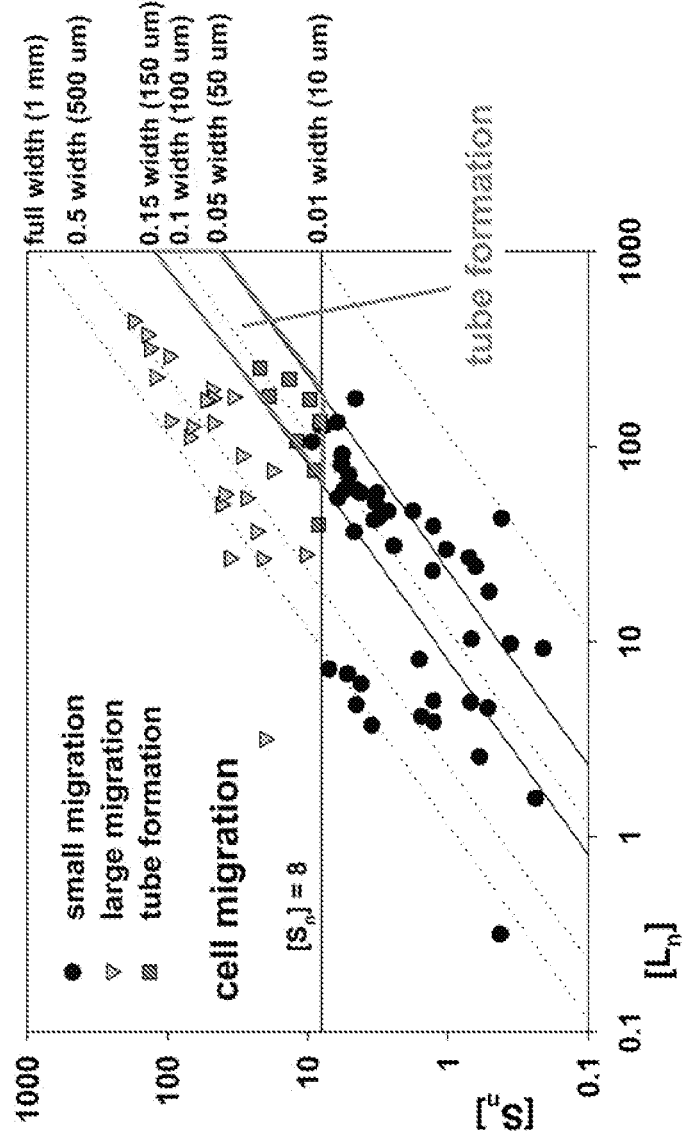
Figure 7A
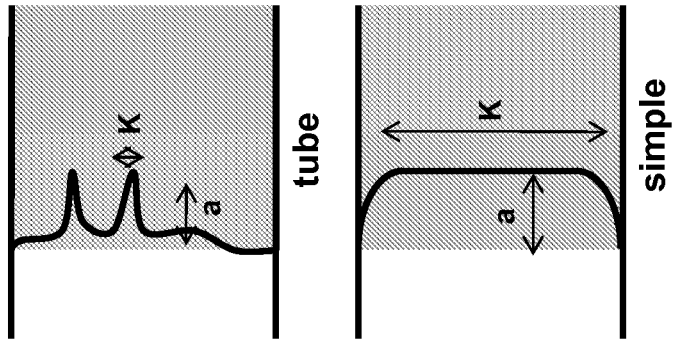
Figure 7B
Figure 7C

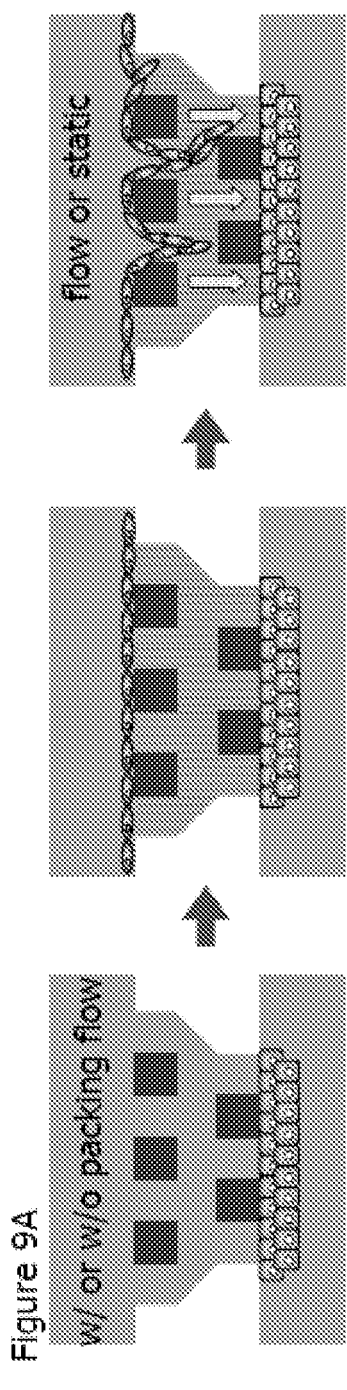
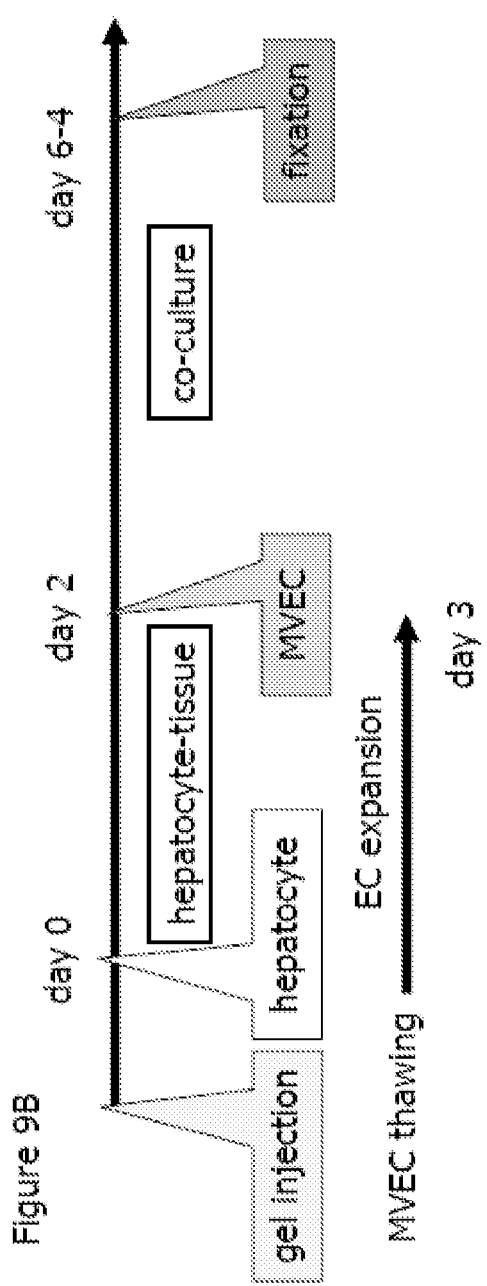
Figure 9

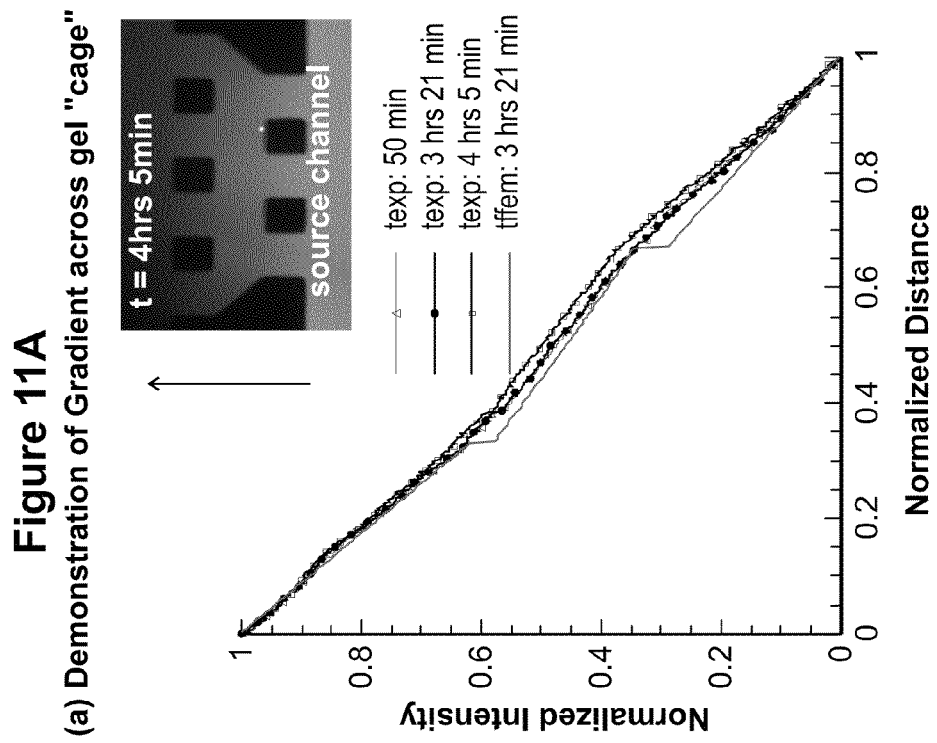
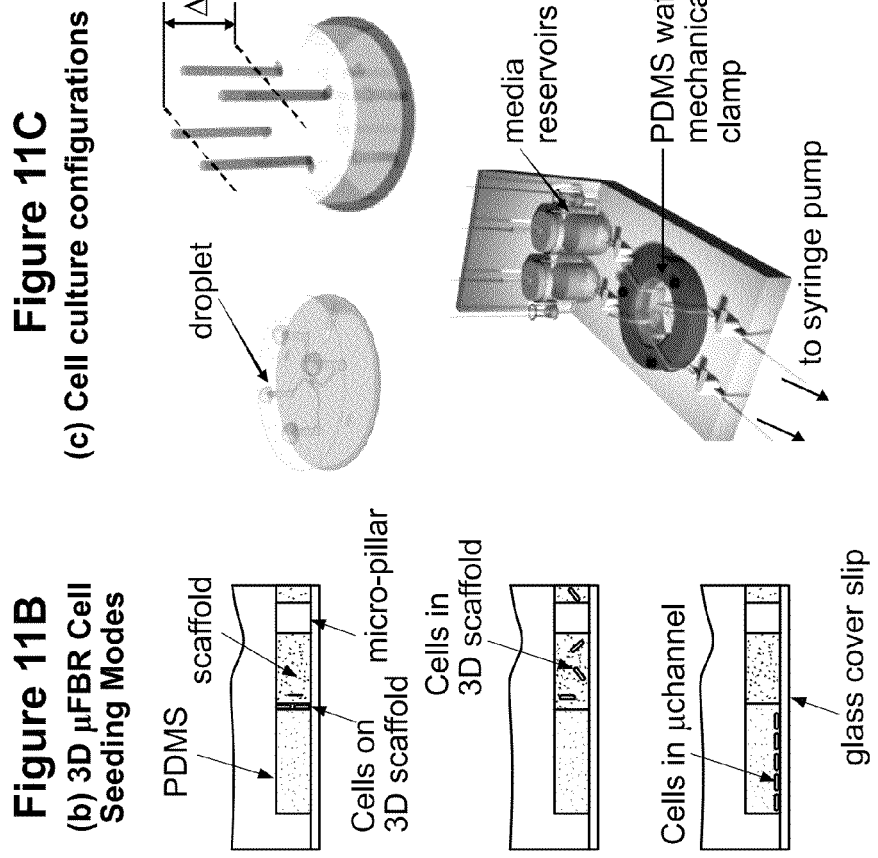
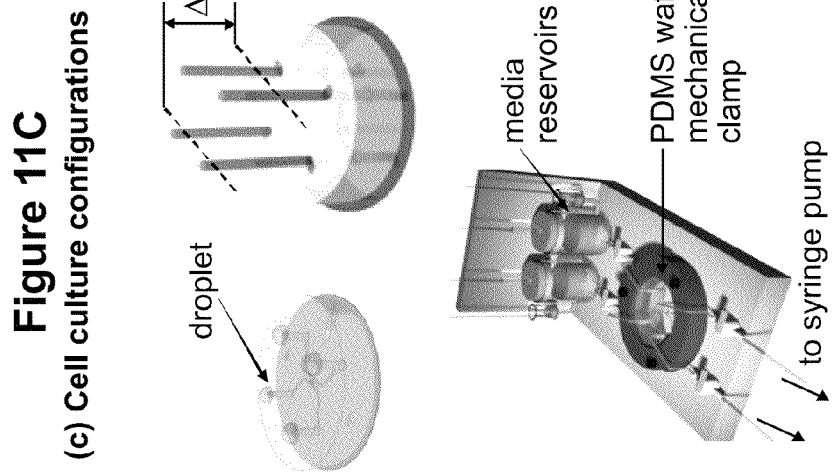
Figure 11A (a) Demonstration of Gradient across gel "cage"
Figure 11B (b) 3D µFBR Cell Seeding Modes
Figure 11C (c) Cell culture configurations Figure 20
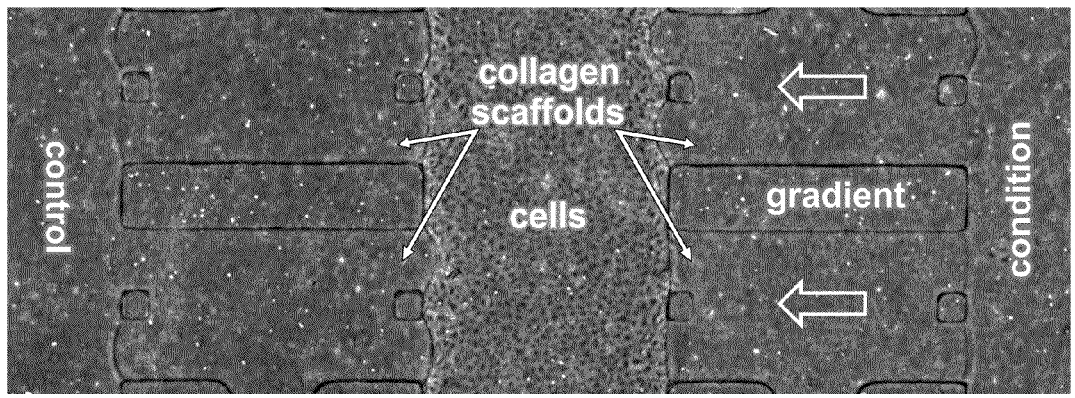
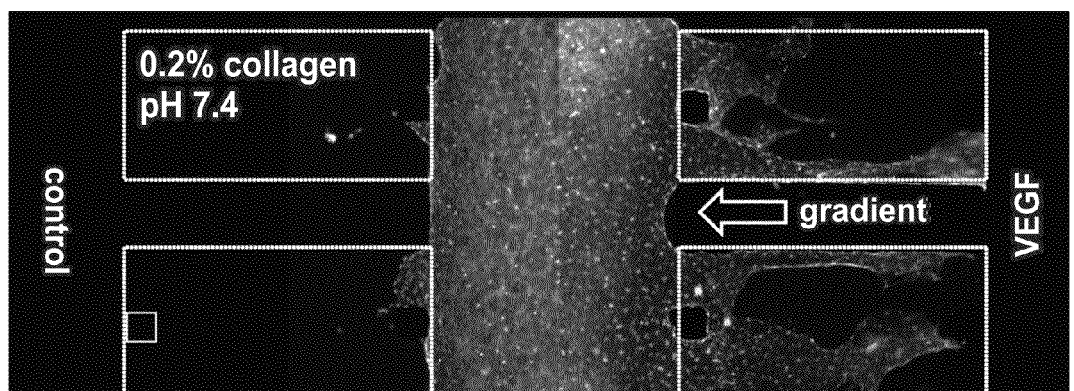
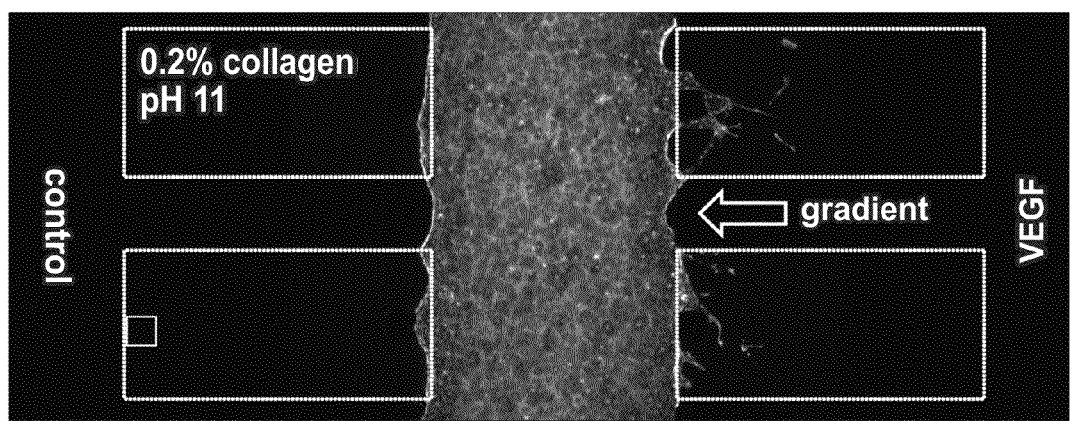

Figure 20 (continued)
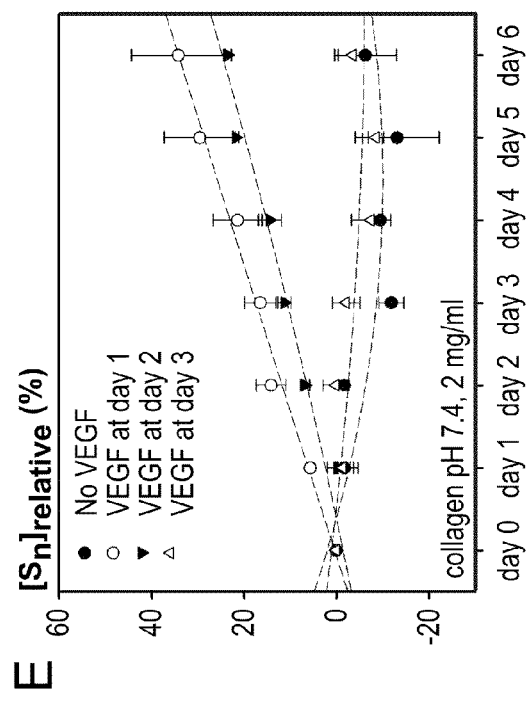
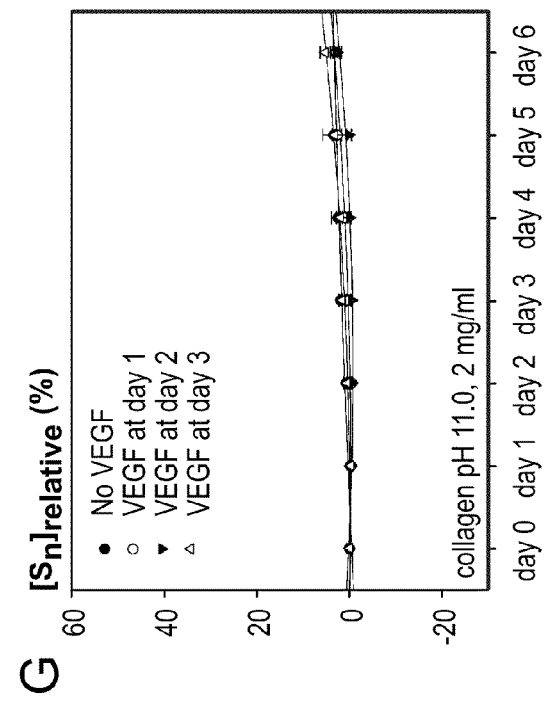
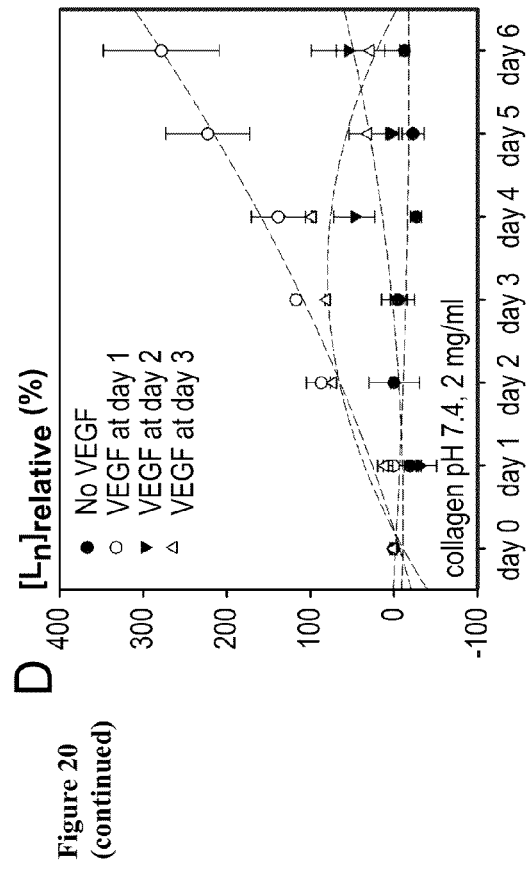
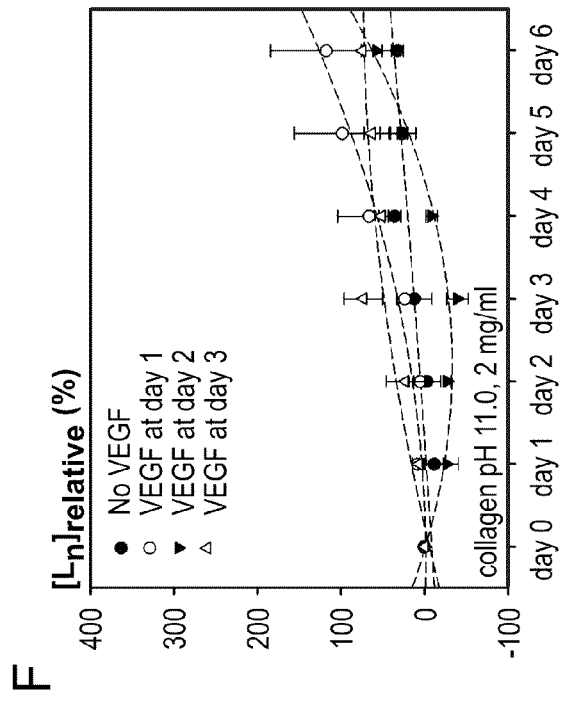

Figure 22
(a) Demonstration of Gradient across gel "cage"
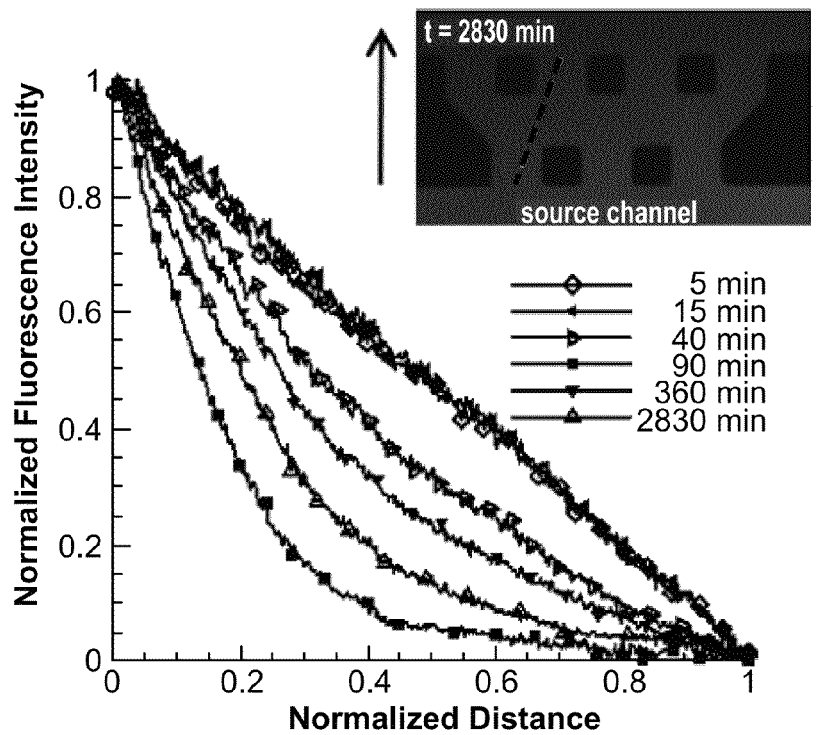
(b) 3D μFBR Cell Seeding Modes
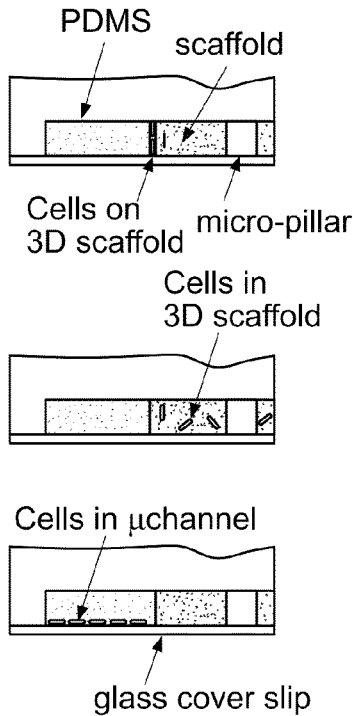
(c) Cell culture configurations
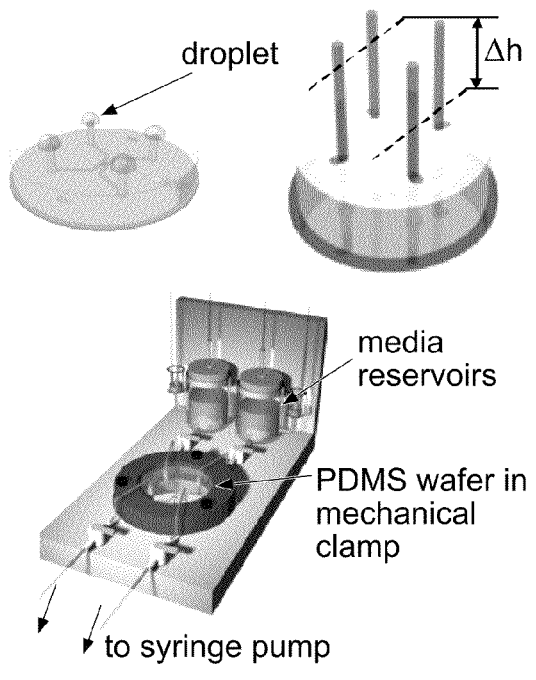

Figure 22 (continued)
(d)
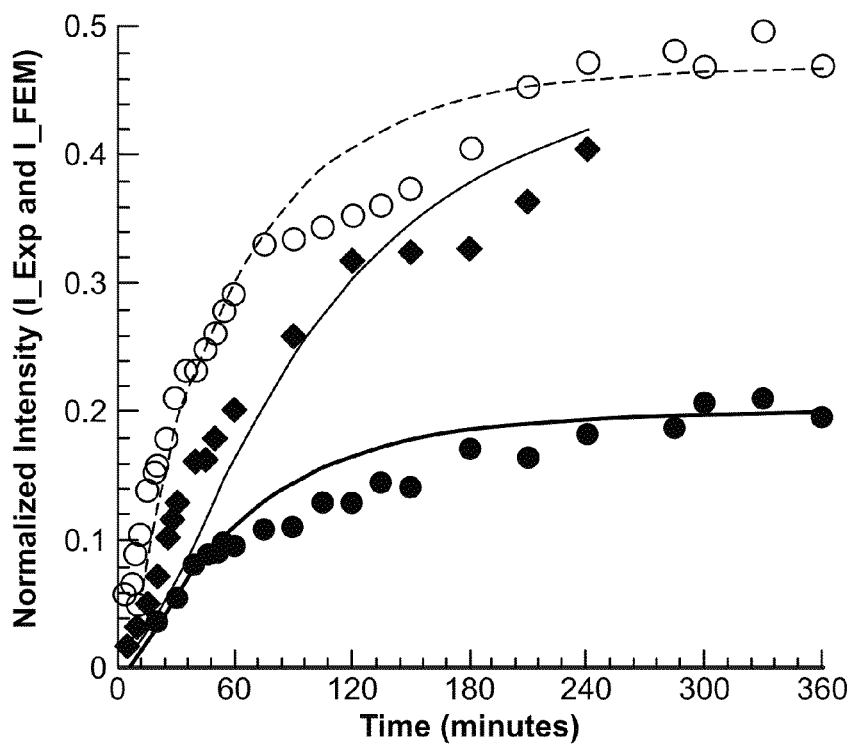
(e)
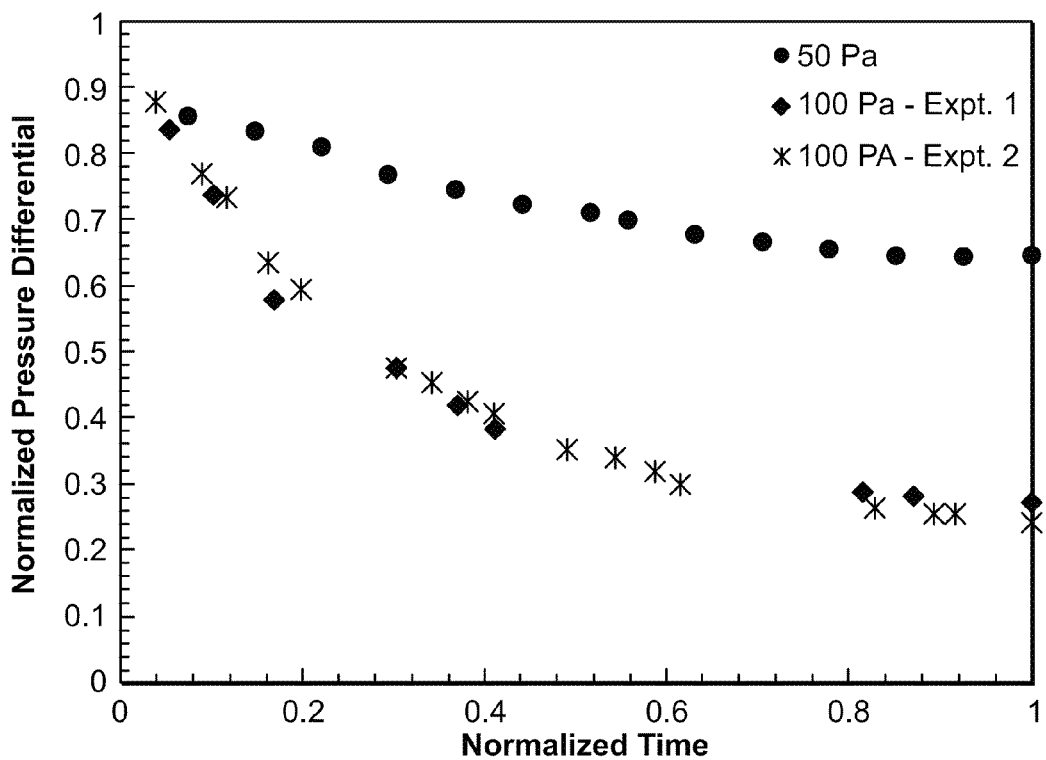

Figure 26
A
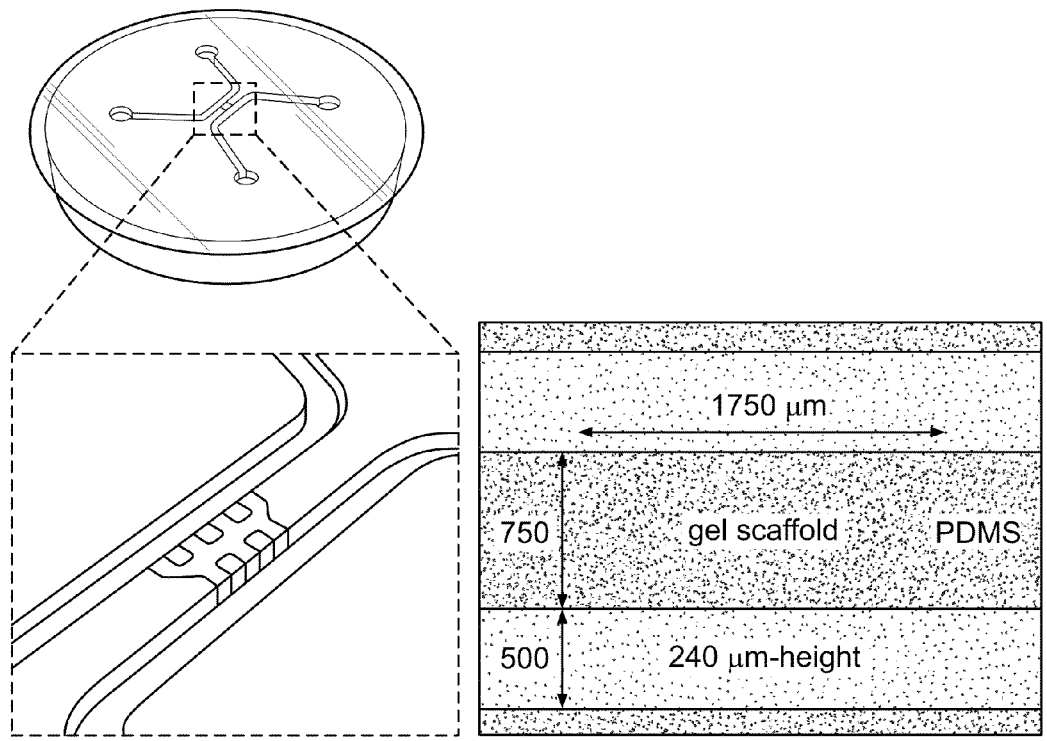
B
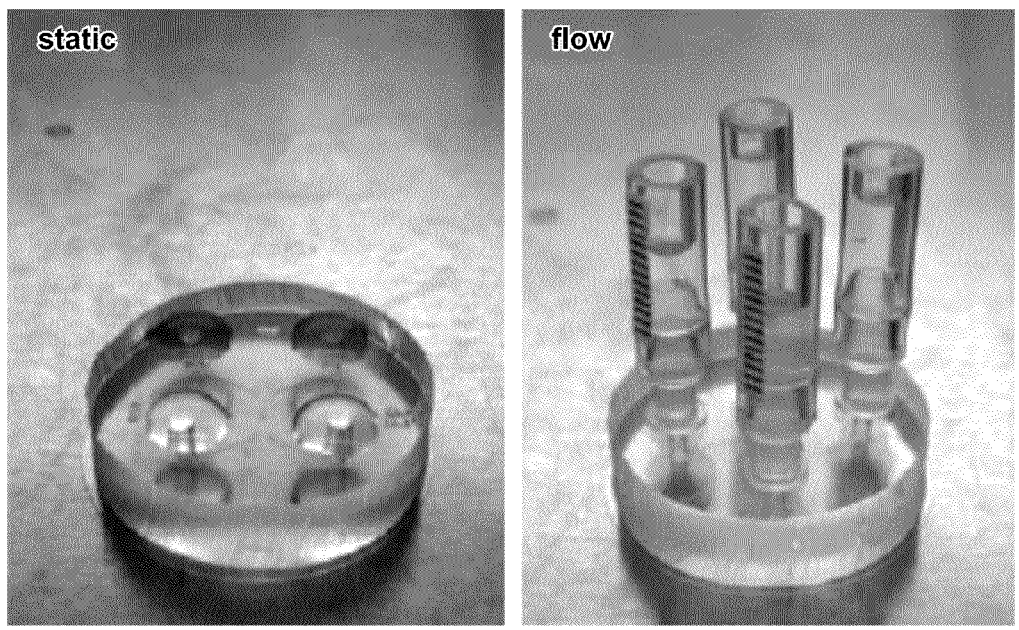

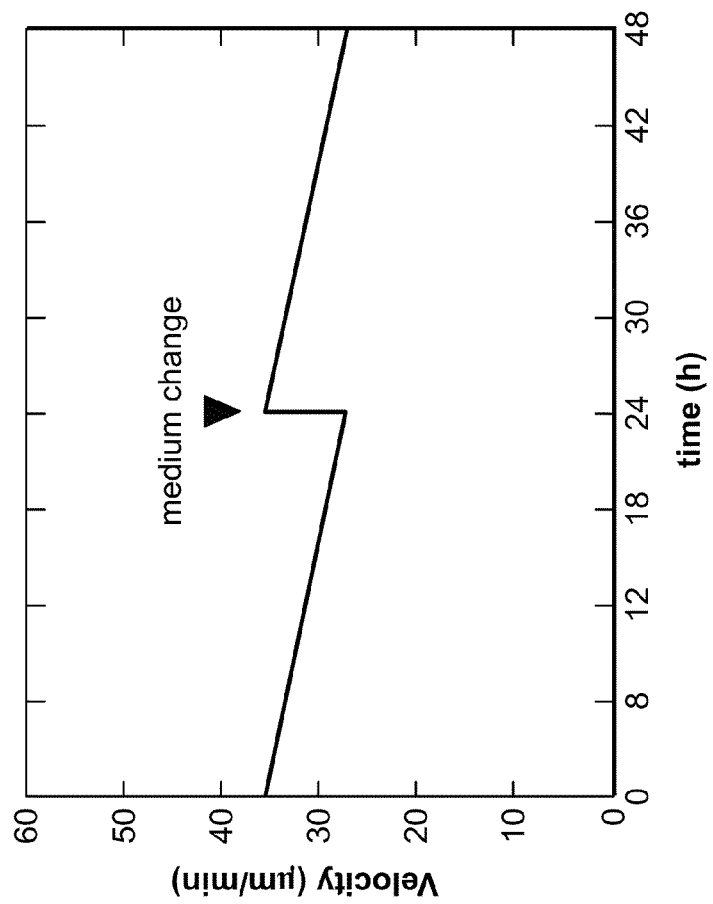
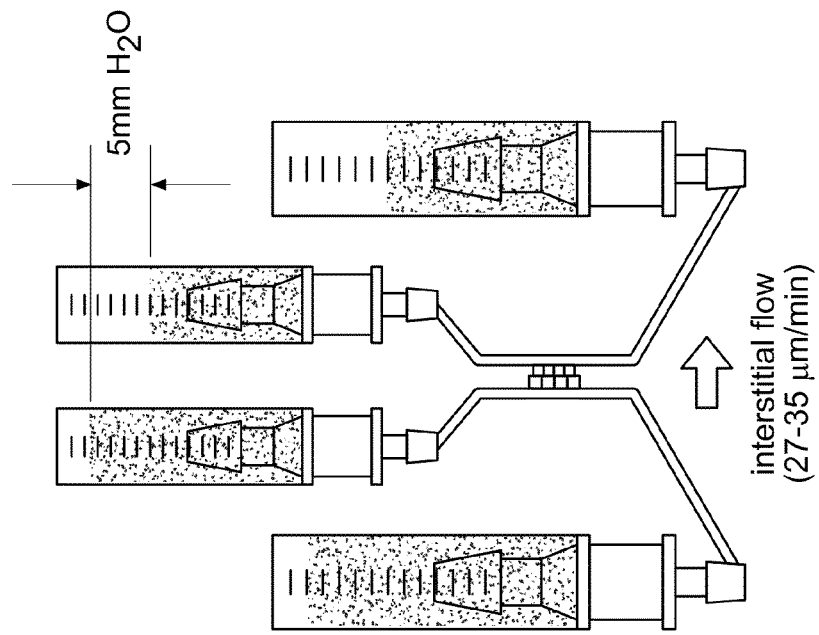
Figure 27

Figure 32
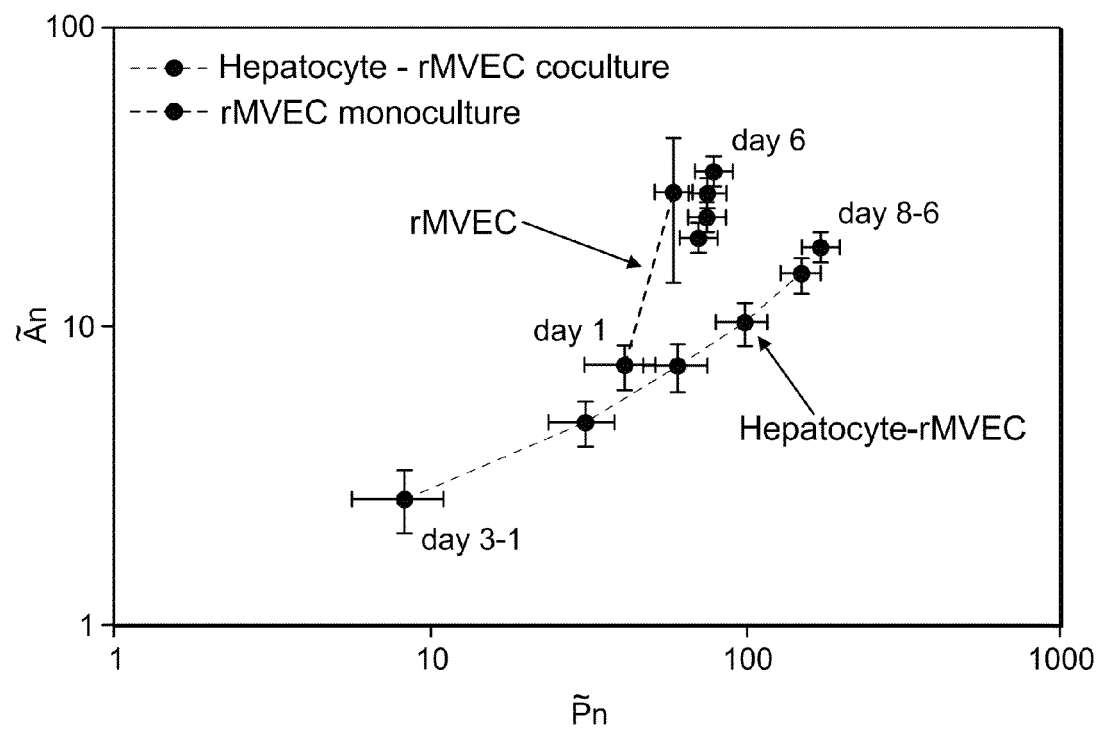
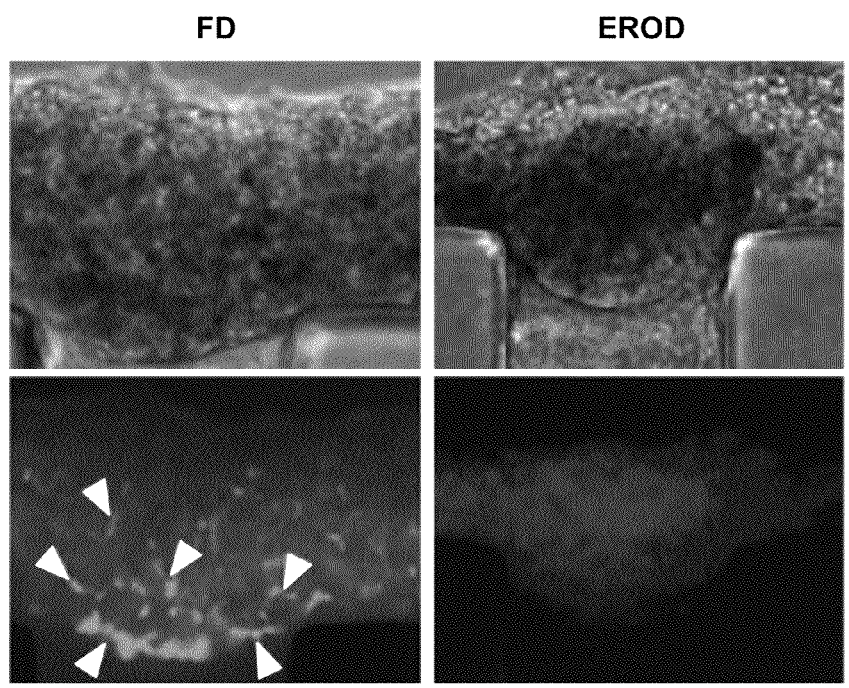

THREE-DIMENSIONAL MICROFLUIDIC PLATFORMS AND METHODS OF USE THEREOF

RELATED APPLICATIONS

This application is the U.S. National Stage of International Patent Application No. PCT/US2009/039434, filed Apr. 3, 2009, which claims the benefit of priority to U.S. Provisional Patent Application Ser. No. 61/123,344, filed Apr. 8, 2008.

GOVERNMENT SUPPORT

This invention was made with government support under Grant No. I-R01-EB-003805-01A1 awarded by the National Institute of Biomedical Imaging and Bioengineering, National Institutes of Health. The government has certain rights in the invention.

BACKGROUND

Cell migration is essential for a variety of physiological and pathological processes, such as angiogenesis, cancer metastasis, wound healing and inflammation. In the vascular system, significant efforts have focused on cell migration in the context of capillary morphogenesis. Through these studies, various mechanical and biochemical factors have been identified as critical in regulating endothelial cell migration and tube formation, such as chemotactic or chemokinetic effects of single or multiple growth factors[1], interstitial fluid flow[2,3] and matrix stiffness[4,5]. Despite the detailed understanding of individual components, how these factors are integrated to produce a specific cellular response has yet to be elucidated, creating the need for a versatile in vitro system in which these environmental factors can be studied in a controlled fashion. Achieving this will facilitate investigations that lead to a better understanding of how biochemical and mechanical factors act together in physiological and pathophysiological processes and ultimately contribute to improved tissue engineering and therapeutic strategies.

Understanding cell migration in capillary morphogenesis is therapeutically important because of its relation to human diseases and developmental phenomena[6]. Typical cell migration assays are unable to integrate complex environmental factors, particularly those that facilitate the formation of new tube-like structures from pre-formed capillaries or a cell monolayer within a three dimensional environment. One of the current capillary morphogenesis assays produces planar tubular networks on ECM-like substrates[7-9]. Capillary-like structures formed with this technique, however, have a reversed cell polarity with media on the outside and scaffolding materials on the inside[7]. Other approaches include sandwiching one cell monolayer between two layers of scaffold material[8] and inducing capillary invasion by introducing chemical gradients[9]. These experiments have provided a foundation for understanding capillary morphogenesis, but are limited by an inability to image cell invasion in-plane, which would lead to more detailed characterization of the factors influencing this biological process.

Historically, many assays have been used to study cell migration[10], such as the wound assay[11,12], the TEFLON® fence assay[13] and the Boyden chamber[14,15]. Both the wound assay and TEFLON® fence assay are limited to studying cell migration in 2D. The Boyden chamber mimics most closely the physiologic 3D environment, but is not conducive to quantifying cell migration in real time. Another assay with endothelial cell coated beads or spheroids embedded in collagen gel was able to generate tube-like structures in a three dimensional environment. The assay allowed the generation of stable tube-like structures and the co-culture with other cell types[16-18], but the initial endothelial cell seeding surface is a rigid bead that does not allow for physiological factors such as a fluid-matrix interface and fluid flow experienced by endothelial cells in vivo. Furthermore, with the current assays, the chemokinetic and chemotactic effects are difficult to differentiate. In the context of cell migration, chemotaxis represents cells migrating towards the chemoattractant, while chemokinesis represents an increased motility in the presence of a particular biochemical factor. Due to technical difficulties in maintaining a controlled gradient, the two effects are not easily distinguished. Challenges to the existing techniques are: (i) to have precise control of the mechanical and biochemical factors in a physiologically-relevant condition, (ii) to have excellent optical resolution in real time, and (iii) to minimize sample variability and enhance sensitivity for quantification.

Microfabrication and microfluidic technology has the potential to overcome these challenges in studying cell migration by allowing for precise control of multiple environmental factors. However, current efforts in this area have continued to investigate isolated factors. For example, microfabricated patterns have enabled the demonstration of preferential migration in the direction of increased stiffness[19,20]. Microfluidic technology has also enabled the precise control of biochemical gradients and quantification of the resulting cell migrations[21].

SUMMARY

Provided are devices and methods for the formation and study of three-dimensional biological responses, including prokaryotic and eukaryotic cell migration, proliferation, and differentiation, as well as for the development of in vitro systems capable of replicating critical biological functions.

Further objectives and advantages of the present invention will become apparent from the detailed description and claims.

BRIEF DESCRIPTION OF THE DRAWINGS

FIG. 7A is a graph showing the use of a microfluidic device in an angiogenesis assay. FIGS. 7B and 7C are depictions of how tube formation is calculated and differentiated from simple cell migration.

FIG. 9A is a schematic illustration of the use of a microfluidic device having two fluid-flow paths in a cell co-culture assay. In this device the scaffold includes collagen, the optically transparent material is a microscope cover glass, and both the substrate (poly-dimethyl siloxane or "PDMS") and the coverglass are coated with various materials, such as collagen or poly-D-lysine ("PDL"). Hepatocytes are introduced into a first fluid-flow path and grown under conditions such that they form at least one cell layer at the surface of the collagen scaffold. Human microvascular endothelial cells ("MVEC") are introduced into a second flow path and grown under conditions where there is either fluid flow through the flow path or no fluid flow ("static" conditions). Endothelial cell migration into the scaffold in the direction of the hepatocytes, and endothelial cell differentiation into tubules is detected. FIG. 9B is a schematic illustration of a time-course of a MVEC-hepatocyte co-culture experiment. Different combinations of cell types are introduced into the device in various embodiments of the invention.

FIG. 11A is a line graph demonstrating the formation of a gradient across the scaffold. FIG. 11B is a schematic illustration showing cell location in a portion of the microfluidic device. Cells introduced into a fluid-flow path may adhere to the surface of the scaffold or may invade the scaffold material. Alternatively, cells may adhere to the optically transparent material (here a glass coverslip) that is in contact with the fluid-flow path. FIG. 11C is a schematic illustration demonstrating one embodiment of the invention in which fluids (from media reservoirs) are introduced into the device, by capillary action or by application of a vacuum (from a pump source) at the fluid outlets.

FIGS. 20A-C are a series of photographs showing a portion of a microfluidic device demonstrating multiple fluid-flow paths and scaffolds. FIGS. 20D-G are a series of line graphs showing directed cell migration through scaffolds over time in response to stimuli such as VEGF.

FIG. 22A depicts a demonstration of gradient across gel "cage." Fluorescent dextran (40 kDa) was used to demonstrate the capability of generation gradients in the μFD. Shown are the time-course of fluorescent intensity and concentration of dextran (used to simulate nonreactive solute within that size range) across the gel "cage." The plot shows representative experimental curves plotted for over 40 hours. FIG. 22B depicts a schematic of cell culture assays. (top) EC sprouting assay. Cells are cultured on a 3-dimensional gel with physiological relevant polarity. (middle) 3D encapsulation assay. Cells are suspended in the gel and are initially separated from each other. (bottom) 2D migration assay. Cells form monolayer predominantly on glass substrate (non-compliant) coated with ECM material (fibronectin) FIG. 22C depicts various culture flow configurations. (1) For static cultures, droplets of media are placed on inlet and outlet ports. Devices are kept in local high humidity (Petri dish with water) secondary container in the incubator. (2) Setup used for imposing pressure gradient across gel cage, differential in height of liquid reservoirs. (3) Microfluidic platform. Schematic of platform used for generating physiological levels of shear stress in micro channels. FIG. 22D depicts plots representing values of normalized intensity at fixed locations in the gel region, solid lines are theoretical predictions and shape-markers (circles (open-middle, solid-near sink channel) and squares for exemplary devices. FIG. 22E depicts experimental results for the evolution of normalized pressure differential (dP/dPmax) for generating interstitial flow through three-dimensional scaffold in DFD, values in Pa indicate initial pressure differential.

FIG. 23a shows a prepared PDMS device made by soft lithography and surface treatment. FIG. 23b depicts a filled gel scaffold (shaded) in the scaffold channel between the channels. FIG. 23c depicts media (left, right, and center) filling both channels. FIG. 23d depicts cell seeding (spheres) in the central cell channel. FIG. 23e depicts chemical factors (right) applied in the condition channel. FIG. 23f depicts microfluidic device after filling of medium and chemical factors. Droplets are placed on all inlet ports to avoid evaporation of medium from the channels. Medium can be replaced with capillary forces generated by simply aspirating the existing droplets and adding new ones. FIG. 23g depicts a schematic for microfluidic cell migration assay enabling direct comparison of cell migration behavior between the condition and control sides.

FIG. 26 depicts the microfluidic coculture platform for the vascularization of tissue-engineered constructs. A) Schematic diagram and dimension of the microfluidic device made of PDMS. Two parallel microfluidic channels are formed between a micropatterned PDMS device and a coverslip. Gel scaffold (e.g., type I collagen) is located between the microfluidic channels with a mechanical support of PDMS posts. B) Pictures of the microfluidic device cultured under static (left) and flow (right) conditions. Droplets of culture medium are placed on each outlet of a microfluidic channel for static culture. Reservoirs are connected to microfluidic channels for flow culture.

FIG. 27 depicts interstitial flow across the gel scaffold generated by a 5-mm $H_2O$ pressure difference between two microfluidic channels. The permeability of collagen gel with hepatocytes was determined by measuring displacement of the medium level in reservoirs and velocity was calculated based on the gel permeability and analytical solutions. The velocity decreases over time but is restored by changing the culture medium.

FIG. 32 depicts quantification of rMVEC morphogenesis. Graph shows the relation between the normalized area increase $A^\sim_n$ and perimeter increase $P^\sim_n$ of the migrating rMVECs on day n. In coculture, the data represent larger $P^\sim_n$ and smaller $A^\sim_n$ than those of a control culture. Each plot represents the values on each day. "Day 3-1" represents day 3 of hepatocytes and day 1 of rMVECs. Error bars=SEM (n=16, N=4 for hepatocyte-rMVEC coculture; n=15, N=3 for rMVEC culture). Pictures show corresponding phase-contrast and fluorescent images of hepatocyte tissue-like structures. Left panels: metabolite of FD secreted into BC (arrowheads) in hepatocytes on day 13-11 of coculture. Right panels: EROD activity of hepatocytes on day 10-8 of coculture.

DETAILED DESCRIPTION

Figure 1:
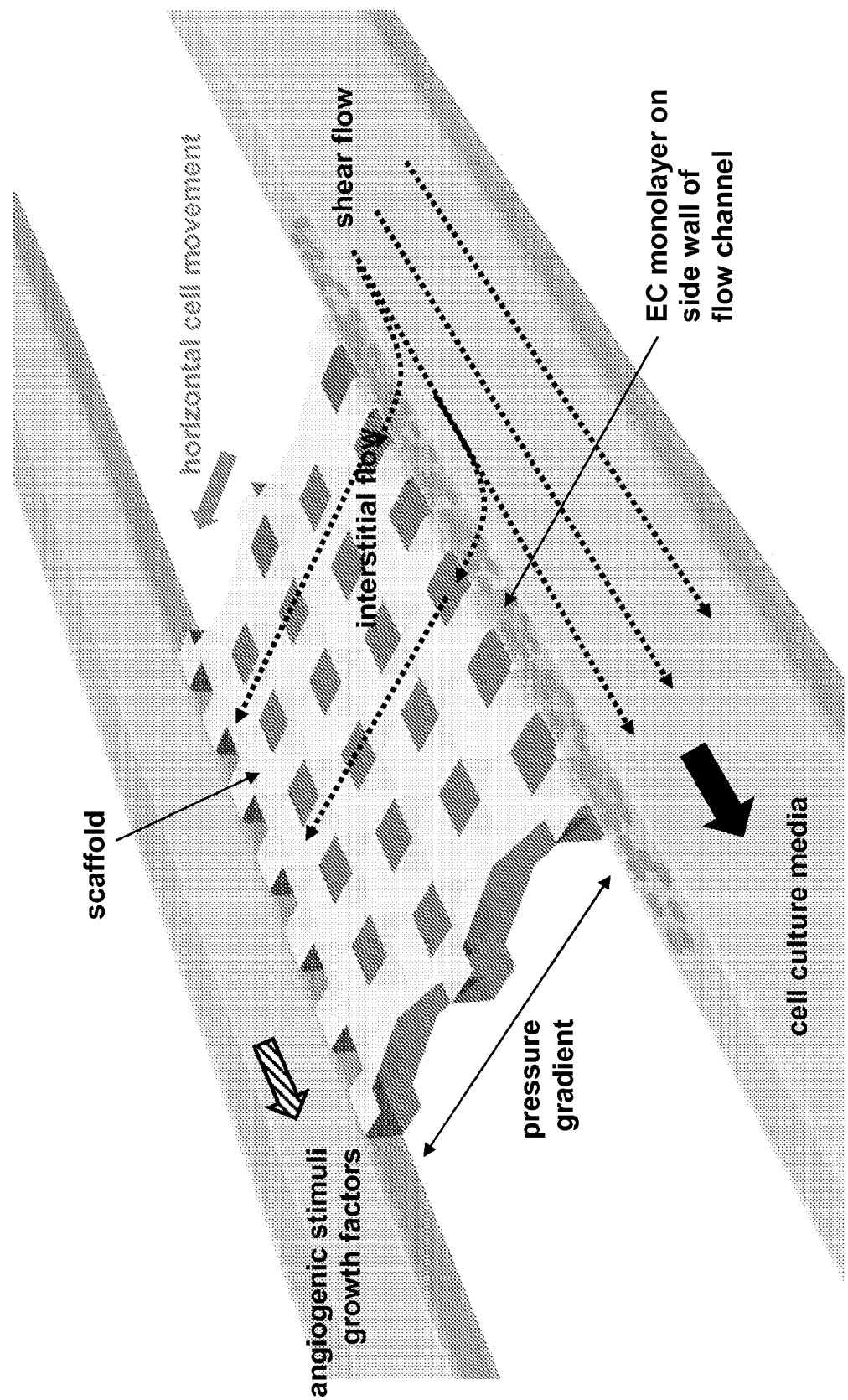
FIG. 1 is a schematic illustration of a microfluidic device having two fluid-flow paths.
Figure 2:
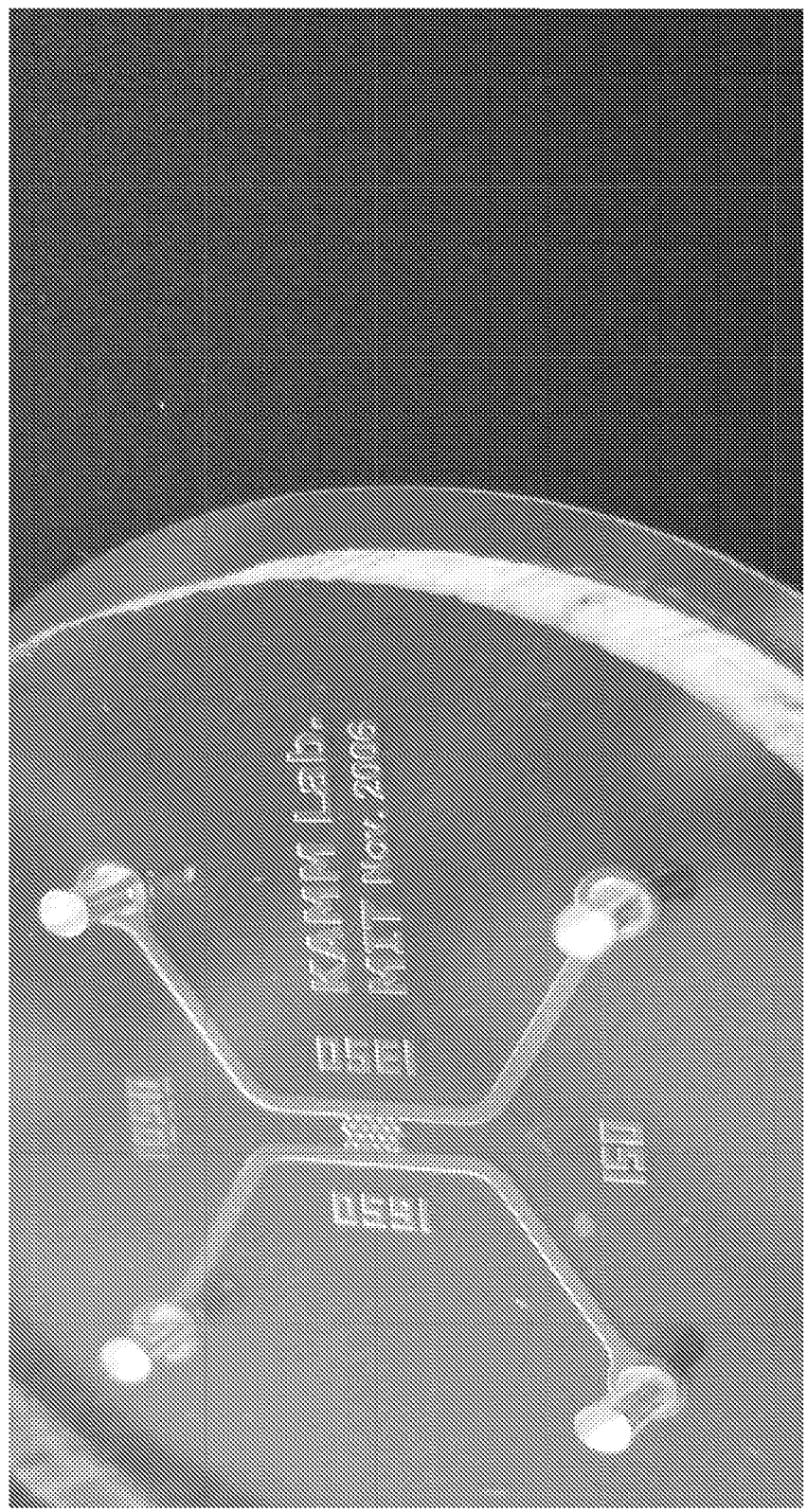
FIG. 2 is a photograph of a microfluidic device having two fluid-flow paths. Cells of interest are introduced (or "seeded") in either or both of the two flow paths, or suspended in the gel scaffold.
Figure 3:
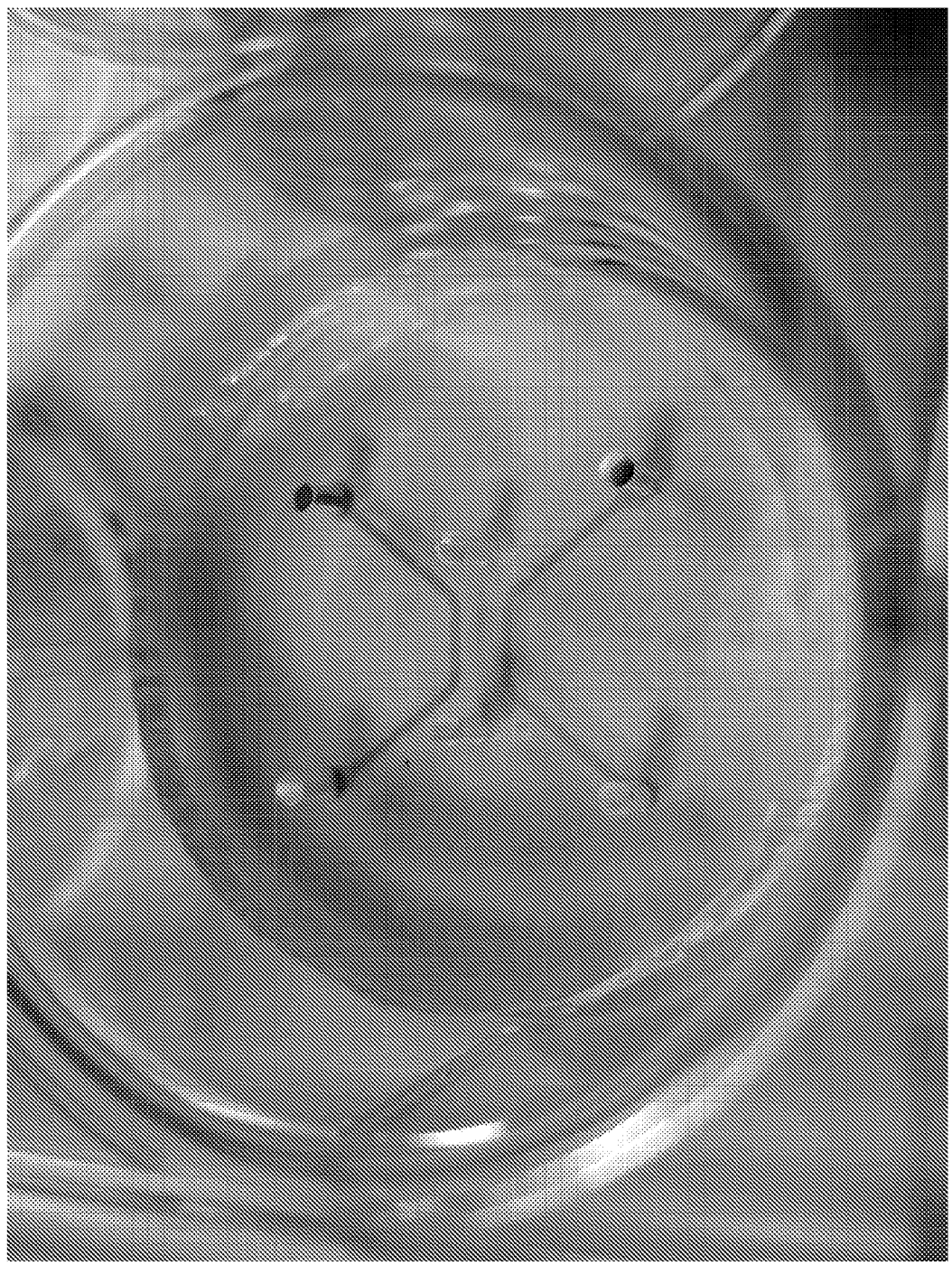
FIG. 3 is a photograph of a microfluidic device having three fluid-flow paths. One or more cell types of interest are introduced (or "seeded") in any combination of one or more of the three flow paths, or suspended in the gel scaffold.
Figure 4A:
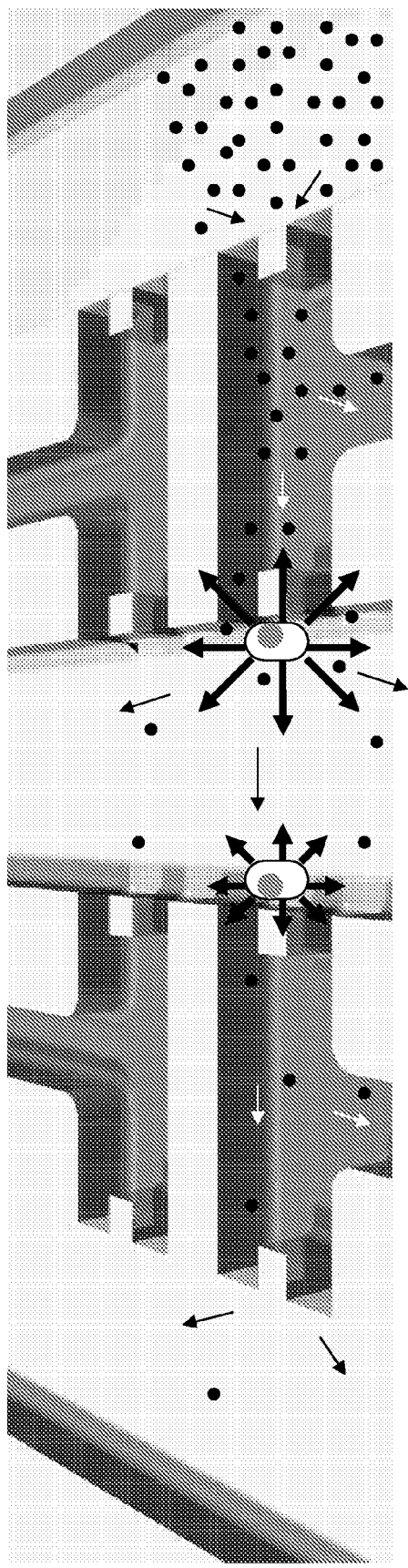
FIG. 4A is a schematic illustration of a microfluidic device having three fluid-flow paths.
Figure 4B:
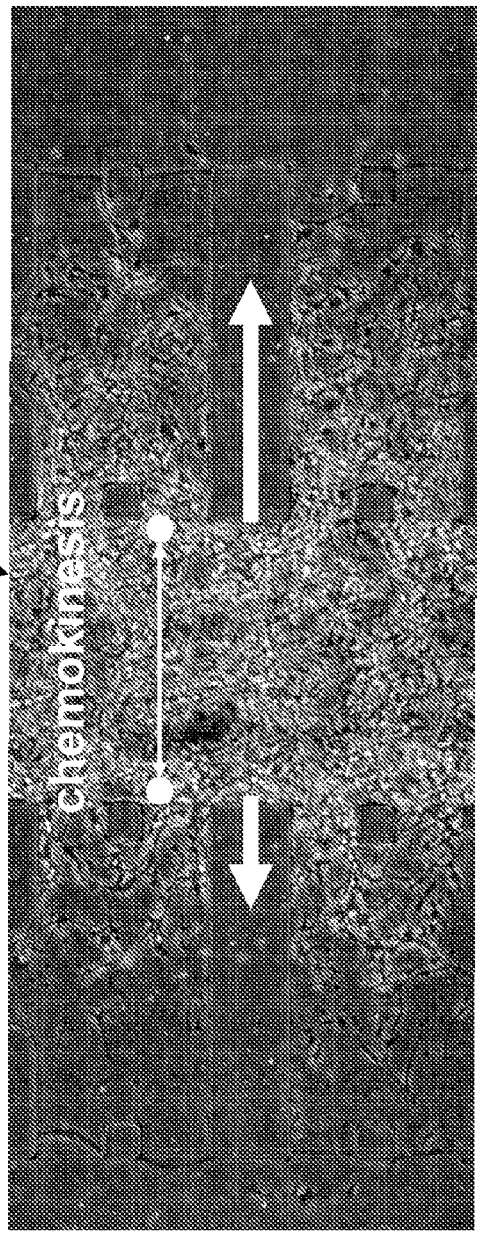
FIG. 4B is a photograph of a microfluidic device having three fluid-flow paths. Eukaryotic cells were introduced into the interior flow path and migrated chemotactically to the exterior flow paths.
Figure 5:
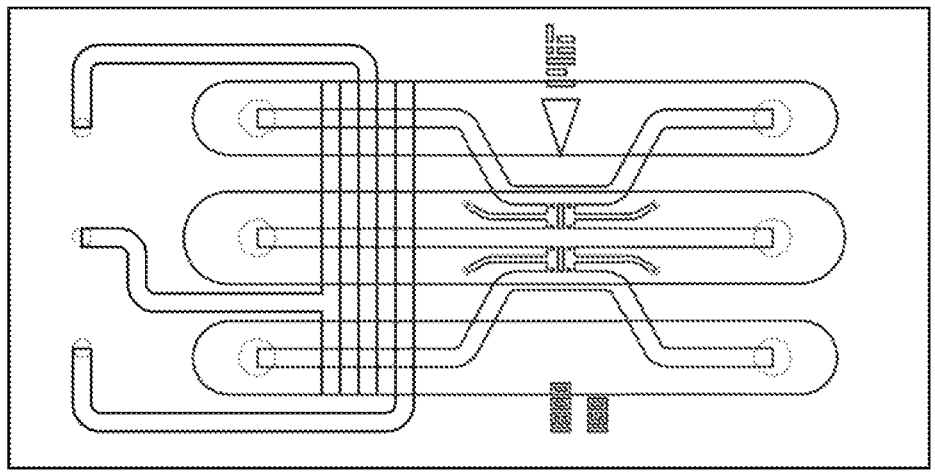
FIG. 5 is a schematic illustration of a microfluidic device having three fluid-flow paths and two transverse paths, and optionally providing inlets (such as for pressurized or unpressurized air) and valves to control fluid flow in one or more of the flow paths.
Figure 6:
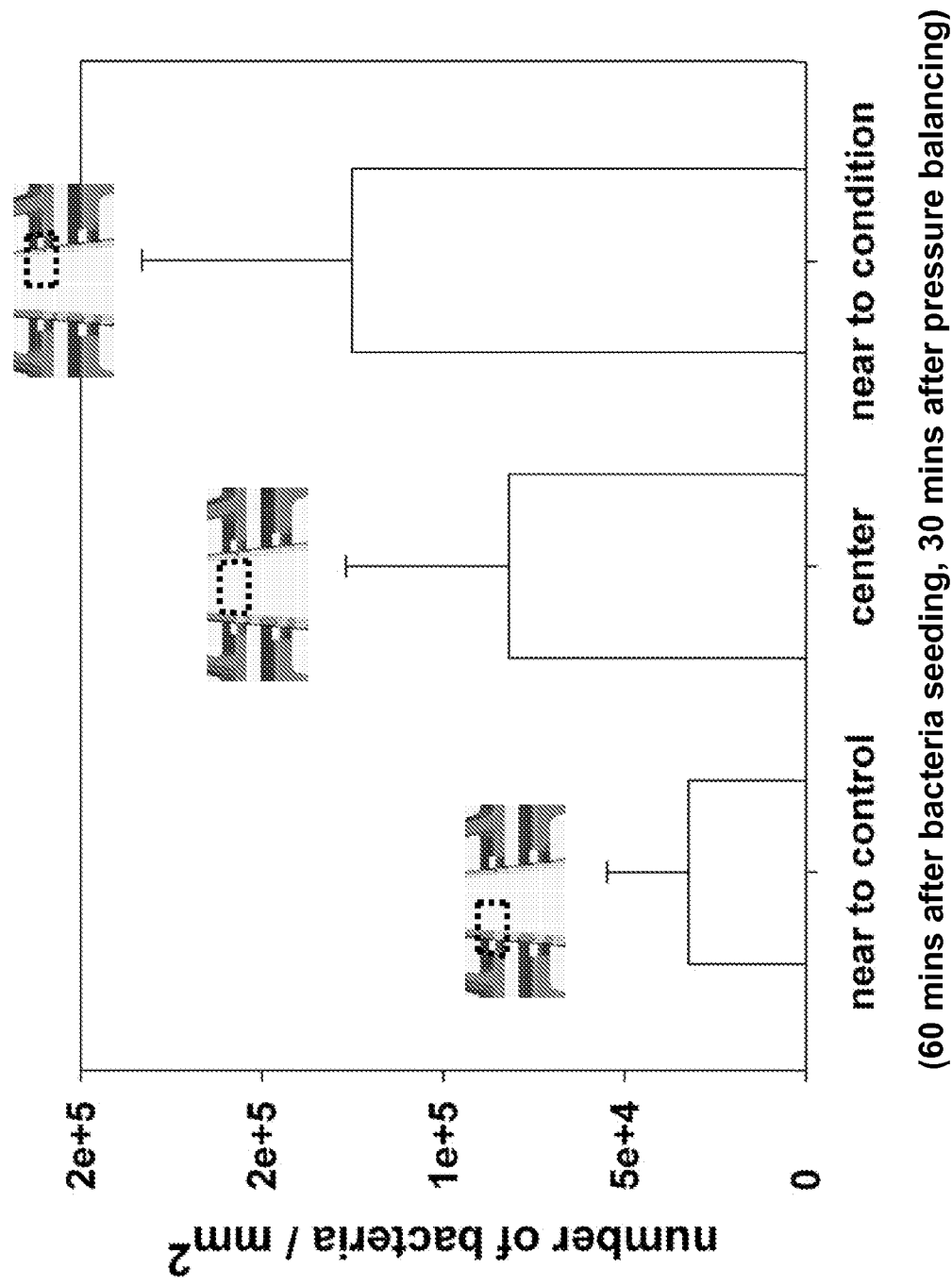
FIG. 6 is a bar graph showing the use of a microfluidic device having three fluid-flow paths in a chemotaxis assay for bacteria. Bacteria were introduced (or "seeded") into the interior flow path, and the chemotactic migration of bacteria towards a stimulus (or "condition") placed in one exterior flow path was measured relative to bacterial migration towards a control placed in the other exterior flow path.
Figure 8:
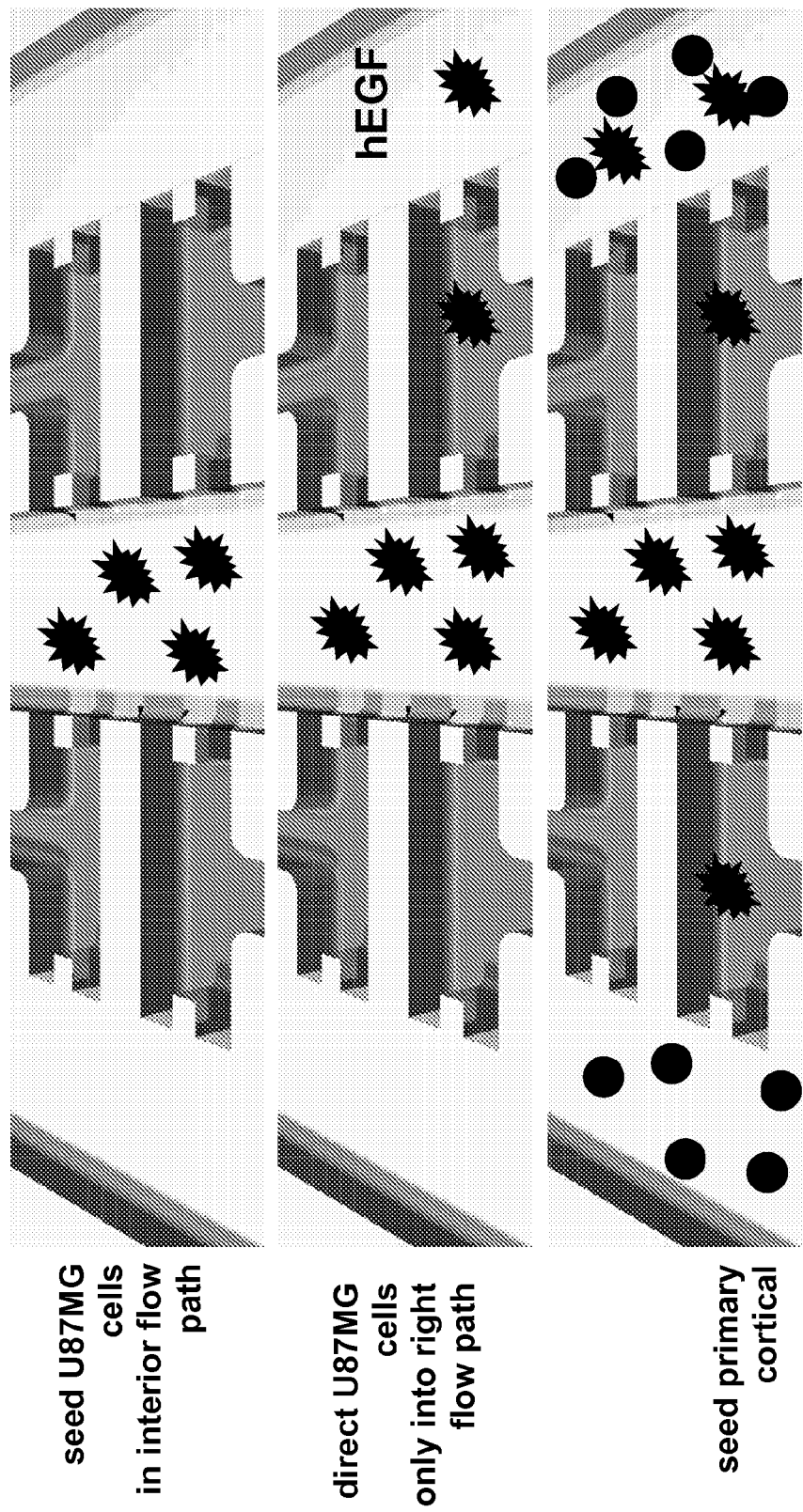
FIG. 8 is a schematic illustration of the use of a microfluidic device having three fluid-flow paths in a cell co-culture assay. U87MG cells are introduced into the interior flow path, human epidermal growth factor ("hEGF") is introduced into one exterior flow path, and primary cortical neurons are introduced into the other exterior flow path.
Figure 10:
FIG. 10 is a photograph of an embodiment of the invention in which microfluidic devices are placed in adjacent wells of a multi-well tissue culture plate; further modifications are provided to enable high-throughput uses of the device.
Figure 12B:
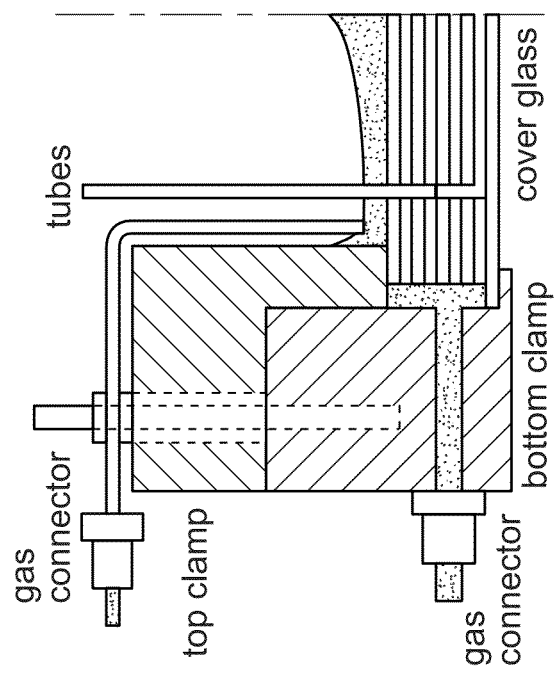
FIG. 12B is a photograph of a microfluidic device and associated system for maintaining physiological conditions in a microfluidic device environment.
Figure 12A:
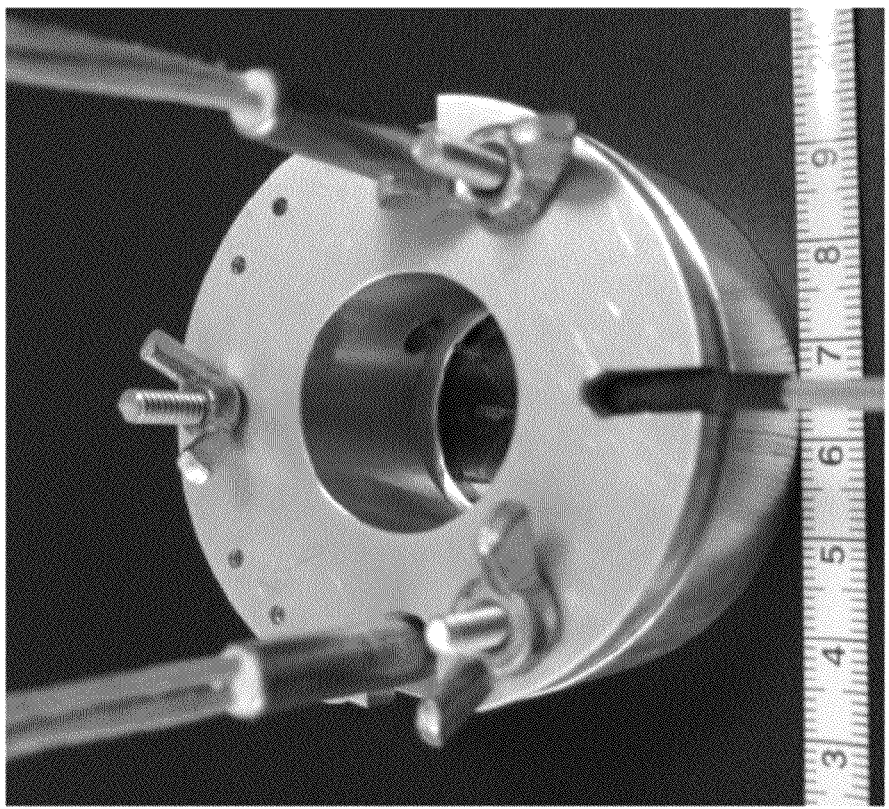
FIG. 12A is a schematic cross-sectional illustration of a portion of a microfluidic device demonstrating how temperature and humidity are controlled in the device.
Figure 13:
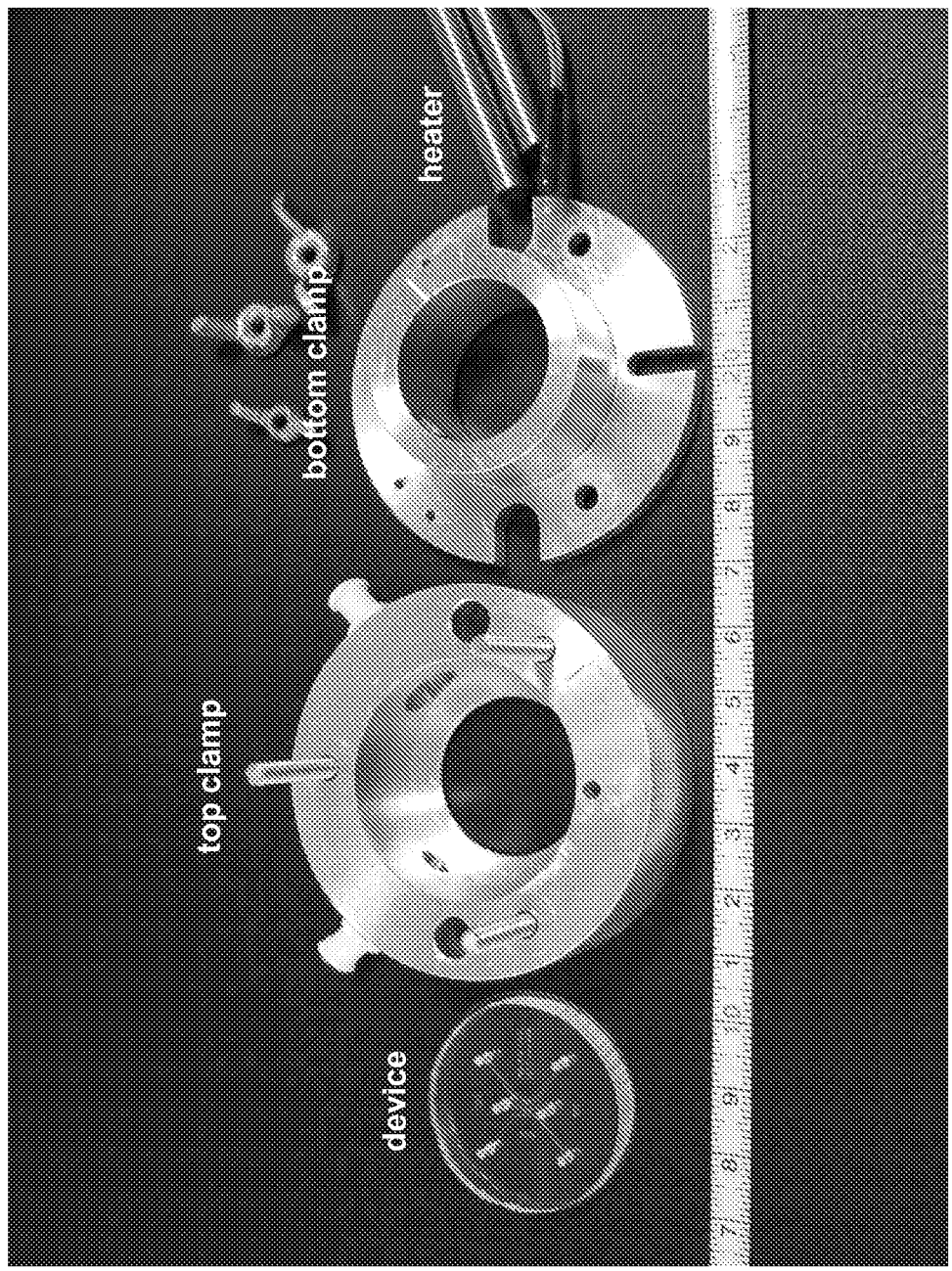
FIG. 13 is a photograph of a microfluidic device and associated system shown assembled in FIG. 12B.
Figure 14:
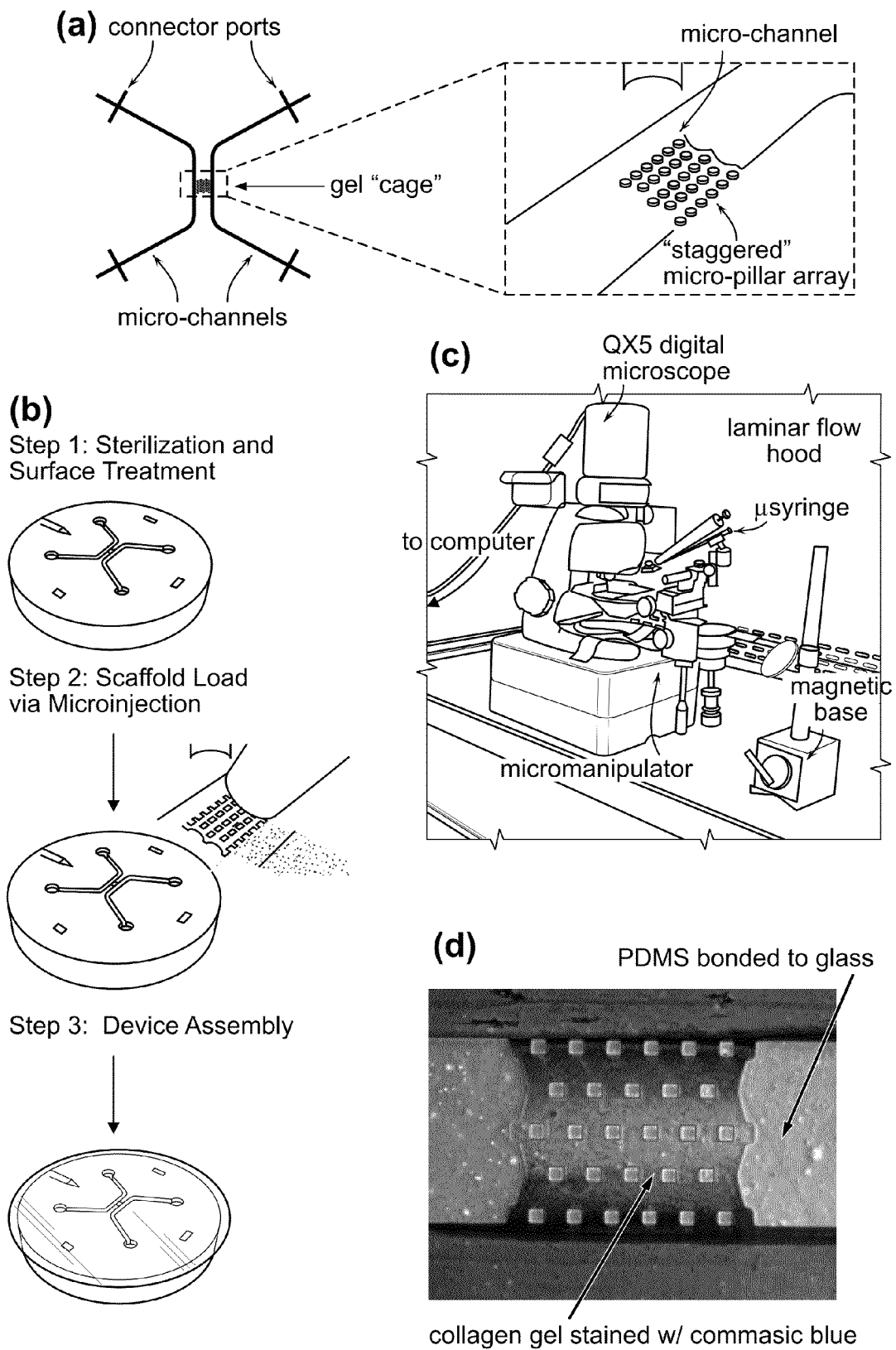
FIG. 14A is a schematic illustration of a portion of a microfluidic device demonstrating a staggered micro-pillar array into which the scaffold is formed.
FIG. 14B is a schematic representation showing the formation of a scaffold and assembly of the microfluidic device.
FIG. 14C is a photograph of a microfluidic device and associated system.
FIG. 14D is a photograph of a portion of a microfluidic device illustrating a scaffold containing collagen that is stained with Coomassie Blue. Fluid-flow paths are shown at the top and bottom of the photograph.
Figure 15:
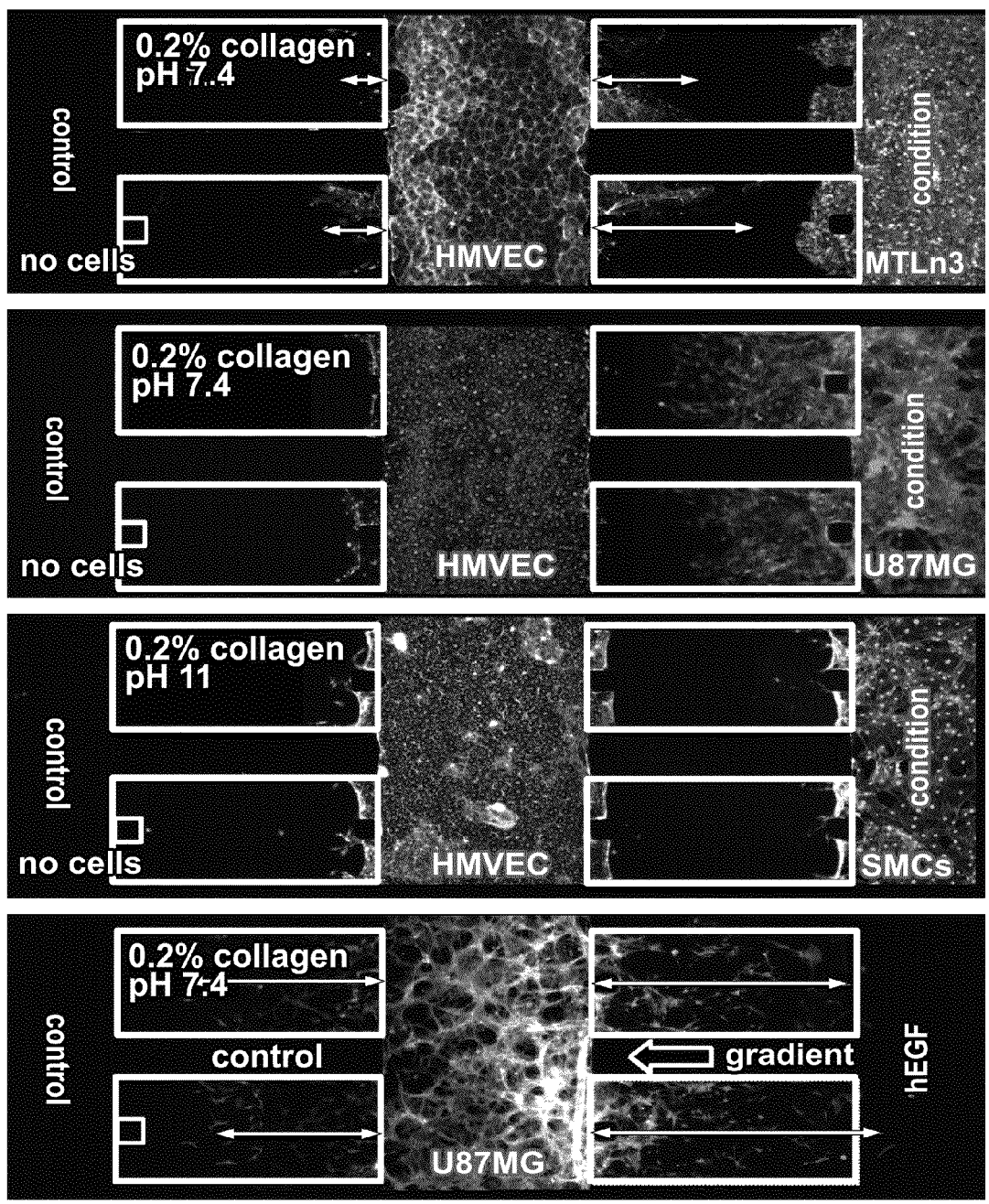
FIG. 15 is a series of photographs of microfluidic devices into which are co-cultured endothelial cells with MTLn3 rat mammary adenocarcinoma cells, U87MG human glioblastoma cells or smooth muscle cells (SMCs).
Figure 16:
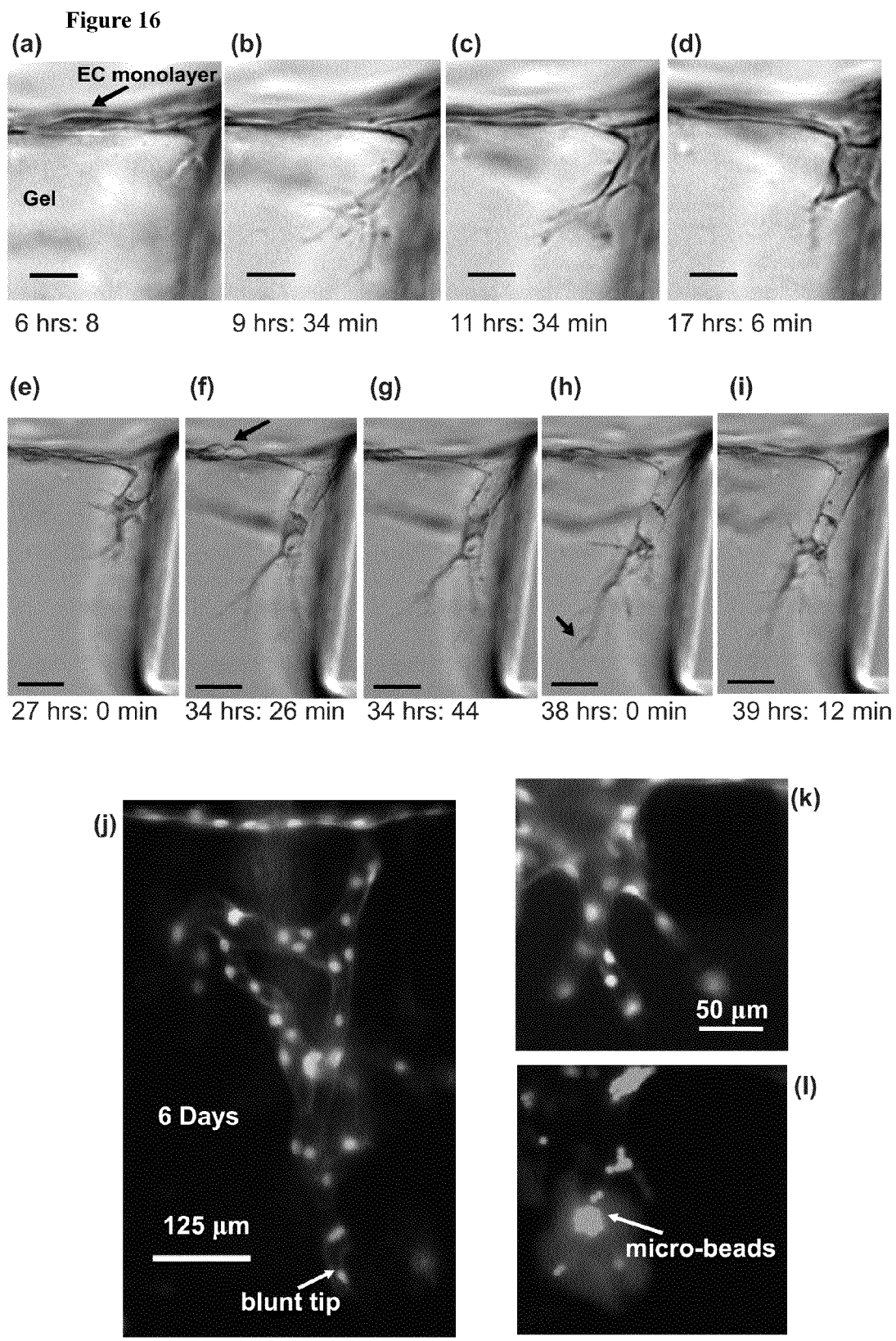
FIGS. 16A-L are a time-lapse series of photographs of endothelial cells that have formed tubules in the scaffold of a microfluidic device.
Figure 17:
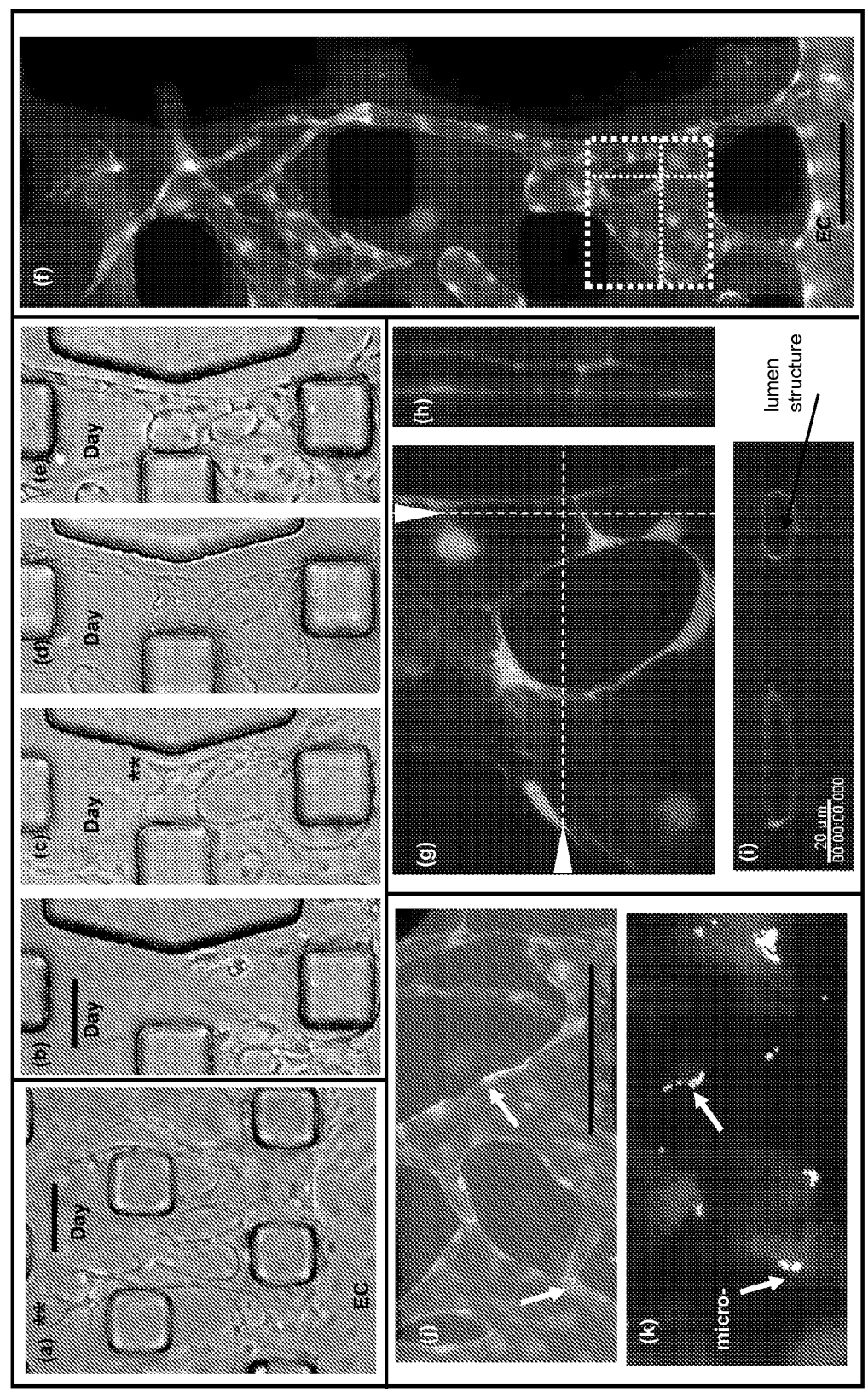
FIGS. 17A-K are a time-lapse series of photographs of endothelial cells that have formed tubules in the scaffold of a microfluidic device.
Figure 18:
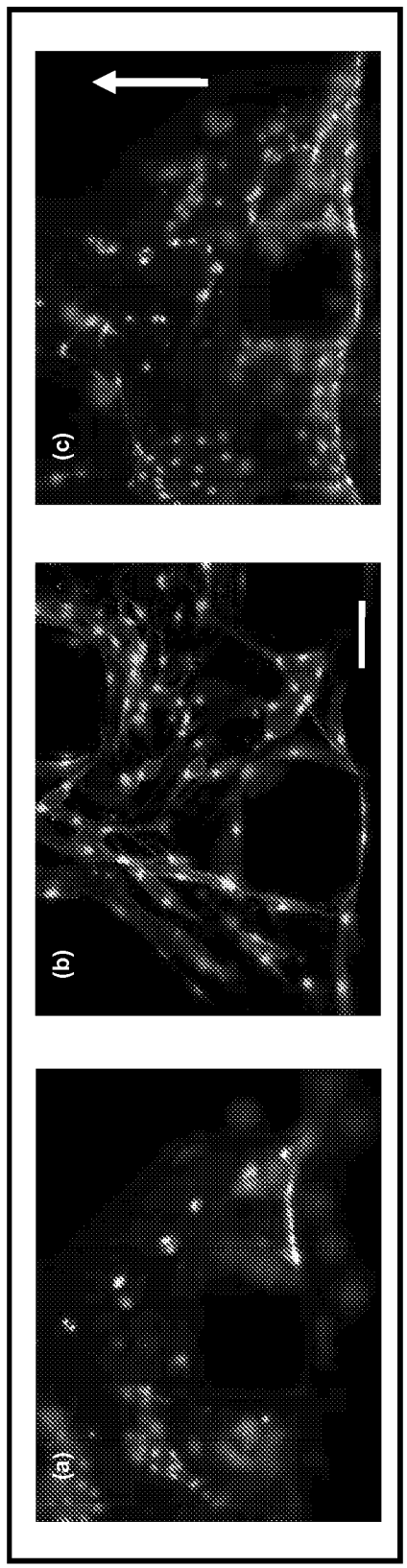
FIGS. 18A-C are a series of photographs of endothelial cells that have formed tubules in the scaffold of a microfluidic device.
Figure 19:
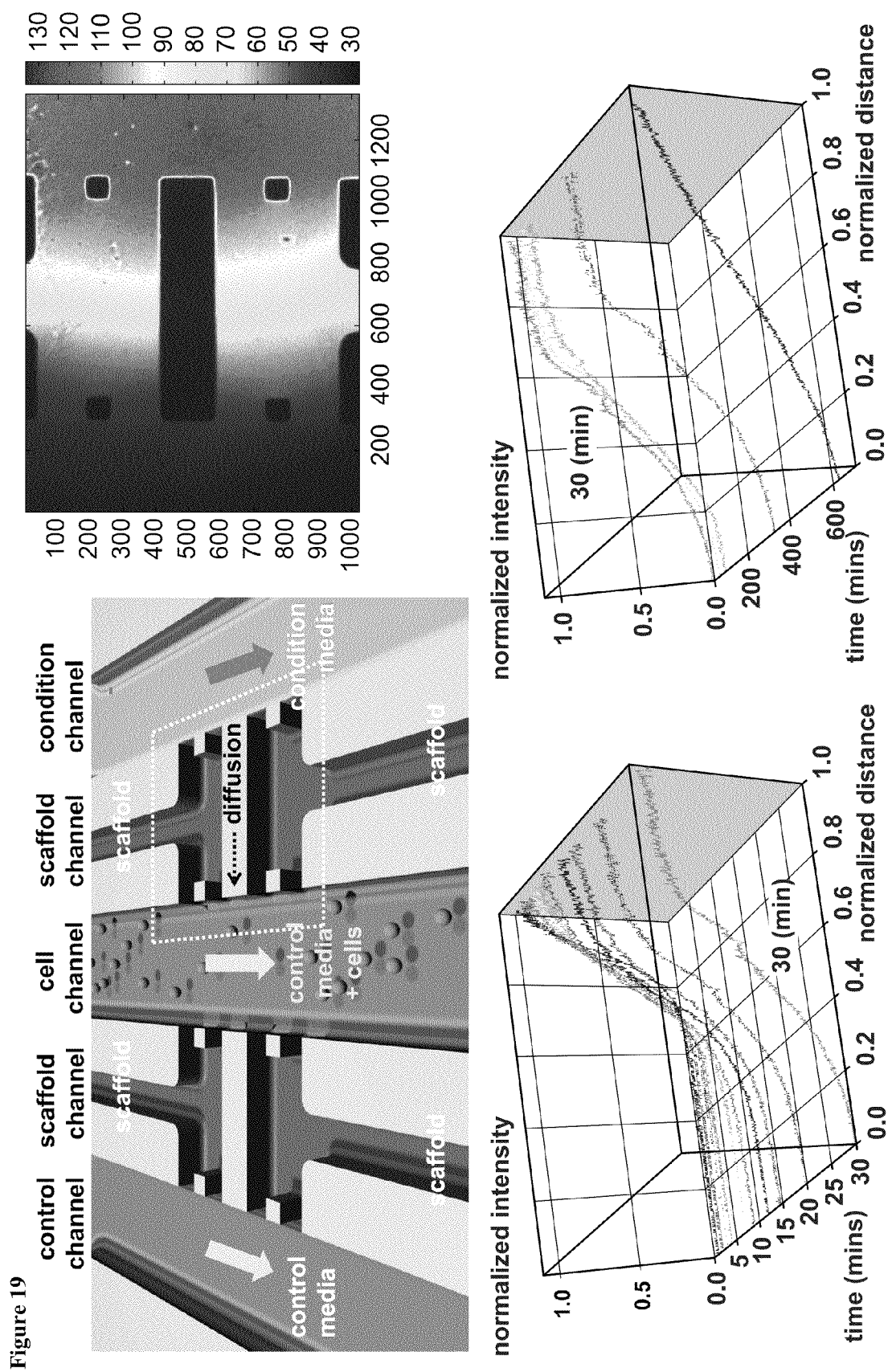
FIG. 19A is a schematic cross-sectional illustration of a portion of a microfluidic device demonstrating multiple (e.g., three) fluid-flow paths and scaffolds.
FIG. 19B is a photograph of a scaffold of a microfluidic device.
FIGS. 19C-D are line graphs showing solute diffusion through scaffolds over time.
Figure 21:
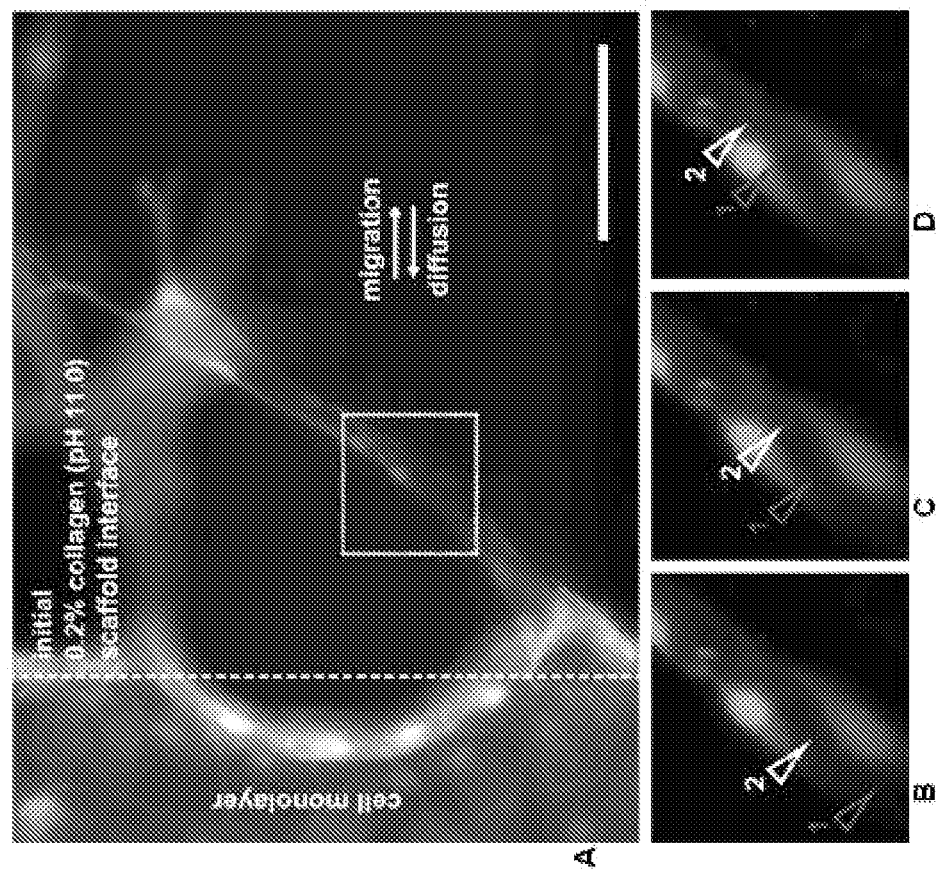
FIGS. 21A-D are a series of photographs showing endothelial cells migrating through a 0.2% collagen scaffold to differentiate into lumen-bearing tubules.
Figure 23:
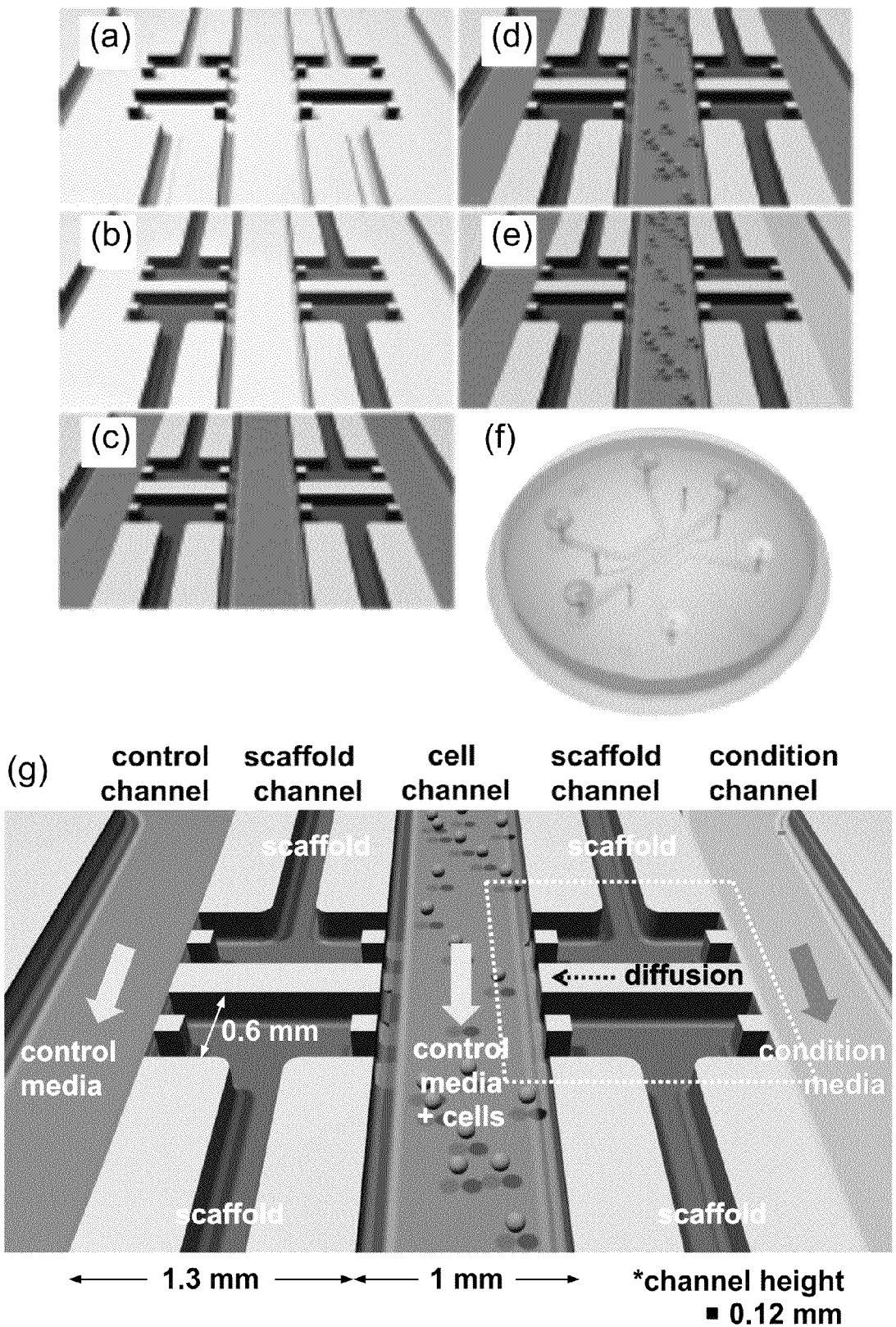
FIG. 23 depicts an experimental protocol for the microfluidic assay development.
Figure 24:
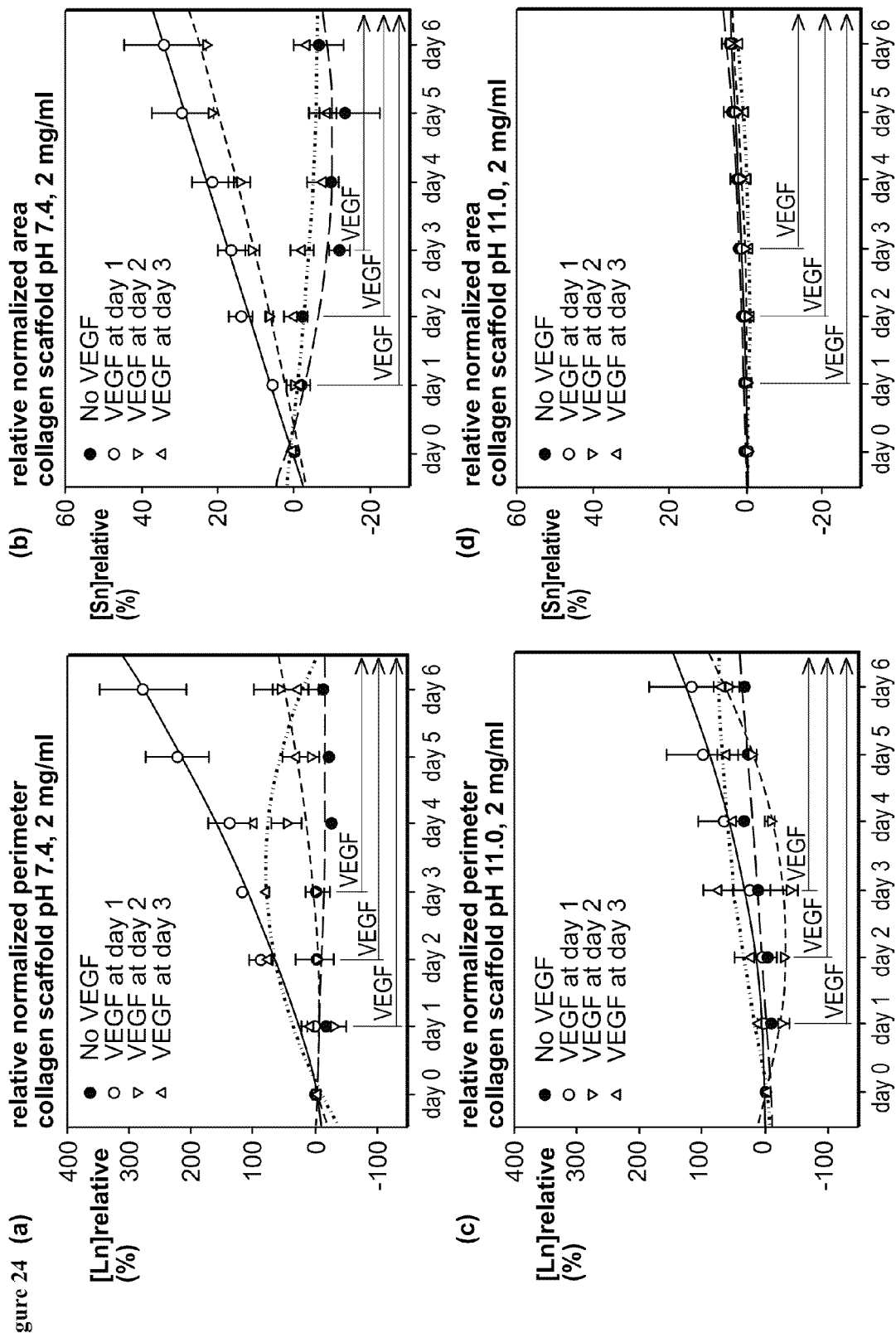
FIG. 24 depicts (a) Graph of normalized relative perimeter of migrated cells in the 0.2% (2.0 mg/mL) collagen gel scaffold polymerized at pH 7.4. 'No VEGF' serves as the negative control without VEGF gradient. 'VEGF at day n' means that VEGF was first applied n days after cell seeding and continued to the end of the experiment. (b) Graph of normalized relative area of migrated cells in the collagen gel scaffold. (c and d) Graphs of normalized relative perimeter and area of migrated cells in the collagen gel scaffold. Each point represents an average with n ¼ 8 (8 scaffolds; 4 devices) for each condition. Error bars represent standard deviation.
Figure 25:
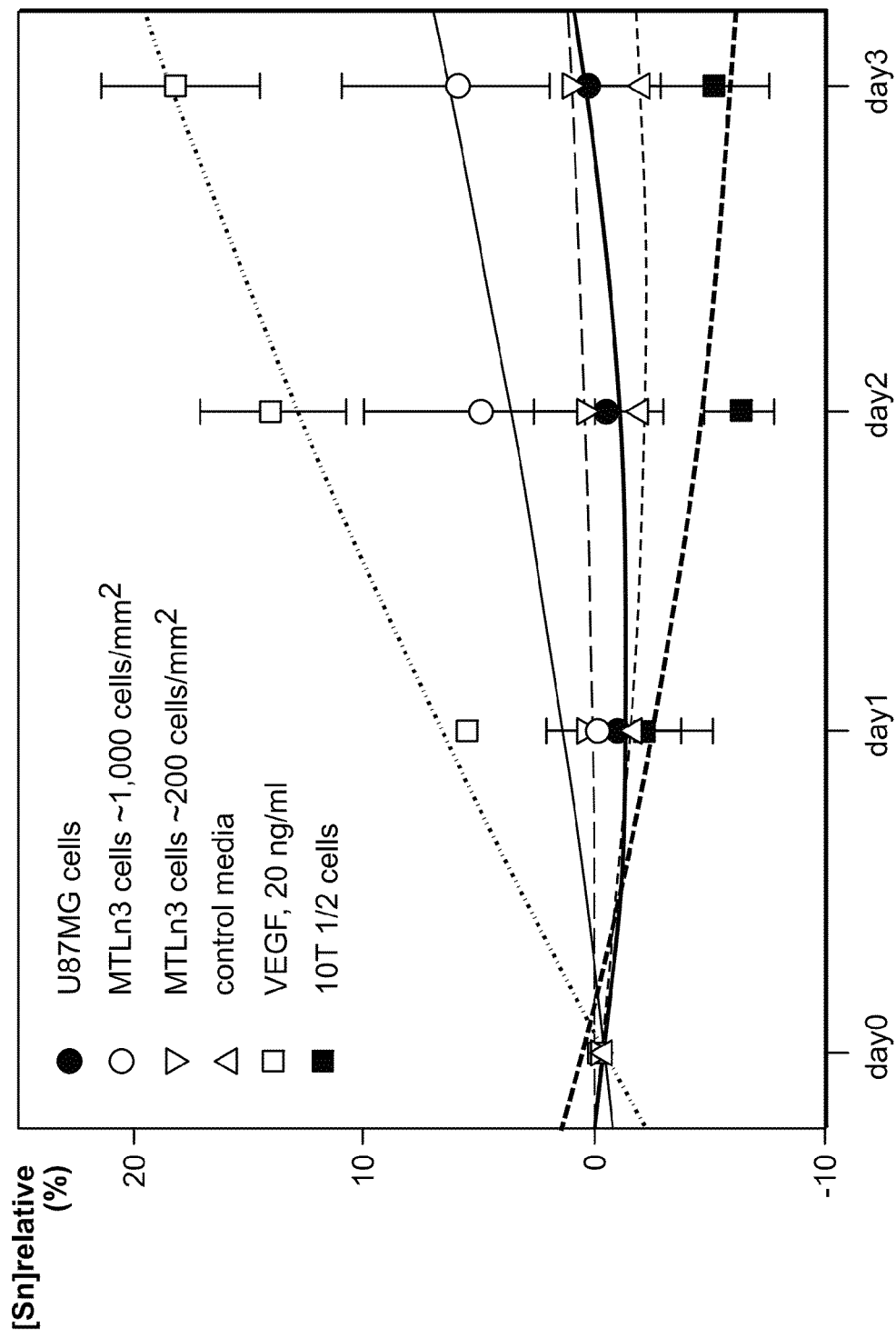
FIG. 25 depicts migration of HMVEC cells in response to signals from other cell types (U87MG, MTLn3, 10T ½) in combination with a VEGF gradient. Change of relative normalized area of HMVEC cultured in the cell channel, with different cell types in the condition channel (U87MG cells, MTLn3 cells with different seeding density and 10T ½ cells), only control media without cells (control media), and control media with 20 ng/mL VEGF (VEGF, 20 ng/mL). VEGF containing medium and MTLn3 cells seeded at high density attracted HMVEC strongly, while low density MTLn3 cells and U87MG cells did not. With 10T ½ cells in the condition channel, HMVEC tended to migrate to the control side. Each point represents an average with n ¼ 8 (8 scaffolds; 4 devices) for each condition. Error bars represent standard deviation.
Figure 28:
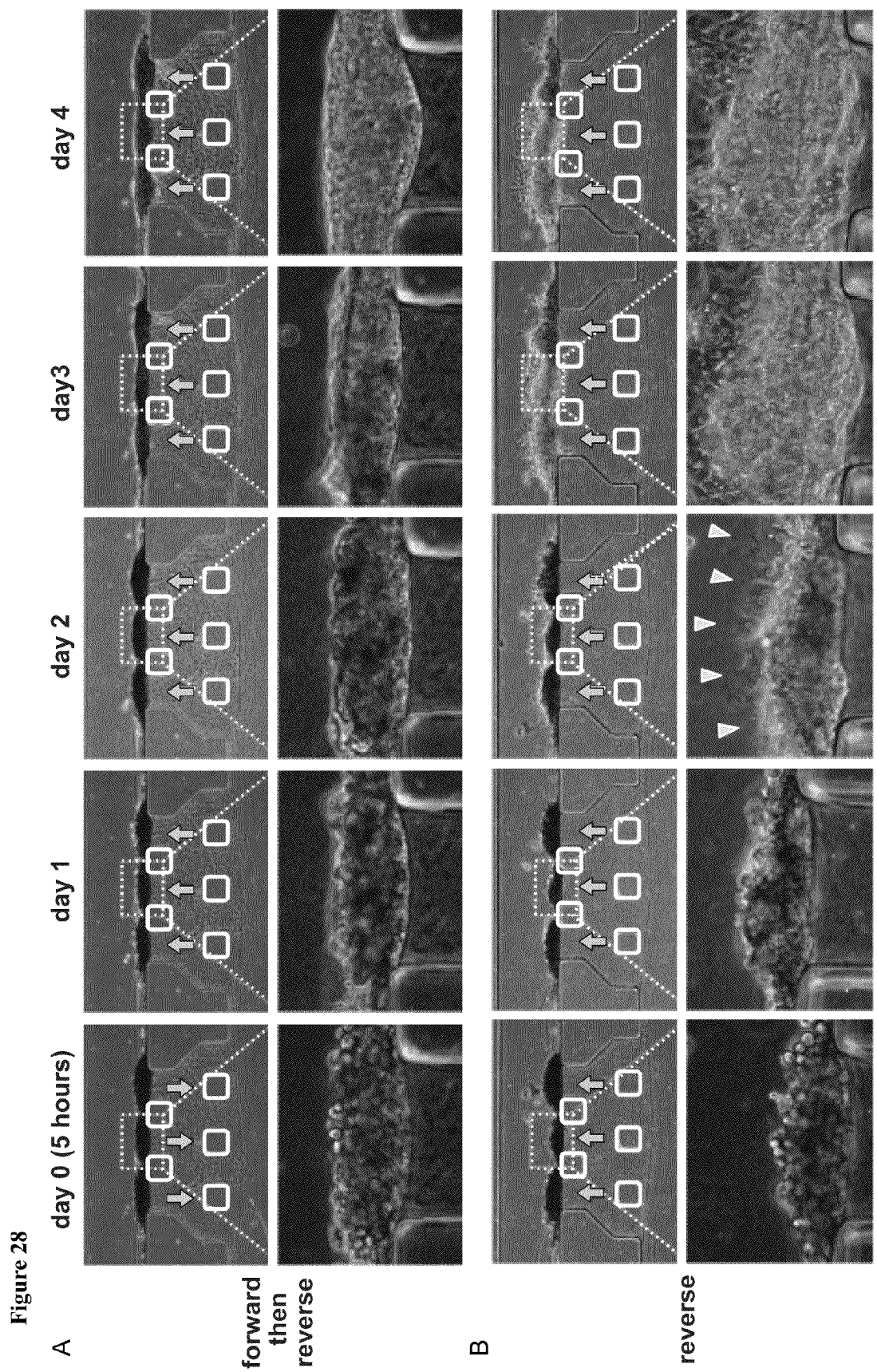
FIG. 28 depicts the effect of interstitial flow direction on the formation of 3D tissue-like structures by hepatocytes. A) Corresponding phase-contrast images of hepatocytes cultured in forward flow (arrows, day 0) followed by reverse flow (arrows, >day 1). Note that hepatocytes gradually organized into 3D tissue-like structures. B) Corresponding phase-contrast images of hepatocytes cultured in reverse flow. Cells started to spread on the microfluidic channel on day 2 (arrowheads, day 2). As cells migrated on the microfluidic channel, cell structures became thin.
Figure 29:
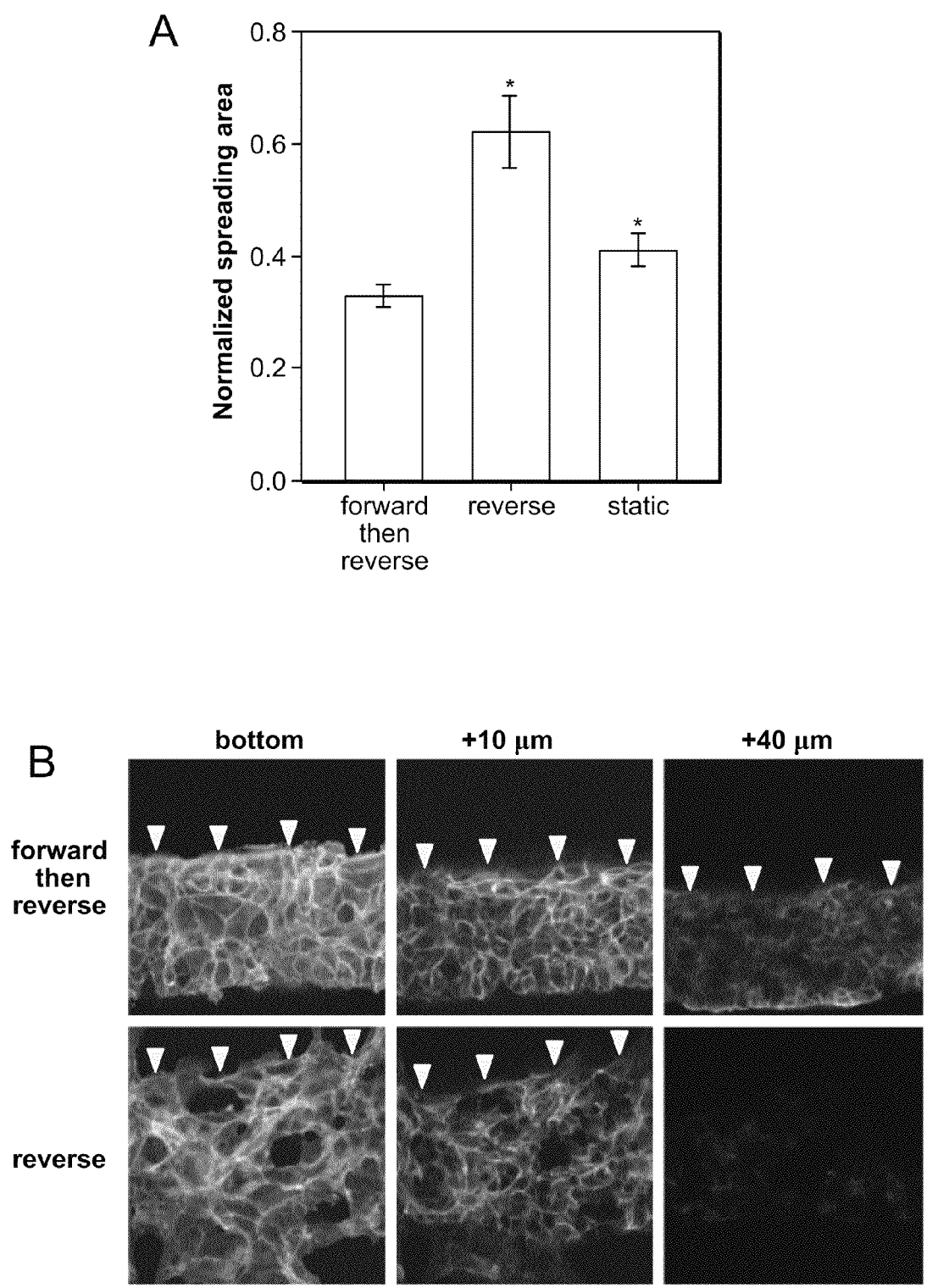
FIG. 29 depicts A) Quantification of hepatocyte morphogenesis on day 3. Area of hepatocytes spreading on the microfluidic channel was measured and normalized by the area of the microfluidic channel. Error bars=$_{SEM}$(n=10, N=3). *P <0.05 vs. forward then reverse. B) Actin filaments were stained, and z-stack images were taken by a confocal laser-scanning microscope at the z-plane of bottom (near coverslip), 10 µm, and 40 µm elevations. Arrowheads indicate edge of hepatocyte tissue-like structures. Cells formed thicker structures in forward flow followed by reverse flow than those in reverse flow alone.
Figure 30:
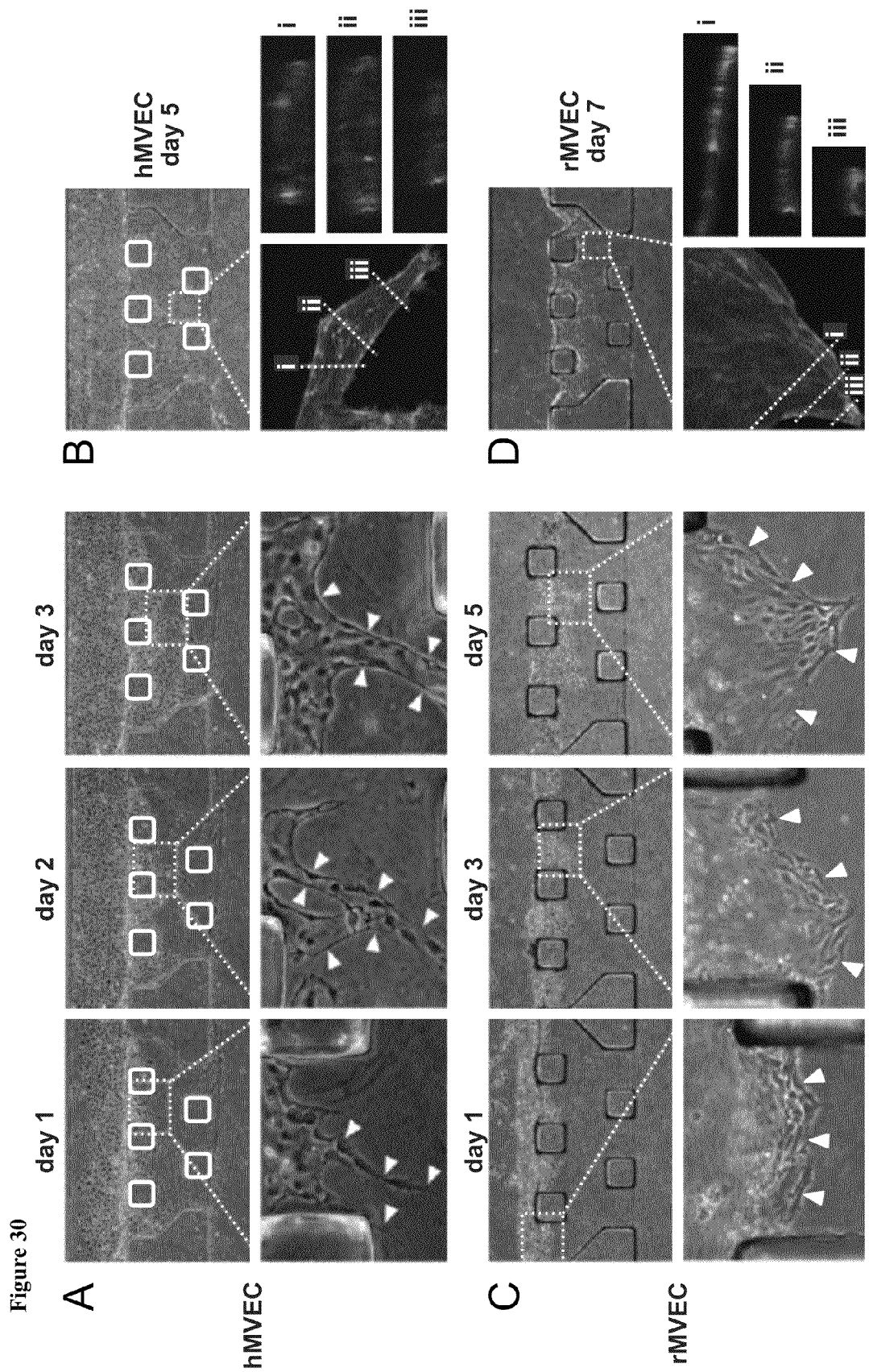
FIG. 30 depicts 3D angiogenesis model created in the microfluidic platform. A) Corresponding phase-contrast images of hMVECs cultured under static conditions. Cells penetrated into the collagen gel scaffold and formed vascular sprouts (arrowheads, day 1). Spouts extended and formed capillary-like structures (arrowheads, days 2 and 3). B) Corresponding phase-contrast and fluorescent images. hMVECs were fixed on day 5 and stained for actin filaments and nuclei. Cross-section images showed that hMVECs formed capillary-like structures with lumens (i, ii), whereas the tip cells formed no lumen (iii). C) Corresponding phase-contrast images of rMVECs cultured under static conditions. Cells migrated into the gel scaffold as a sheet-like structure (arrowheads). D) Corresponding phase-contrast and fluorescent images. rMVECs were fixed on day 7 and stained for actin filaments. Cross-section images showed that the cells formed a sheet-like structure (i-iii).
Figure 31:
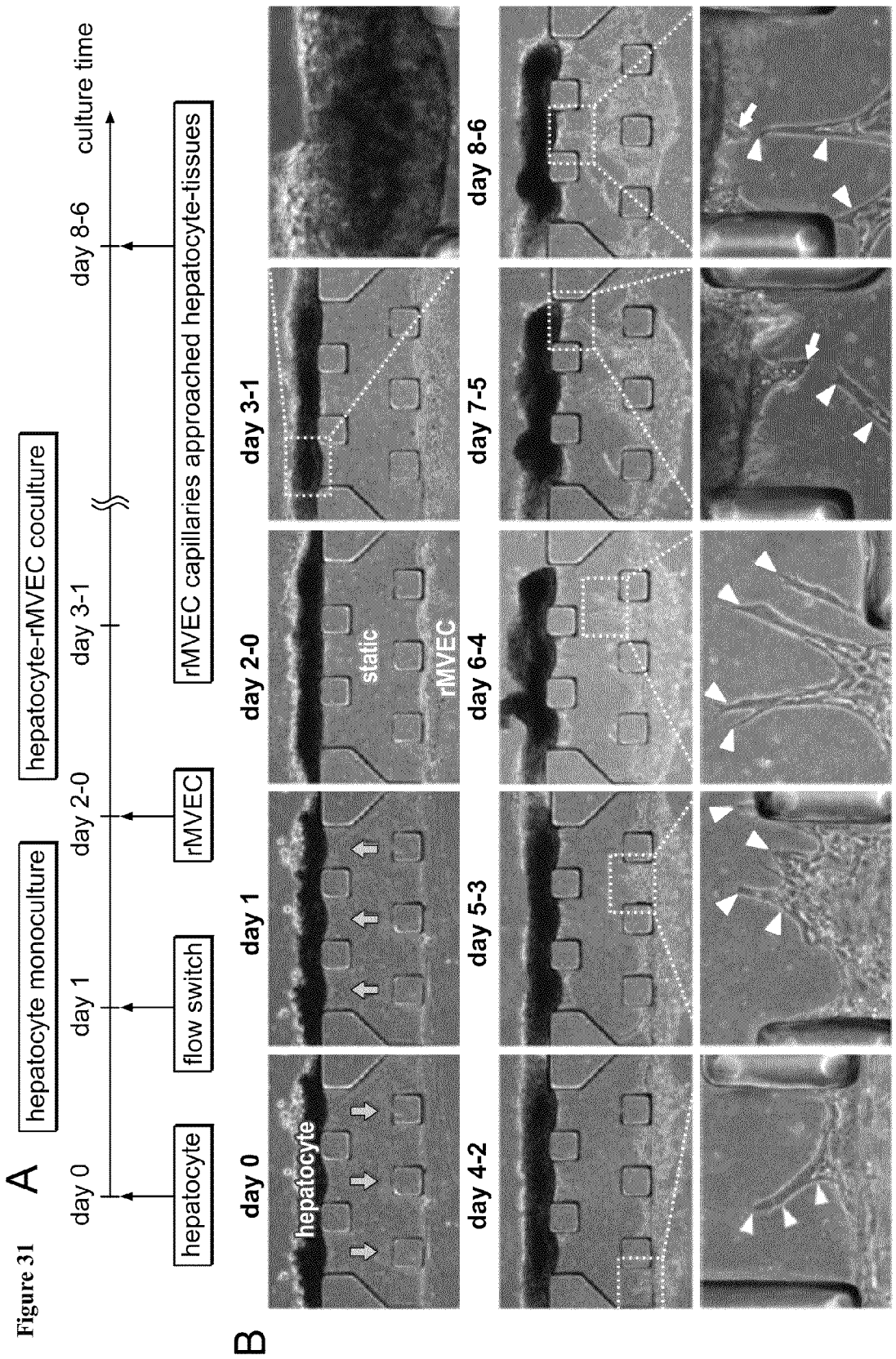
FIG. 31 depicts hepatocyte-rMVEC coculture in the microfluidic platform. A) Experimental protocol for coculture. B) Corresponding phase-contrast images. Hepatocytes were seeded on the sidewall of a collagen gel scaffold, and interstitial flow was applied (arrows, day 0). Flow direction was reversed on day 1 (arrows, day 1). Interstitial flow was stopped and rMVECs were added to the other side of the gel scaffold on day 2 (day 2-0). Hepatocytes formed 3D tissue-like structures (day 3-1). Some rMVECs started to form vascular sprouts on day 4-2 (arrowheads, day 4-2). Vascular sprouts extended across the gel scaffold and approached the hepatocyte tissue-like structures (arrowheads). Some hepatocytes also migrated toward the capillary-like structures of rMVECs (arrows, days 7-5 and 8-6).
Figure 33:
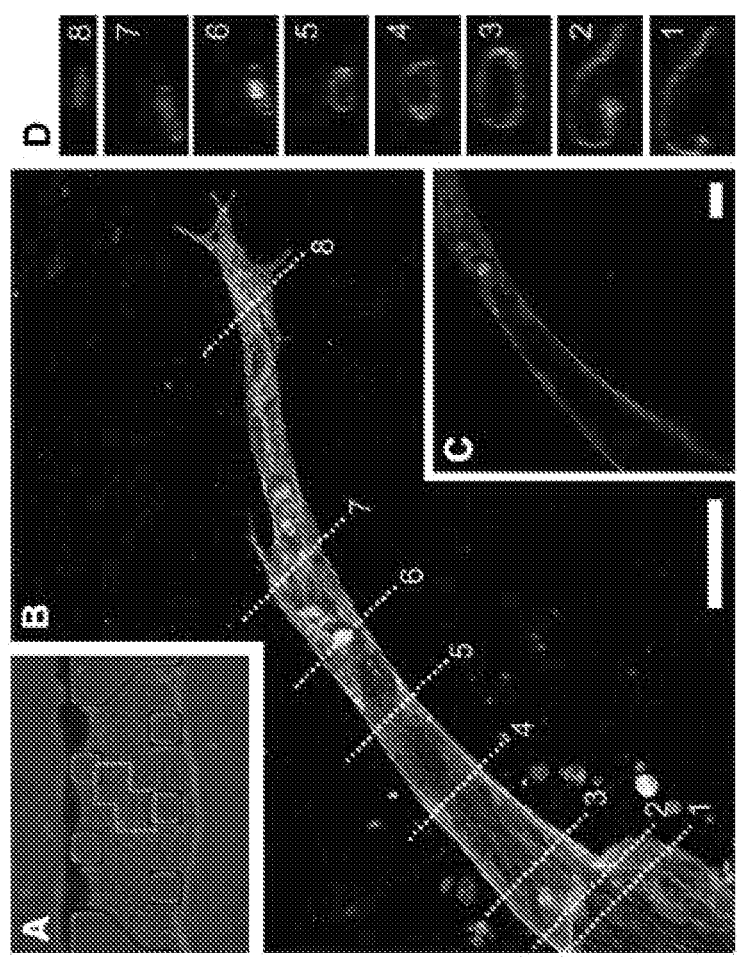
FIG. 33 depicts tube formation process of rMVECs in hepatocyte-rMVEC coculture. A) Phase-contrast image of rMVECs in coculture. B) A z-projection image of a capillary-like structure stained with rhodamine-phalloidin. Cells were cultured under static conditions and fixed on day 12-10 of coculture. Image field corresponds to dotted frame in A. C) Cross-sectional image of capillarylike structures along the direction of the structure. Note that rMVECs formed a luminal structure, although no lumen was found at the tip region. D) Perpendicular cross-sectional images of capillary-like structures in B. Numbers correspond to dotted lines in B. Scale bars=50 µm (B); 20 µm (C).
Figure 34:
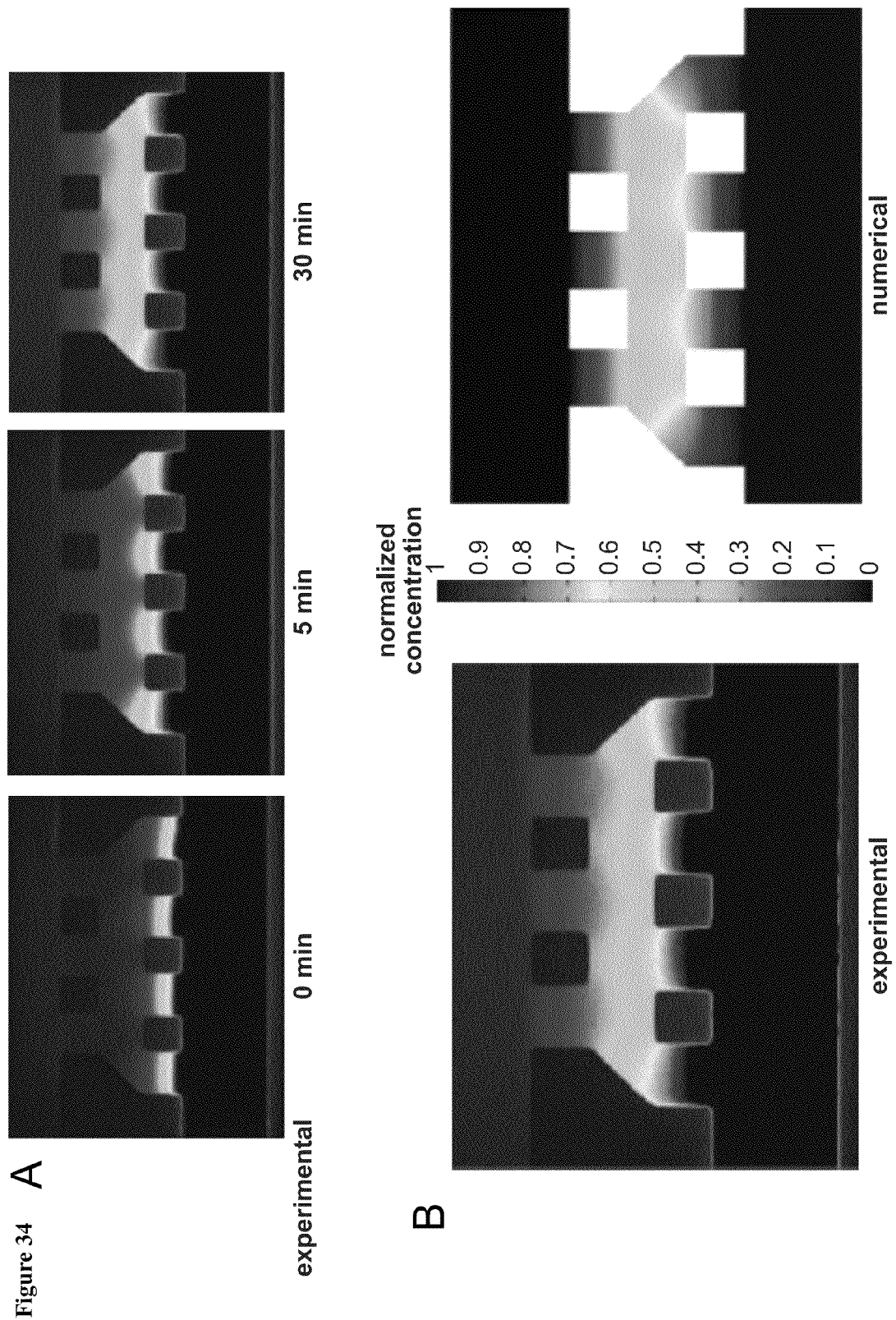
FIG. 34 depicts diffusion analysis in a gel scaffold. A) Distribution of 40-kDa fluorescent dextran across the gel scaffold in the microfluidic platform at 0, 5, and 30 min. B) Experimental results in steady state (left) and corresponding numerical simulation (right). Intensity was normalized to maximum value to compare experimental results with simulations. Images are shown for normalized concentration.

Unless explicitly defined herein, all technical and scientific terms have the same meaning as commonly understood by one of ordinary skill in the arts to which this invention belongs. Where a term is provided in the singular, the inventor also contemplates the plural of that term.

One aspect of the present invention is directed to a device or system, particularly a multi-path microfluidic device. "Microfluidic device," as used herein, refers to a device, apparatus or system including at least one fluid-flow path having a dimension (e.g., height, length or depth) of less than 10 or 5 millimeters (mm). Generally the fluid-flow path will have a width of less than 1 mm. "Fluid-flow path," "fluid path" or "flow path" as used herein, refer to any channel, tube, region, space or pathway or portion thereof through which a fluid, including a liquid or a gas, may pass. A "fluid flow passageway" includes a portion of a fluid-flow path.

In one embodiment, the microfluidic device includes a substrate, where disposed on or in the substrate are at least two fluid-flow paths. The device also includes an optically transparent material that is coupled to the substrate. The device further includes a scaffold that contacts (for example, by filling the space between) the substrate and the optically transparent material, generally within a defined region of the device. This scaffold generally has minimal orthogonal height, length and depth dimensions of at least about 1 μm. As used herein, the phrase "in three dimensional space" refers to having the quality of being three-dimensional, as these dimensions exist in three-dimensional Euclidean geometry. However, non-Euclidean spaces and shapes are also included in the invention. Optionally the device has for each fluid-flow path an inlet to the fluid path, and an outlet from the fluid path.

The substrate is generally a solid material, such as polydimethyl siloxane (PDMS), formed by a soft lithography process, in which the fluid-flow paths are channels in the substrate. Where two fluid-flow paths are present in the same substrate, these fluid-flow paths are substantially parallel along at least part of their lengths. Each fluid-flow path may contain a fluid inlet and a fluid outlet. Fluid inlets are holes, channels or other means for a fluid such as cell culture media to be conducted from outside the device into the fluid-flow path. Fluid outlets are also holes, channels or other means for a fluid such as conditioned or waste cell culture media to be conducted away from the device. One of skill in the art will recognize that other materials used in microfabrication or microfluidics fields are useful in producing the substrate of the invention. For example, a substrate may be formed from or contain silicon, glass, quartz, or plastic (e.g., any synthetic or semi-synthetic polymer having the necessary structural attributes to function as a substrate). Useful plastics are known to those skilled in the art.

The fluid-flow paths can be varied in any dimension (e.g., length, width or depth) so as to produce a desired flow resistance. For example, the flow rate through a flow path can be regulated as a function of the hydrostatic pressure gradient across an inlet and an outlet. One or more fluid-flow paths may function as a resistance channel, meaning that the fluid-flow path has increased resistance to a fluid flow, either continuous or discontinuous (pulsatile) in nature. Resistance channels may contain, for example, tortuous curves or other geometric forms that increase fluid resistivity.

In certain embodiments, the invention provides a microfluidic device containing a pressure regulator. As used herein, a pressure regulator includes any mechanical, chemical or other system that allows for the regulation of one or more characteristics of a flowing fluid (e.g., pressure or volume). A pressure regulator can include one or more valves that create pressure differential between two or more fluid-flow paths.

The scaffold contained within the device separates the fluid-flow paths and provides a multifunctional support upon which cells can migrate, proliferate, or differentiate, depending upon physiological conditions provided in the device. Prokaryotic cells including bacteria are included, as are eukaryotic cells. More than one cell type may be introduced into the scaffold, either concurrently or consecutively. Generally, the scaffold contains a solid or semi-solid biological or biocompatible material (or biomaterial), often which is in the form of a polymer. An advantageous polymer is collagen, which may exist in a monomer-rich solution and be polymerized in situ to form the scaffold. Scaffolds containing collagen or other polymers, and optionally other components, allow the diffusion of biological entities as well as directed migration of bacteria and animal cells. For example, biological entities are cells or sub-cellular components, such as growth factors, cytokines, hormones, antibodies, or enzymes. Growth factors or other biological entities may be distributed uniformly or in controlled gradients in the scaffold, or may be tethered to the scaffold. Scaffolds allow the diffusion of drugs and other small molecules that may interact with cells contained within the fluid-flow paths. The devices described herein are useful for calculating diffusion coefficients of test compounds, in addition to measuring cell monolayer or scaffold permeability of drugs and other compounds.

In certain embodiments, the scaffold may be used to assess the interaction of the scaffold material with a variety of cells. Various scaffold materials may be used. The binding affinity of various biological entities to a variety of scaffold materials may be tested.

In some embodiments, the scaffold contains Matrigel™ (BD Biosciences, San Jose, Calif.). In certain embodiments the scaffold contains or is formed from photocurable polymers, such as dimethacrylate. See Gerecht, et al., Biomaterials 28 (32): 4826-4835 (2007). In certain embodiments, the scaffold contains or is formed from peptides. In certain embodiments the scaffold contains or is formed from a synthetic polymer, such as PEG.

Thus, the microfluidic device can be provided in a form prior to the inclusion of the scaffold. For example, the fluid-flow paths are generated in the substrate by lithography, which also provides a transverse path into which the component(s) of the scaffold are placed, injected, filled or otherwise inserted. When the device includes three or more fluid-flow paths and therefore two or possibly more intervening scaffolds, one, two or more transverse paths are optionally provided in the device. A transverse path may include a fluid inlet, a transverse passageway that extends from the first fluid-flow path to the second fluid-flow path, and a fluid outlet. The transverse paths can be made to control flow in a flow path. For example, a transverse path can function as an integrated valve or pump.

The interior surface of the substrate may be modified prior to forming the scaffold thereon or therein. For example, a coating of poly-D-lysine (PDL) increases the strength of the bond between the scaffold and the substrate. Other modifications to the interior surface of the substrate alter (i.e., either increase or decrease) the hydrophobicity, hydrophilicity, scaffold adhesion properties, or cell affinity of the substrate. In certain embodiments, the interior surface of the substrate is exposed to plasma, thereby increasing the hydrophilicity of the surface of the interior surface of the substrate. In certain embodiments, the interior surface of the substrate is exposed to poly-D-lysine.

The space within the device into which the scaffold will form may also contain one or more "micro-pillars," which are structures formed in the lithography process that improve the mechanical stability of the scaffold. For example, the micro-pillars increase surface tension of the material used to form the scaffold; thus, flow of the scaffold material into the fluid-flow paths is reduced. The presence of multiple micro-pillars in a pattern visually suggests that the scaffold is in the form of a "gel cage." See FIG. 1. The shape of the micro-pillars may be modified to provide better scaffold stability. For example, a hexagonal shape may provide the scaffold material with a stronger surface tension.

The present invention is also directed to methods useful in the analysis of cell behavior. In an embodiment, a method is provided for the measurement of directed migration of a cell in a microfluidic device. Generally a cell is introduced into a first fluid-flow path and may attach to at least one of the surfaces in the flow path. The cell may also adhere to the scaffold. Either at the same time the cell is introduced into the first fluid-flow path or a different time, a biological entity is introduced into a second fluid-flow path. This biological entity may be a cell or sub-cellular component, including growth factors, cytokines, hormones, antibodies, and enzymes, as well as drugs and other small molecules. At a given time point, the extent of the migration of the cell, e.g., into the scaffold and optionally into the second fluid-flow path, is measured. In certain embodiments, an endothelial cell or endothelial cell precursor is introduced into the first fluid-flow path and instead of measuring cell migration, the formation of new blood vessels is measured. The methods of the invention include the diagnosis and characterization of diseases involving altered immune response, as well as the identification of potential therapeutic compounds. For example a neutrophil is introduced into a first fluid-flow path, and a monolayer of endothelial cells is introduced into a second fluid-flow path or the scaffold, either concurrent with or consecutive to the introduction of the neutrophil. The neutrophil is obtained, for example, from a mammalian subject having or at risk of developing an immune disease or disorder (i.e., a test subject), or from a mammalian subject not having or not at risk of developing an immune disease or disorder (i.e., a control subject). Measurement of neutrophil migration dynamics is measured in the device for test subjects and control subjects, and potential therapeutic compounds can be tested for efficacy. In another embodiment, cells are isolated from diabetic and non-diabetic subjects. Also, cells may be obtained from mammalian subjects having cancer, either metastatic or non-metastatic, under conditions such that the metastatic potential of a given subject's cancer can be determined using the devices of the invention. Cells isolated from subjects not having cancer function as control cells.

In certain embodiments, an endothelial cell may be introduced into the first fluid-flow path. A tumor cell may then be introduced into the first fluid-flow path, the second fluid-flow path, or the scaffold. The tumor cell and the endothelial cell may be obtained from the same subject or different subjects. These embodiments enable testing the capacity of a compound or biomolecule to decrease the ability of a tumor cell to pass through the endothelium to enter circulation (intravasate) or exit from circulation (extravasate) or both.

The devices of the invention are also useful in the generation of multiple cell type biomaterials, useful in in vitro and in vivo systems such as tissue engineering. The devices described herein are used to fabricate biological or biocompatible materials that contain two or more types of eukaryotic cells. These devices, containing one or more cell types (e.g., two, three, four or more cell types) are capable of being transplanted or otherwise introduced into a living animal for diagnostic or therapeutic purposes. Further, in vitro systems described herein replicate the physiological functions of tissues or organ systems, and are thus useful in, for example, drug testing or toxicity screening of test compounds.

Exemplary Devices

In certain embodiments, the invention relates to a microfluidic device, comprising:
an optically transparent material;
a substrate coupled to the optically transparent material; and
a scaffold having dimensions of at least 1 µm in three-dimensional space;
wherein
the substrate comprises a post;
the scaffold contacts the substrate, the post, and the optically transparent material;
the substrate comprises a first fluid-flow path and a second fluid-flow path;
the first fluid-flow path does not intersect with the second fluid-flow path; and
the scaffold is disposed between the first fluid-flow path and the second fluid-flow path.

In certain embodiments, the invention relates to any one of the aforementioned devices, wherein the first fluid-flow path and the second fluid-flow path are channels in the substrate.

In certain embodiments, the invention relates to any one of the aforementioned devices, wherein the first fluid-flow path and the second fluid-flow path are substantially parallel.

In certain embodiments, the invention relates to any one of the aforementioned devices, wherein the substrate comprises plastic. In certain embodiments, the invention relates to any one of the aforementioned devices, wherein the substrate comprises PDMS.

In certain embodiments, the invention relates to any one of the aforementioned devices, wherein the substrate is temporarily or permanently modified. In certain embodiments, the invention relates to any one of the aforementioned devices, wherein the modified substrate is a result of exposure of the substrate to poly-D-lysine, exposure of the substrate to plasma, or surface patterning of the substrate. In certain embodiments, the invention relates to any one of the aforementioned devices, wherein the substrate is temporarily modified. In certain embodiments, the invention relates to any one of the aforementioned devices, wherein the substrate is permanently modified. In certain embodiments, the invention relates to any one of the aforementioned devices, wherein the interior surface of the substrate is temporarily or permanently modified.

In certain embodiments, the invention relates to any one of the aforementioned devices, wherein the scaffold comprises a solid or semi-solid biological or biocompatible polymer.

In certain embodiments, the invention relates to any one of the aforementioned devices, wherein the scaffold comprises collagen, agarose, gelatin, fibronectin, fibrin, laminin, or a peptide.

In certain embodiments, the invention relates to any one of the aforementioned devices, wherein the scaffold comprises a photo-curable polymer.

In certain embodiments, the invention relates to any one of the aforementioned devices, wherein the scaffold comprises a first biological entity.

In certain embodiments, the invention relates to any one of the aforementioned devices, wherein the scaffold is substantially adhered to the substrate.

In certain embodiments, the invention relates to any one of the aforementioned devices, further comprising a pressure regulator. In certain embodiments, the invention relates to any one of the aforementioned devices, wherein the pressure regulator is a valve that creates a pressure differential between the first fluid-flow path and the second fluid flow path when fluids are introduced into the fluid-flow paths. In certain embodiments, the invention relates to any one of the aforementioned devices, wherein the pressure regulator is a valve that creates a difference in flow rate between the first fluid-flow path and the second fluid-flow path when fluids are introduced into the fluid flow paths.

In certain embodiments, the invention relates to any one of the aforementioned devices, wherein the first fluid-flow path or the second fluid-flow path comprises a resistance channel.

In certain embodiments, the invention relates to any one of the aforementioned devices, wherein the first fluid-flow path has different dimensions than the second fluid flow path.

In certain embodiments, the invention relates to any one of the aforementioned devices, further comprising a first fluid inlet operably connected to the first fluid-flow path.

In certain embodiments, the invention relates to any one of the aforementioned devices, further comprising a first fluid outlet operably connected to the first fluid-flow path.

In certain embodiments, the invention relates to any one of the aforementioned devices, further comprising a second fluid inlet operably connected to the second fluid-flow path.

In certain embodiments, the invention relates to any one of the aforementioned devices, further comprising a second fluid outlet operably connected to the second fluid-flow path.

In certain embodiments, the invention relates to any one of the aforementioned devices, further comprising a first reservoir operably connected to the first fluid-flow path.

In certain embodiments, the invention relates to any one of the aforementioned devices, further comprising a second reservoir operably connected to the second fluid-flow path.

In certain embodiments, the invention relates to any one of the aforementioned devices, wherein the scaffold comprises a solid or semi-solid biocompatible polymer; and the solid or semi-solid biocompatible polymer allows the passage of a second biological entity. In certain embodiments, the invention relates to any one of the aforementioned devices, wherein the scaffold comprises collagen, agarose, gelatin, fibronectin, fibrin, laminin, or a peptide; and the second biological entity comprises a eukaryotic cell. In certain embodiments, the invention relates to any one of the aforementioned devices, wherein the scaffold comprises collagen; and the second biological entity is selected from the group consisting of a growth factor, a cytokine, a hormone, an antibody, and an enzyme.

In certain embodiments, the invention relates to any one of the aforementioned devices, further comprising a compartment in the substrate, thereby providing an area for the placement of a third biological entity. In certain embodiments, the invention relates to any one of the aforementioned devices, further comprising a compartment in the substrate, thereby providing an area for the placement of tissue or a biopsy specimen.

In certain embodiments, the invention relates to any one of the aforementioned devices, wherein the optically transparent material comprises glass.

In certain embodiments, the invention relates to any one of the aforementioned devices, further comprising a third fluid-flow path, a third fluid inlet, and a third fluid outlet; wherein the third fluid inlet and the third fluid outlet are each operably connected to the third fluid-flow path. In certain embodiments, the invention relates to any one of the aforementioned devices, wherein the scaffold occupies substantially all of the third fluid-flow path.

In certain embodiments, the invention relates to a microfluidic device, comprising:
  an optically transparent material;
  a substrate coupled to the optically transparent material; and
  a scaffold having dimensions of at least 1 μm in three dimensional space;
  wherein
  the substrate comprises a post;
  the scaffold contacts the substrate or the optically transparent material or both; the scaffold contacts the post; the substrate comprises a first fluid-flow path, a second fluid-flow path, and a third fluid-flow path;
  the scaffold comprises a first solid or semi-solid biocompatible polymer disposed between the first fluid-flow path and the second fluid-flow path, and a second solid or semi-solid biocompatible polymer disposed between the second fluid-flow path and the third fluid-flow path; and
  the solid or semi-solid biocompatible polymers allow the passage of one or more biological entities.

In certain embodiments, the invention relates to any one of the aforementioned devices, wherein the scaffold has dimensions at least 2 μm, at least 3 μm, at least 4 μm, at least 5 μm, or at least 10 μm in three dimensional space.

In certain embodiments, the invention relates to any one of the aforementioned devices, wherein the substrate comprises a plurality of posts. In certain embodiments, the invention relates to any one of the aforementioned devices, wherein the substrate comprises a plurality of posts arranged in a regular fashion. In certain embodiments, the invention relates to any one of the aforementioned devices, wherein the substrate comprises a plurality of posts arranged in a random fashion.

In certain embodiments, the invention relates to any one of the aforementioned devices, wherein the post is hexagonal, circular, square, rectangular, or irregular.

In certain embodiments, the invention relates to any one of the aforementioned devices, wherein the dimensions of the post are from about 0.01 μm$^2$ to about 1 mm$^2$. In certain embodiments, the invention relates to any one of the aforementioned devices, wherein the dimensions of the post are about 0.01 μm$^2$, about 0.05 μm$^2$, about 0.1 μm$^2$, about 0.5 μm$^2$, about 1.0 μm$^2$, about 5.0 μm$^2$, about 10.0 μm$^2$, about 25.0 μm$^2$, about 50.0 μm$^2$, about 100 μm$^2$, about 250 μm$^2$, about 500 μm$^2$, about 1000 μm$^2$, about 2500 μm$^2$, about 5,000 μm$^2$, about 10,000 μm$^2$, about 20,000 μm$^2$, about 22,500 μm$^2$, about 25,000 μm$^2$, about 50,000 μm$^2$, about 62,500 μm$^2$, about 75,000 μm$^2$, about 0.1 mm$^2$, about 0.5 mm$^2$, to about 1 mm$^2$.

In certain embodiments, the invention relates to a system for high-throughput analysis, comprising a plurality of any of the aforementioned devices.

In certain embodiments, the invention relates to a method of measuring directed migration of a cell, comprising the steps of:
  a) providing a device comprising:
    i) an optically transparent material coupled to a substrate comprising a first fluid-flow path and a second fluid-flow path; and ii) a scaffold having dimensions of at least 1 μm in three dimensional space that contacts the substrate and the optically transparent material;

b) introducing a cell into the first fluid-flow path;

c) introducing a biological entity into the second fluid-flow path; and d) measuring the directed migration of the cell into the scaffold.

In certain embodiments, the invention relates to any one of the aforementioned methods, wherein the biological entity is selected from the group consisting of prokaryotic cells, eukaryotic cells, growth factors, cytokines, hormones, antibodies, drugs, and enzymes.

In certain embodiments, the invention relates to any one of the aforementioned methods, wherein the cell is a neutrophil, and the biological entity is an endothelial cell.

In certain embodiments, the invention relates to any one of the aforementioned methods, wherein the cell is obtained from a human subject having diabetes, and the biological entity is obtained from a human subject not having diabetes.

In certain embodiments, the invention relates to any one of the aforementioned methods, wherein the cell is obtained from a human subject not having diabetes, and the biological entity is obtained from a human subject having diabetes.

In certain embodiments, the invention relates to any one of the aforementioned methods, wherein the cell is obtained from a human subject having cancer, and the biological entity is obtained from a human subject not having cancer.

In certain embodiments, the invention relates to any one of the aforementioned methods, wherein the cell is obtained from a human subject not having cancer, and the biological entity is obtained from a human subject having cancer.

In certain embodiments, the invention relates to any one of the aforementioned methods, wherein the cell is an endothelial cell; the biological entity is a second cell; the second cell is a tumor cell. In certain embodiments, the invention relates to any one of the aforementioned methods, wherein the cell and the second cell are obtained from the same subject.

In certain embodiments, the invention relates to any one of the aforementioned methods, wherein the biological entity obtained from a human subject having cancer is a single cell, spheroid bodies, or tumor tissue.

In certain embodiments, the invention relates to a method of measuring blood vessel formation, comprising the steps of:

a) providing a device comprising:
  i) an optically transparent material coupled to a substrate comprising a first fluid-flow path and a second fluid-flow path; and
  ii) a scaffold having dimensions of at least 1 μm in three dimensional space that contacts the substrate and the optically transparent material, wherein the scaffold is disposed between the first fluid-flow path and the second fluid-flow path;

b) introducing an endothelial cell or endothelial cell precursor into the first fluid-flow path;

c) introducing a biological entity into the second fluid-flow path; and d) measuring the formation of a blood vessel in the scaffold.

In certain embodiments, the invention relates to any one of the aforementioned methods, wherein the biological entity is selected from the group consisting of prokaryotic cells, eukaryotic cells, growth factors, cytokines, hormones, antibodies, drugs, and enzymes.

In certain embodiments, the invention relates to any one of the aforementioned methods, wherein the device further comprises a third fluid-flow path; and a second scaffold having dimensions of at least 1 μm in three dimensional space that contacts the substrate and the optically transparent material, wherein the second scaffold is disposed between the first fluid-flow path and the third fluid-flow path.

In certain embodiments, the invention relates to any one of the aforementioned methods, further comprising the step of introducing a second biological entity into the first fluid-flow path.

In certain embodiments, the invention relates to any one of the aforementioned methods, wherein the endothelial cell or endothelial cell precursor is introduced as a heterogeneous mixture in a co-culture.

In certain embodiments, the invention relates to any one of the aforementioned methods, further comprising the step of introducing a blood vessel fragment into the first fluid-flow path.

In certain embodiments, the invention relates to a method of measuring permeability, comprising the steps of a) providing a device comprising:
  i) an optically transparent material coupled to a substrate comprising a first fluid-flow path and a second fluid-flow path; and
  ii) a scaffold having dimensions of at least 1 μm in three dimensional space that contacts the substrate and the optically transparent material;

b) introducing a first substance into the first fluid-flow path; and c) measuring the permeability of the first substance into the scaffold.

In certain embodiments, the invention relates to any one of the aforementioned methods, wherein the first substance is a fluid or a small molecule.

In certain embodiments, the invention relates to any one of the aforementioned methods, wherein the scaffold comprises a cell monolayer.

In certain embodiments, the invention relates to any one of the aforementioned methods, wherein the first substance comprises a cell. In certain embodiments, the invention relates to any one of the aforementioned methods, wherein the cell is an endothelial cell.

In certain embodiments, the invention relates to any one of the aforementioned methods, wherein the scaffold comprises a second cell. In certain embodiments, the invention relates to any one of the aforementioned methods, wherein the second cell is a tumor cell.

In certain embodiments, the invention relates to any one of the aforementioned methods, wherein the first substance comprises a cell; the cell is an endothelial cell; the scaffold comprises a second cell; the second cell is a tumor cell; and the endothelial cell and the tumor cell are obtained from the same subject.

In certain embodiments, the invention relates to a method of measuring permeability, comprising the steps of a) providing a device comprising:
  i) an optically transparent material coupled to a substrate comprising a first fluid-flow path and a second fluid-flow path; and
  ii) a scaffold having dimensions of at least 1 μm in three dimensional space that contacts the substrate and the optically transparent material;

b) introducing a first substance into the first fluid-flow path;
c) introducing a second substance into the first fluid-flow path; and
c) measuring the permeability of the second substance into the scaffold.

In certain embodiments, the invention relates to any one of the aforementioned methods, wherein the first substance is a first cell. In certain embodiments, the invention relates to any one of the aforementioned methods, wherein the first cell is an endothelial cell.

In certain embodiments, the invention relates to any one of the aforementioned methods, wherein the second substance is a second cell. In certain embodiments, the invention relates to any one of the aforementioned methods, wherein the second cell is a tumor cell.

In certain embodiments, the invention relates to any one of the aforementioned methods, wherein the first cell and the second cell are obtained from the same subject.

In certain embodiments, the invention relates to a method for evaluating a cell tracking agent, comprising the steps of
a) providing a device comprising:
  i) an optically transparent material coupled to a substrate comprising a first fluid-flow path and a second fluid-flow path; and
  ii) a scaffold having dimensions of at least 1 µm in three dimensional space that contacts the substrate and the optically transparent material;
b) introducing a cell tracking agent into the first fluid-flow path; and
c) measuring the diffusion of the cell tracking agent into the scaffold.

In certain embodiments, the invention relates to any one of the aforementioned methods, further comprising the step of monitoring a parameter. In certain embodiments, the invention relates to any one of the aforementioned methods, further comprising the step of monitoring at least two parameters. In certain embodiments, the invention relates to any one of the aforementioned methods, wherein the parameter is surface shear stress, interstitial flow through the scaffold, gradients in non-reactive solutes, properties of cell-culture scaffold, or properties of a cell in real-time.

In certain embodiments, the invention relates to any one of the aforementioned methods, wherein the device is any one of the aforementioned devices.

In certain embodiments, the invention relates to any one of the aforementioned methods, wherein the scaffold has dimensions at least 2 µm, at least 3 µm, at least 4 µm, at least 5 µm, or at least 10 µm in three dimensional space.

In certain embodiments, the invention relates to a method of fabricating a device, comprising the steps of:
a) contacting a liquid scaffold material with a substrate comprising a first fluid-flow path, a second fluid-flow path, and a post; and
b) operably connecting to the substrate an optically transparent material.

In certain embodiments, the invention relates to any one of the aforementioned methods, wherein the device is any one of the aforementioned devices.

In certain embodiments, the invention relates to any one of the aforementioned methods, wherein the liquid scaffold material comprises monomeric collagen.

In certain embodiments, the invention relates to any one of the aforementioned methods, further comprising the step of modifying the substrate before contacting the substrate with the liquid scaffold material, thereby altering the hydrophobicity, hydrophilicity, cell affinity, or scaffold adhesion properties of the substrate. In certain embodiments, the invention relates to any one of the aforementioned methods, wherein the step of modifying the substrate comprises exposing the substrate to poly-D-lysine, exposing the substrate to plasma, or patterning the substrate. In certain embodiments, the invention relates to any one of the aforementioned methods, wherein the substrate is temporarily or permanently modified before contacting the substrate with the liquid scaffold material, thereby temporarily or permanently altering the hydrophobicity, hydrophilicity, cell affinity, or scaffold adhesion properties of the substrate. In certain embodiments, the invention relates to any one of the aforementioned methods, wherein the substrate is temporarily modified before contacting the substrate with the liquid scaffold material, thereby temporarily altering the hydrophobicity, hydrophilicity, cell affinity, or scaffold adhesion properties of the substrate. In certain embodiments, the invention relates to any one of the aforementioned methods, wherein the substrate is permanently modified before contacting the substrate with the liquid scaffold material, thereby permanently altering the hydrophobicity, hydrophilicity, cell affinity, or scaffold adhesion properties of the substrate. In certain embodiments, the invention relates to any one of the aforementioned methods, wherein the interior surface of the substrate is modified.

In certain embodiments, the invention relates to any one of the aforementioned methods, wherein the step of contacting the liquid scaffold material with the substrate comprises injecting the liquid scaffold material under pressure into a defined region of the substrate that is substantially non-contiguous with the first and second fluid-flow paths.

In certain embodiments, the invention relates to any one of the aforementioned methods, wherein the step of contacting the liquid scaffold material with the substrate comprises microinjection of the liquid scaffold material.

In certain embodiments, the invention relates to any one of the aforementioned methods, wherein the step of contacting the liquid scaffold material with the substrate comprises introduction of the liquid scaffold material into the first fluid-flow path or the second fluid-flow path.

In certain embodiments, the invention relates to any one of the aforementioned methods, wherein the scaffold has dimensions of at least 1 µm, at least 2 µm, at least 3 µm, at least 4 µm, at least 5 µm, or at least 10 µm in three dimensional space.

EXEMPLIFICATION

The invention, having been generally described, may be more readily understood by reference to the following examples, which are included merely for purposes of illustration of certain aspects and embodiments of the present invention, and are not intended to limit the invention in any way. All headings are for the convenience of the reader and should not be used to limit the meaning of the text that follows the heading, unless so specified.

Example 1

Microfluidic Device Fabrication and Surface Modification

The design of the microfluidic network was created in AutoCAD® software (Autodesk, San Rafael, Calif.) with the dimensions of the microfluidic fluid-flow paths (or "channels"), gel "cage" and micro-pillars as provided in Table 1.

| Channel width | Channel height | Gel cage dimension | Gel cage height |
|---|---|---|---|
| 500 µm-1 mm | 50-300 µm; or 100-200 µm | Approximately 450-1000 µm wide by 450-1000 µm long | 50-300 µm; or 100-200 µm |

One of skill in the art will recognize that dimensions and shapes of each component of the device can be specified for a given application. The channel width and height could independently be several microns (µm) to several mm, and can be rectangular, circular or various other shapes capable of being fabricated. The dimensions of the gel cage can be specified from several µm or less to several mm or greater, including or in addition to posts, pillars, or other structures. Pillar size may range from µm or less to several mm or greater (such as 100 µm, 150 µm, or 250 µm, and are fabricated as rectangular, circular or other shapes). The height of the gel cage may be equal to, greater than, or less than the height of a given channel. The scaffold may also contain one or more microfluidic channels.

A transparency mask was created from the CAD file with a minimum geometric feature size of approximately several 100 µm and printed by a high-resolution printer (PageWorks, MA). Other types of masks are phase-shift masks, and immersion photolithography immersion, as well as MoSi and Ta/SiO$_2$ masks. This transparency mask was used in photolithography of SU-8 photoresist to create a silicon wafer master. Microfluidic devices were made by replica molding[18] poly dimethyl siloxane (PDMS) (Dow Corning, USA) and curing the degassed elastomer mix (10:1, base: curing agent) against the silicon master in an 80° C. oven for 2 hours. PDMS is biocompatible and has excellent optical transparency. Polymerized PDMS apparatuses were peeled off the silicon master, individual bioreactor apparatuses (35-mm diameter, 0.8-1 cm height) cut out and inlets and outlets cored down to individual fluid-flow paths using a sharpened flat-ended 16-gauge needle. Prior to cell culture PDMS apparatuses were cleaned and sterilized at 120° C. for 20 minutes in a wet cycle followed by a dry cycle at 120° C. for 35 minutes (20 min sterilization/15 min dry). Next, the PDMS surface was rendered hydrophilic by exposure to air plasma to facilitate scaffold formation. Sterilized devices were placed on trays in plasma cleaner (Harrick, Calif.) chamber (pattern side up). A pump-down cycle (~2 minutes) was initiated followed by irradiation for 2 minutes with pink plasma. Surface treated apparatuses were stored in a sterile container and used within 0.5-2 h following plasma treatment. Following polymerization flat PDMS surfaces are hydrophobic and may exhibit poor wetability; scaffold injection into untreated PDMS apparatuses often resulted in gels that exuded into the fluid-flow paths and often did not fill the gel cage, resulting in small bubbles adjacent to the micro-pillars. The hydrophobicity of PDMS is tunable and PDMS surfaces can be temporarily rendered hydrophilic by exposure to air plasma[19]. Subsequent to plasma treatment, hydrophobic recovery time is dependent upon the method of preparation and storage. For example, thermal aging, longer oxidation time and storage in nitrogen are effective in delaying the recovery of hydrophobicity[20]. Here, PDMS was surface treated with air plasma for 2 minutes, longer than is typically required for immediate bonding to glass. To maintain the seal when connected to macro-scale plumbing, typical microfluidic devices are permanently bonded or vacuum sealed[21] to glass or a layer of PDMS to prevent leaks. However, it was determined that the plasma treatment used to contain scaffold spreading and filling was sufficient to promote bonding to glass and therefore no further adhesive steps were required.

Example 2

Formation of a Scaffold in a Microfluidic Device

A microinjection station was created to load the cell culture scaffold (sub µL volumes) into the device under aseptic conditions. The system components included a manual micromanipulator (MN-151 Joystick Micromanipulator with H-7 Pipette Holder, NARISHIGE, NY), microliter syringe (Hamilton, 62RNR, 2.5 µL SYR, 22s/2"/3, VWR), digital microscope (Big Blue QX5, COMPUVISOR.COM, TX) (all housed in a laminar flow hood) and a monitor for visual guidance. The MN-151 joystick feature provided control of micro-scale adjustment in the XY plane with additional coarse adjustments along the X, Y and Z axes.

Scaffold Microinjection. Sterilized PDMS devices with their surfaces rendered hydrophilic as described above are positioned on the microscope stage (patterned surface upward) with the "gel cage" in clear view on the video monitor. The tip of the microliter syringe (pre-loaded with pre-polymer solution), attached to the micromanipulator, is positioned a few microns above of the "gel cage" and a small droplet of the pre-polymer solution is created manually and lowered until the droplet first makes contact with the micro-pillars. Droplet size is controlled such that its diameter is approximately equal to half the width of the gel cage. Small droplets are created just above the gel cage, lowered and dispensed; this process is repeated until the gel cage is full.

Scaffold Loading and Device Assembly. Gel pre-polymer solution (collagen type I, rat tail in these experiments) is microinjected into the gel cage; fluidic channels are sealed with a clean glass cover slip (35 mm, VWR) and secured with a mechanical clamp. This is repeated for multiple apparatuses at a time. After scaffold injection, assembled PDMS apparatuses are placed in a secondary humidified container, to prevent the gels from drying out. Gels are allowed to polymerize for 30 min at 37° C. in a humidified incubator.

Demonstration of the formation of a gradient across a scaffold. Following polymerization of a scaffold containing collagen, fluid-flow paths were filled with cell culture media (without supplements). Gradient studies were performed under static conditions with the media in one flow path replaced by a dilute solution of fluorescent dextran (40 kDa, Invitrogen) at an initial concentration of 20 µg mL$^{-1}$. Fluorescent intensity was visualized with a Nikon TE300 microscope (Nikon Instruments Inc., NY). A series of fluorescent images (4× magnification) of the gel region were acquired with a Hamamatsu camera (Hamamatsu, Japan) using Openlab (Improvision, MA) data acquisition software and stored for further analysis. Images were processed to obtain the changes in fluorescent intensity across the gel at each time point. Image processing of time-lapse fluorescent images was performed using a custom written MATLAB (MathWorks, MA) code. Briefly, each fluorescent image of the gel region was divided into rectangular sections that excluded the PDMS micro-pillars. Pixel intensities and corresponding location from the "source" channel were recorded for these rectangular sections. Average fluorescent intensities were calculated for pixels at the same distances from the dextran channel for all pixels across the length of the gel. At each time point a plot of the normalized average intensity profile across the gel was generated. Experimental diffusion curves were fitted to theoretical curves obtained from a finite element model generated in FEMLAB (Comsol, USA).

A typical time course of the concentration profile in the gel cage following the introduction of a fluorescent dextran to one channel is shown in FIG. 11A. Normalized florescence intensity $(C-C_{min})/(C_{max}-C_{min})$ in the gel is plotted as a function of normalized distance $(x/x_{max})$ from the dextran (40 kDa) "source" fluid path. A steady state concentration profile was reached within 40 minutes. In this study, 40 kDa dextran was chosen because it is similar in size to several growth factors of interest including VEGF, bFGF and IGF[22].

The steady state experimental data were compared to results from a finite element model assuming a diffusion coefficient of $1\times10^{-6}$ cm$^2$ s$^{-1}$. This value agrees well with the range of values reported in the literature[23,24]. The ability to generate gradients of soluble factors across a three-dimensional matrix provides the potential to simulate physiologically relevant mechanisms during directional migration including sprouting angiogenesis, tumor metastasis and immune response. The dynamic motility of migratory cells can be probed in a controlled microenvironment and monitored in real-time. In addition, the spatial and temporal presentation of such factors provides another level of control which would be physiologically relevant but not possible in most current systems, although one group has demonstrated the ability to generate concentration gradients in a microfluidic ladder chamber[25].

Example 3

Study of Capillary Morphogenesis in a Dual Fluid-flow Path Device

Description of device and scaffold formation. A dual fluid-flow path device was fabricated from PDMS using standard soft lithography and replica molding techniques as described herein. The device contains of two parallel flow paths and a central "gel cage" transverse path to contain an injectable biologically-derived or synthetic scaffold (here, a soft hydrogel) for cell culture. Using the device as described herein, one is able to control (1) surface shear stress, (2) interstitial flow through the matrix (3) gradients in chemoattractants or chemorepellants, (4) properties of the scaffold, (5) simultaneously monitor cells in real-time, and (6) effects of co-cultured cells.

A staggered array of micro-pillars was incorporated into the gel cage to provide mechanical stabilization for the scaffolds, allowing the scaffold to sustain pressure differentials in excess of several centimeters (cm) of water. With the scaffold in place the two flow paths are essentially isolated from each other in that no liquid can move between the two flow paths; however, the diffusion or convection of soluble factors through the porous scaffold from one flow path to the other is not restrained. All cell cultures were maintained in a humidified incubator at 5% $CO_2$ and 37° C. Human adult dermal microvascular endothelial cells (HMVEC-ad, LONZA, USA) were propagated in EGM-2MV media system with 5% fetal bovine serum. Cells were expanded on collagen-coated flasks and used at passages 6-8. Cells well suspended at $1\times10^6$ cells mL$^{-1}$ in ice-cold liquid type I rat tail collagen with a final gel concentration of 2 mg mL$^{-1}$. Liquid collagen was prepared by adding collagen stock solution to a mixture of 10×PBS, 1 M NaOH and tissue culture grade water to obtain a 2.5 mg mL$^{-1}$ solution. A predetermined volume of high density cell suspension was then mixed with the collagen solution to obtain the required seeding density. The collagen/cell mixture was loaded in a microliter syringe and gels cast as described herein. The microinjection protocol provided the ability to load minute volumes of scaffold material, with or without cells, directly in the designated space. Alternatively, perfusion loading of the scaffold is provided. Following gelation, fluid-flow paths were filled with cell culture medium and incubated for 24 hours. To demonstrate the effects of biochemical factors, cells were cultured under static conditions with complete media (control) or media enriched with pro-angiogenic factors (bFGF, VEGF and PMA all at 50 ng mL$^{-1}$). Cells maintained in cultures for several days in complete media or media supplemented with bFGF/VEGF/PMA cocktail which were replenished at 24 hour time points. Samples were fixed, tagged with fluorescent markers and imaged.

Surface shear stress on 3D encapsulated cells. To demonstrate the effect of biophysical stimuli, cells were subjected to small levels of surface shear stress. Devices with endothelial cells on the surface of the scaffold were formed and a pressure differential (50 Pa) was imposed across the scaffold by varying the difference in the height of culture media in the reservoir columns.

Endothelial cell monolayer formation. Two different cell seeding protocols were used to control the substrate on which endothelial cells initially formed confluent monolayers, namely 2D and 3D substrate monolayer seeding. Collagen gel scaffolds were formed as previously described. Following gelation, fluid-flow paths were filled with a 2 mg mL$^{-1}$ fibronectin coating solution and incubated overnight. Prior to cell seeding the coating solution was replaced with complete media and equilibrated for another 2-4 hours. A cell suspension of 2-3×10$^6$ cells mL$^{-1}$ was flowed into one fluid-flow path and the cells permitted to adhere to the rigid glass or compliant scaffold surface as they settle out of suspension by gravity. Endothelial cells were cultured for 24-48 hours on the rigid (2D monolayer seeding) or compliant (3D monolayer seeding) surfaces before further treatment. Pro-angiogenic factors were either presented as a gradient or at uniform concentration. For this assay VEGF (10-50 ng mL$^{-1}$) and S1P (250 nM) were used to promote morphogenesis.

Characterization of capillary morphogenesis and tube-like structures. The primary mechanism by which new blood vessels or capillaries are formed in vivo, angiogenesis[26], involves a series of well-delineated steps including matrix degradation, cell migration, proliferation and lumen formation. This is a tightly regulated process that is affected by metabolic stress[27,28], mechanical stresses[29-31], soluble factors[32] and ECM matrix components[33,34]. Phase-contrast, epifluoresence and confocal microscopy were used to characterize capillary morphogenesis and the three-dimensional morphology of endothelial cell structures. Fluorescent and phase contrast images were acquired on Nikon TE300 microscope equipped with a Hamamatsu camera and Openlab image acquisition software. Time-lapse images were taken of live samples every 12-24 hours with phase contrast microscopy. Samples were fixed with 4.0% paraformaldehyde (PFA) and tagged with a fluorescent marker for actin cytoskeleton and cell nuclei. Confocal images were collected using spinning disk confocal microscope (Zeiss Axiovert 200M) furnished with Imaging Suite (PerkinsElmer Life Science) acquisition software. A series of 100 optical serial sections (1 μm thick) were obtained. The aligned images were stacked and rendered for 3D visualization using Imaris (Bitplane, MN). HMVEC-ad were cultured until sub-confluence on a collagen coated flask in EGM-2MV complete media, harvested and subsequently cultured in a microfluidic device. HMVEC-ad remain viable for a period of several days. Within a few hours following cell seeding endothelial cells form a monolayer on collagen gels.

Time-lapse movies were made to demonstrate the capability of the microfluidic devices to characterize and study cellular mechanisms during sprout formation. In traditional sprouting models this capability is limited, since cells are viewed through a monolayer. Using microfluidic devices of the present invention, the directional sprouting and migration occur in the microscopic viewing plane. Time-lapse imaging shows a "lead-cell" as it invades the underlying 3D collagen matrix. In case of single sprout formation; the lead-cell extends filopodial projections into the underlying matrix while the neighboring endothelial cells on the monolayer remain non-invasive. Cell invasion follows a period of dynamic projection and retraction of filopodia while maintaining contact with the monolayer and remain highly polarized. An initial root-like structure is formed in the direction of migration that persists for several minutes with more dynamic smaller extensions. Subsequent morphological changes included increased penetration depth, filopodial diameter and translocation of cell from monolayer (evident by movement of nucleus) followed by conical structure (onset of lumen formation). The invading cells subsequently form sprouts with open lumen structures. With this system, all the sequential cellular mechanisms that occur during sprouting angiogenesis in vivo were observed and demonstrated. Endothelial cells maintained in cultured for several days form multicellular capillary-like structures. Endpoint F-actin and DAPI labeling shows the organization and the complexity of these structures. However, capillaries maintained under static conditions regress and lose their connection to the monolayer. One of the hallmarks of capillary formation is the development of lumen structures. To demonstrate the presence of open lumens, fluorescent microspheres were added to the channel on the apical surface of the monolayer.

The culture of endothelial cells populated in collagen gels have been previously studied in macro-scale systems[35] but not yet in a microscale device. Isolated cells cultured in a three-dimensional scaffold formed multi-cellular chords and endothelial cell rings. To demonstrate the effect of biochemical stimuli, three-dimensionally encapsulated endothelial cells were cultured in media supplemented with bFGF, VEGF and PMA. As expected, there was a dramatic difference in the morphology compared to control samples. In control sample, cells migrate and organize to form isolated multi-cellular ring-like structures. Cells stimulated with pro-angiogenic factors remodel to form complex interconnected multi-cellular capillary-like structures. In the presence of interstitial flow endothelial cells form multi-cellular structures within the gel and the monolayer at the gel/liquid interface.

Microvascular endothelial cells cultured in a microfluidic device experienced extensive morphogenesis. Endothelial cells on the fibronectin coated channel retain their characteristic cobblestone phenotype while a remarkable difference in morphology was evident at the gel surface. Prior to sheet or tube formation, the cells migrated as a contiguous structure into the gel region with a prominent increase in vacuoles and blebs. These structures were highly dynamic but eventually evolved into more stable sheets and tubes. Serial sections of fixed samples obtained from confocal imaging and subsequent 3D reconstruction of endothelial cell networks confirm the presence of circular and flattened lumen-like structures which extend throughout the length of the vessel. The existence of continuous lumens is further demonstrated by flowing beads through the vessels under a small pressure drop. Some can be observed flowing all the way across the gel cage and others collect at necked-down regions in the vascular structure.

Microvascular Endothelial Cells Sprouting Video. To demonstrate the capability to monitor cells in real-time, time-lapse video images were recorded of endothelial cells during sprouting angiogenesis. An endothelial monolayer was formed on collagen gel scaffold as described herein. The microfluidic device was kept in a custom built environmental control chamber at 37° C. and 5% $CO_2$ and cells visualized with a Zeiss inverted microscope. To minimize evaporation during the course of the experiment, media reservoirs (with zero height differentials) were connected directly at each inlet and outlet port. The device was then placed in a secondary container with a humidified local environment and cut-out glass window in the bottom for visualization. Bright-field images were taken with the AxioCam MRm (Carl Zeiss) (at single optical plane) at 2 minutes interval with AxioVision image acquisition software.

Cytoskeleton and Nuclei Staining. F-actin distribution and number of cells involved in "capillary-like" network or tube structures were assessed after 2-7 days culture in the device. F-actin and nuclei staining were performed after fixation with 4.0% PFA (30 minutes). The fixed samples were rinsed twice with 1× phosphate buffered saline (PBS), treated with 0.1% Triton-X (1-2 minutes), rinsed with 1×PBS followed by the infusion of a mixture of DAPI and rhodamine phalloidin (30 minutes) and a final wash step with 1×PBS.

Example 4

Study of Cell Migration in a Multiple Fluid-flow Path Device

PDMS microfluidic assay preparation. Microfluidic assay was made of PDMS (poly-dimethyl siloxane, Silgard 184, Dow Chemical, MI) by general soft lithography process with SU-8 patterned wafers. 4-inch silicon wafer was dehydrated on 200° C. hot plate for 5 minutes, and then coated by SU-8 2050 photoresist (MicroChem, MA). The coated wafer was soft baked on hot plate, exposed by UV aligner (EVGroup, AZ) and baked again. Patterns were developed by PM acetate and rinsed with iso-propyl alcohol. The wafer was then coated with tridecafluoro-1,1,2,2,-tetrahydrooctyl-1-trichlorosilane to make the cured PDMS easily detachable from the wafer. PDMS curing kit was mixed and poured on the wafer, which was then cured in the oven for 2 hours at 80° C. The cured PDMS was detached from the wafer, trimmed and punched to define inlets and outlets of microfluidic channels. Fabricated PDMS device and glass coverslip were autoclaved and dried in oven at 80° C. overnight. They were then plasma treated for 40 seconds by plasma cleaner (Harrick, Calif.) in air environment, and bonded together to form a closed microfluidic channel. The bonded device was kept in the oven of 80° C. for 10 minutes to enhance the bonding strength and then coating solution was filled in the channels to make the channel be suitable for cell seeding. The device was then aspirated and washed with sterile water. The coated device was then dried in the oven of 80° C. for 24 hours, to make the channel surface hydrophobic. Scaffold material was then filled in the gel region to form gel scaffold. In the experiments, type I collagen (BD Biosciences, MA) was filled by pipette and kept in incubator for 30 minutes. After gel polymerization, cell culture medium was filled into microfluidic channels and the device was kept in incubator for cell seeding.

Media exchange, dextran diffusion experiments and flow application. The filled media should be kept as droplets on inlets and outlets to avoid evaporation of the media. Aspirating an existing droplet and adding a new droplet of media on one side can generate micro flow due to capillary force to replace the old media in the channel with minimal shear stress on the cells. To apply mechanical angiogenic factors such as fluid shear stress or pressure gradient, fluidic circuits consisting of tubes and pumps can be connected to inlets and outlets of the device to apply precisely controlled flow. To visualize diffusion of biochemical factors from condition channel to cell channel, dextran with molecular weight of 40 kDa was mixed with endothelial growth media to a final concentration of 0.5 µg/mL and added to condition channel. The diffusion profile was taken by fluorescence microscope (Nikon Instruments, NY) and analyzed by Matlab to get the intensity graph from images. Time-lapse diffusion of fluorescent dextran into the collagen gel scaffold was measured. Stable and linear gradient was achieved and maintained for several hours. Images were obtained 10 hours after applying dextran mixed media into the condition channel. The molecular weight of dextran was 40 kDa, molecular weight on the order of VEGF. The collagen scaffold used had 2.0 mg/mL concentration polymerized at pH 7.4. Transient diffusion curves of dextran into collagen gel scaffold show dextran travels from one fluid-flow path through the scaffold into another fluid-flow path in 30 minutes.

Endothelial cell culture. The cell suspension media was prepared with $2\times10^6$ cells/mL and filled into the cell culturing channel. After filling, the device was kept in the incubator for 30 minutes for cells to settle down and attach on the substrate before the medium was replaced. The cell attachments duration ranges from 30 minutes to several hours depending on the cell types. Human dermal microvascular endothelial cells (HMVEC) were commercially obtained (Lonza, N.J.) and expanded with endothelial growth media (EGM-2MV; Lonza, N.J.) on regular culture flasks pre-coated with collagen I (BD Biosciences, MA) for no more than 9 passages. Recombinant human vascular endothelial growth factor (VEGF; R&D Systems, MN) was mixed with cell culturing media with working concentration of 20 ng/mL and then was filled into the condition channel to generate gradient.

Measuring and quantification of cell migration. The device was kept in incubator containing 5% $CO_2$ at 37° C. and cell migration was monitored by phase contrast microscopy (Nikon Instruments, NY) daily. The length and area of migrated cell outlines were measured by ImageJ. Immunofluorescence staining was performed to visualize the final cell migration result. Actin filaments and nuclei were stained with Rhodamine-Phalloidin (Sigma-Aldrich, Switzerland) and DAPI (Sigma-Aldrich, Switzerland), respectively.

Co-culture experiments. 1) MTLn3/U87MG and HMVEC co-culture; Rat mammary adenocarcinoma cell line (MTLn3) was grown in α-minimum essential medium (α-MEM; Invitrogen, CA) supplemented with 5% fetal bovine serum (FBS), 1 mM $Na(HCO_3)_2$, 4 mM L-glutamine, and penicillin/streptomycin. Human glioblastoma cell line (U87MG) was grown in Dulbecco's Modified Eagle Medium (DMEM) supplemented with 10% FBS, 1 mM $Na(HCO_3)_2$, 4 mM L-glutamin, and penicillin/streptomycin. The U87MG cell suspensions was prepared at the concentration of $1\times10^6$ cells/mL and filled into the condition channel. MTLn3 cell suspension for high density was at the concentration of $1\times10^6$ cells/mL and that for low was at the concentration of $0.5\times10^6$ cells/mL. HMVEC suspension was prepared at the concentration of $2\times10^6$ cells/mL as described above, and filled into cell culturing channel 1 day after MTLn3 or U87MG cell seeding. The cell culturing channel was filled with endothelial growth media and control/condition channels were filled with MTLn3 or U87MG growth media described above. Medium was changed everyday. Actin filaments and nuclei were stained with Rhodamine-Phalloidin and DAPI, respectively, and GFP-expressing MTLn3 and U87MG cells were used to distinguish from HMVEC. Smooth muscle cells (SMCs) were grown in HMVEC media described above and suspension was prepared at the concentration of $0.5\times10^6$ cells/mL. The suspension was filled into the condition channel in 1 day before HMVEC seeding into the cell channel. Medium was changed everyday. Actin filaments and nuclei were stained with Rhodamine-Phalloidin and DAPI. The same cell suspension described above was prepared and filled into the cell channel for chemotaxis evaluation of U87MG cells. The control channel was filled with the same media as cell channel and the condition channel was filled with the medium supplemented with 20 ng/mL or 200 ng/mL hEGF. hEGF gradient was applied one day after cell seeding and all media in the channel were changed everyday. Actin filaments and nuclei were stained with Rhodamine-Phalloidin and DAPI, respectively. All collagen gel scaffolds used in experiments were polymerized at pH 7.4 or 11.0, at the concentration of 2.0 mg/mL or 2.5 mg/mL.

A microfluidic bioreactor for studying cell migration was designed and fabricated to have the following advantages: 1) easy quantification and visual inspection in real time, 2) versatility of cell types and culture conditions and 3) precise control over biochemical and biomechanical stimuli. Cells are seeded and cultured in one microfluidic channel (cell channel), in direct contact with the scaffold made of ECM-like material. Cells in the cell channel migrate toward the opposing channel through the scaffold under the influence of biochemical and mechanical factors. Mechanical factors such as fluid shear stress and interstitial flow produced by a pressure gradient can be applied while biochemical cues can be introduced either spatially uniform or in a controlled gradient to study cell responses. The gel scaffold may also be functionalized to direct migration toward a gradient of immobilized ligands or functionalized ECMs. Lastly, a second cell type can be suspended within the gel region or cultured in an opposing channel to evaluate co-culture dependent cell migration and interactions.

The "cell channel" is located in the center with gel scaffolds on both sides so that cells can migrate to either side under precisely controlled conditions of mechanical and biochemical factors (e.g., fluid shear stress, interstitial flow, scaffold stiffness and fixed gradients of chemoattractants or growth factors (VEGF, S1P)). The three channel design has a unique feature that allows the control and condition experiments to be performed simultaneously on the same sample. One of the outside channels ("condition channel") contains the test agent while the other ("control channel") contains control medium. Cell migration toward the condition channel or the control channel can be directly compared, minimizing the chip-to-chip errors due to slight differences of cell activity, cell seeding density, media composition and other environmental conditions.

Characterizations of the biochemical diffusion and gradient generation were evaluated using fluorescence tagged dextran. Dextran of 40 kDa molecular weight was used to simulate growth factor diffusion. Dextran was applied to the condition channel and the resulting fluorescent intensity within the three-dimensional scaffold region was monitored as the dextran diffused into the cell channel. Initial diffusion of dextran to the central cell channel occurred within 30 minutes. Equilibrium was established after several hours and a linear concentration profile was maintained for 10 hours.

Quantified chemotaxis experiments with endothelial cells. To demonstrate the functionality of the microfluidic devices described herein in an assay of capillary morphogenesis, human dermal microvascular endothelial cells (HMVEC)

were seeded in the cell channel and a confluent monolayer was formed 1-2 days after cell seeding. Vascular Endothelial Growth Factor-A (VEGF), a known stimulant of endothelial cell migration[23,24] was applied to the condition channel, generating a VEGF gradient in gel scaffold between the cell channel and the condition channel. The control channel was filled with normal cell culture medium without VEGF as a control. Medium droplets (40 μL) were placed over the channel inlets and outlets to control the pressure difference along and between channels (i.e., to generate flow during media change and cell seeding or maintain no flow conditions throughout the course of the experiment), a technique previously shown by Walker et al.[25] to generate stable flow strong enough to replenish media and at the same time weak enough to avoid any damage to the scaffold or cells. Length and area changes of migrating cells into collagen scaffolds of different stiffness (pH 7.4 and pH 11) were observed and quantified over several days. On the condition side, cells rapidly migrated into the scaffold, while significantly less migration was observed on the control side.

As shown in FIGS. 20A-G, endothelial cells were stimulated to migrate into collagen scaffolds. FIG. 20A shows that one day after endothelial cell seeding a confluent monolayer was formed in the cell channel and growth factor (20 ng/mL of VEGF) was then applied in the condition channel. FIG. 20B shows migration results of microvascular cells in collagen gel scaffold polymerized at pH, 7.4 and (c) at pH 11.0. Cells were fixed after 6 days of culture with 5 days of VEGF gradient application, and stained by Rhodamine-Phalloidin and DAPI. White dotted lines indicate the outlines of gel scaffold and small rectangles in scaffold indicate the PDMS posts of 150 μm×150 μm. "0.2%" indicates a collagen concentration of 2.0 mg/mL. In both cases, it can be noticed that cells preferentially migrated into the gel on the condition side toward VEGF gradient. FIG. 20D is a graph of normalized relative length of migrated cells in the collagen gel scaffold polymerized at pH 7.4 with concentration of 2.0 mg/mL. 'No VEGF' serves as the negative control without VEGF gradient. VEGF was applied daily for various durations. 'VEGF at day 1' means that VEGF was first applied 1 day after cell seeding. VEGF at day 2 or 3 means VEGF was first applied 2 or 3 days after cell seeding. The relative length is calculated as the difference from the control side. FIG. 20E is a graph of normalized relative area of migrated cells in the collagen gel scaffold polymerized at pH 7.4 with concentration of 2.0 mg/mL. FIGS. 20F and G are graphs of normalized relative length and area of migrated cells in the collagen gel scaffold polymerized at pH 11.0 with concentration of 2.0 mg/mL. All graphs made by average of the value in 4 devices with n=8 (total 8 scaffolds) under one condition.

To evaluate the sensitivity of this assay, VEGF was applied to the condition channel 1, 2 or 3 days after cell seeding. Results are presented in two ways: the normalized values and the relative normalized values. For the normalized values, the measured data were normalized to their own baseline data at the initial time point (Eq. 1). Relative normalized values were assessed as the difference between the normalized data of the condition side and the control side. (Eq. 2).

$$[F_n] = \frac{F_n - F_0}{F_B} \quad (1)$$

$$[F_n]_{relative} = [F_n]_{at\ condition\ side} - [F_n]_{at\ control\ side} \quad (2)$$

where $F_0$ is value at the initial time point, $F_B$ basic value, $F_n$ value at time point n, and $[F_n]$ normalized value. F is either the length of the outer envelope of cells, L or the projected cell area, S. No statically significant differences could be observed with only normalized values. However, the relative normalized values yielded statically significant differences when comparing the length and area changes of cell migration for different durations of VEGF application. The relative normalized values of length and area change imply that, with collagen gel polymerized at pH 7.4, VEGF applied at 1 day and 2 days after cell seeding induced cell migration while VEGF added after 3 days did not. In collagen scaffolds polymerized at pH 11.0 (stiff gels), relative normalized values of the length change showed significant differences of cell migration at various time points. The relative normalized values of the area change were, however, too small to be detected in the collagen scaffolds polymerized at pH 11.0. Relative normalized values provide insights that were not apparent when studying normalized values alone. High sensitivity could be achieved by comparing the control experiment on the same device, eliminating chip-to-chip variability.

Induced angiogenesis by mechanical properties of collagen scaffold. The observed endothelial cell migration patterns demonstrated here depend on the collagen gel stiffness. Gel stiffness can be controlled by adjusting the pH of the collagen solution before polymerization with higher pH values resulting in stiffer gels[5]. Comparing initial gelling conditions of pH 7.4 and pH 11 gels revealed that stiffer collagen gels (polymerized at pH 11) restrict endothelial cell population migration, but promote the generation of tube-like structures with diameters in the range of 20-30 μm. Formed structures resembled tube-like capillaries observed in other in vivo assays or 3D macro assays.[9,18] and the existence of a lumen was subsequently confirmed by introducing 2-μm microbeads into the culture medium and tracking the microbead motion using fluorescence microscopy. For this confirmation, low interstitial flow was applied from the cell culturing channel to the condition channel by maintaining a pressure difference between them via droplet size control[25]. Time lapse particle tracking of microbeads was performed and beads flowed only within the tube-like structure being accumulated at the end of the capillary structure over time.

The role of gel stiffness on the structure of migrated endothelial cells can also be illustrated by the differences in the outlines of migrated cells. In softer scaffold the outline was wide reaching both ends of the scaffold, while outline in the stiffer scaffold showed very slender, tube-like structures. This observation implies the different modes of cell migration in scaffold with different mechanical properties and the possibility to control the structure of migrated cells and tube-like structures with different mechanical properties of the scaffold. It is also worth noting that mechanical properties of the scaffold influence the positions of the nuclei. In the softer scaffold, nuclei of migrated cells were located near the center of the cell.

In an attempt to quantitatively describe the different modes or structures of migrated cells, normalized area is plotted against normalized length. Defined are two new parameters, a (assumed length of migrated cell outline) and K (assumed sum of width of migrated cell outline), as shown in Equation 3. Under the assumptions, tube-like structures are characterized by experimental results with three boundaries, K=50, K=150 and $[S_n]$=8.

$$[L_n] = \frac{L_n - L_0}{L_B} \cong \frac{2a}{L_B} \quad (3)$$

-continued $$[S_n] = \frac{S_n - S_0}{S_B} \cong \frac{aK}{S_B}$$

$$\therefore [S_n] = \frac{L_B}{2S_B} K[L_n]$$

Various applications of the new microfluidic platform. A major advantage of this new design is its capability to study cell migration through 3D matrices and across endothelial layers. Cancer cell extravagation has previously been shown to depend on interactions with endothelial cells[26,27]. It is well established that cancer stromal cells signal to endothelial cells for angiogenesis. In cancer therapy, impeding angiogenesis is critical along with chemotherapy and other treatments[28]. To investigate these effects, the interaction of cancer cells and endothelial cells were studied by co-culturing the two cell types in a microfluidic device. A rat mammary adenocarcinoma cell line (MTLn3) or human neural cancer cells (U87MG) were cultured in the condition channel and HMVECs were cultured in the cell channel. In preliminary observations, high density MTLn3 attracted HMVEC into the collagen scaffold, but the migration rate was significantly slowed compared to that in VEGF gradient (20 ng/mL) induced HMVEC migration, suggesting that the chemotactic factors generated by MTLn3 cells are less stimulatory than the VEGF gradient. The extent of migration was positively correlated to the number of the MTLn3 cells in the conditioned channels. Low density MTLn3 cells did not induce significant migration of HMVECs. U87MG cells appeared not to attract HMVEC, in spite of high cell density in the condition channel and ability to migrate into the collagen scaffold. Compared to MTLn3 cells, U87MG cells were more active and readily migrated into the scaffolds.

The chemotactic effect of vascular smooth muscle cells (SMC) on endothelial cells was also demonstrated by seeding human aortic SMC in the condition channel and HMVEC in the cell channel. Monitoring HMVEC migration in the condition and the control gel region demonstrated the stabilizing capability of SMC to HMVEC. Migration of HMVEC was suppressed in condition side. The responses of SMC to HMVEC or HMVEC to SMC are now being investigated for further study. In the future, this co-culture strategy could be used to investigate the role of SMC recruitment to endothelial cells in stabilizing newly formed capillaries[29-32].

To investigate the migration speed and displacement of U87MG cells, HMVECs were cultured in the condition channel and a hEGF gradient was generated. At first, limited migration of U87MG cells was observed when HMVEC were plated in the condition channel, suggesting that HMVECs did not attract U87MG cells. When a gradient in hEGF was produced by adding 20 or 200 ng/mL hEGF in the condition channel, migration speed of U87MG cells of the condition side was higher than that of the control side and both were higher than the speed with HMVEC co-culture. This demonstrates that hEGF diffused across the matrix and reached the cells not only on the condition side but also to the control side and that the observed migration speed difference was perhaps due to chemokinesis as opposed to chemotaxis. Also observed was an effect of mechanical properties of the collagen scaffold on cell migration. In the higher concentration scaffolds (0.25% collagen), the migration speed of U87MG cells was suppressed requiring a longer time to show significant chemokinetic differences in migration speeds on the control and condition sides. These results demonstrate the ability of the microfluidic devices described herein to investigate the effect of the mechanical or chemical properties of ECM on cell migration. For cancer cells, it has previously been demonstrated that ECM stiffness is related to cancer cell activity[33].

By introducing cells at different time points, different densities and different seeding arrangements, it is foreseeable that a model system of cancer progression can be developed incorporating serial steps of angiogenesis, intravasation and extravasation[34]. In preliminary experiments developing a cancer intravasation assay, U87MG cells were cultured in the condition channel and HMVEC in the cell channel. Intravasation of U87MG cells, colored in green with GFP, into the HMVEC monolayer was observed. Several U87MG cells passed through the monolayer, and were subsequently either convected away by medium flow in the cell channel or remained attached and grew on the HMVEC monolayer. This evidence demonstrates the utility of this assay in studying and analyzing the migration of cancer cells into the luminal side of endothelial cell monolayer which was shown in vivo[35].

This microfluidic platform proves to be a versatile and powerful tool to study cell migration for various biological applications. It provides a well-controlled cell culture environment which can be observed in real time. Furthermore, it allows for an integration of biophysical and biochemical factors, essential in mimicking physiological conditions as cells constantly receive signals from both their soluble and insoluble environment. This device can be utilized as a model system for physiological and pathophysiological phenomena such as angiogenesis, arteriogenesis, cancer intravasation and cancer extravasation.

EQUIVALENTS

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

REFERENCES CITED

All publications and patents mentioned herein, including those references listed below, are hereby incorporated by reference in their entirety as if each individual publication or patent was specifically and individually incorporated by reference. In case of conflict, the present application, including any definitions herein, will control.

1. Gerhardt, H., Golding, M., Fruttiger, M., Ruhrberg, C., Lundkvist, A., Abramsson, A., Jeltsch, M., Mitchell, C., Alitalo, K., Shima, D. & Betsholtz, C., *J. Cell Biol.* 161, 1163-1177 (2003).
2. Helm, C-L. E., Fleury, M. E., Zisch, A. H., Boschetti, F. & Swartz, M. A., *Proc. Natl. Acad. Sci. U.S.A.* 102, 15779-15784 (2005).
3. Rutkowski, J. M. & Swartz, M. A., *Trends Cell Biol.*, 17, 44-50 (2007).
4. Sieminski, A. L., Hebbel, R. P. & Gooch, K. J., *Exp. Cell Res.*, 297, 574-584 (2004).
5. Yamamura, N., Sudo, R., Ikeda, M. & Tanishita, K., *Tissue Eng.*, 13, 1443-1453 (2007).

6. Jain, R. K., Schlenger, K., Hockel, M. & Yuan, F., *Nat. Med.*, 3, 1203-1208 (1997).
7. Nakayasu, K., Hayashi, N., Okisaka, S. & Sato, N., *Invest. Ophth. Vis. Sci.*, 33, 3050-3057 (1992).
8. Shiu, Y. T., Weiss, J. A., Hoying, J. B., Iwamoto, M. N., Joung, I. S. & Quam, C. T., *Crit. Rev. Biomed. Eng.* 33, 431-510 (2005).
9. Davis, G. E., Black, S. M. & Bayless, K. J., *In Vitro Cell. Dev. Biol.-An.*, 36, 513-519 (2000).
10. DiMilla, P. A., Quinn, J. A., Albeida, S. M. & Lauffenburger, D. A., *AIChe J.*, 38, 1092-1104, (1992).
11. Shizukuda, Y., Tang, S., Yokota, R. & Anthony Ware, J., *Circ. Res.*, 84, 247-256 (1999).
12. Rojas, J. D., Sennoune, S. R., Malti, D., Bakunts, K., Reuveni, M., Sanka, S. C., Martinez, G. M., Seftor, E. A., Meininger, C. J., Wu, G., Wesson, D. E., Hendrix, M. J. C. & Martinez-Zaguilan, R., *Am. J. Physiol. Heart Circ. Physiol.*, 291, H1147-H1157 (2006).
13. Sagnella, S. M., Kligman, F., Anderson, E. H., King, J. E., Murugesan, G., Marchant, R. E. & Kottke-Marchant, K., *Biomaterials*, 25, 1249-1259 (2004).
14. Hendrix, M. J. C., Seftor, E. A., Seftor, R. E. B. & Fidler, I. J., *Cancer Lett.*, 38, 137-147 (1987).
15. Mace, K. A., Hansen, S. L., Myers, C., Young, D. M. & Boudreau, N., *J. Cell Sci.*, 118, 2567-2577 (2005).
16. Bayless, K. J., Salazar, R. & Davis, G. E., *Am. J. Pathol.*, 156, 1673-1683 (2000).
17. Wenger, A., Stahl, A., Weber, H., Finkenzeller, G., Augustin, H. G., Stark, G. B. & Kneser, U., *Tissue Eng.*, 10, 1536-1547 (2004).
18. Ghajar, C. M., Blevins, K. S., Hughes, C. C. W., George, S. C. & Putnam, A. J., Tissue Eng., 12, 2875-2888 (2006).
19. Chicurel, M., *Science*, 295, 606-609 (2002).
20. Selmeczi, D., Mosier, S., Hagedom, P. H., Larsen, N. B. & Flyvbjerg, H., *Biophys. J.*, 89, 912-931 (2005).
21. Jeon, N. L., Baskaran, H., Dertinger, S. K. W., Whitesides, G. M., Van De Water, L. & Toner, M., *Nat. Biotechnol.*, 20, 826-830 (2002).
22. Lamalice, L., Le Boeuf, F. & Huot, J., *Circ. Res.*, 100, 782-794 (2007).
23. Yancopoulos, G. D., Davis, S., Gale, N. W., Rudge, J. S., Wiegand, S. J., J. Holash, *Nature*, 407, 242-248, 2000.
24. Coultas, L., Chawengsaksophak, K. & Rossant, J., *Nature*, 438, 937-945 (2005).
25. Walker, G. M. & Beebe, D. J., *Lab Chip*, 2, 131-134 (2002).
26. Carmeliet, P. & Jain, R. K., *Nature*, 407, 249-257 (2000).
27. Carmeliet, P., *Nature*, 438, 932-936 (2005).
28. Ferrara, N., Kerbel, R. S., *Nature*, 438, 967-974 (2005).
29. Montesano, R., Orci, L. & Vassalli, P., *J. Cell Biol.*, 97, 1648-1652 (1983).
30. Zhao, Y., Tan, Y. Z., Zhou, L. F., Wang, H. J., Mao, Y., *Stroke*, 38, 1313-1319 (2007).
31. Carmeliet, P., *Nat. Med.*, 6, 389-395 (2000).
32. Gerthoffer, G. T., *Circ. Res.*, 100, 607-621 (2007).
33. Huang, S., Ingber, D. E., *Cancer Cell.* 8, 175-176 (2005).
34. Suresh, S., *Acta Biomater.*, 3, 413-38 (2007).
35. Yamaguchi, H., Wyckoff, J. & Condeelis, J., *Curr. Opin. Cell Biol.*, 17, 559-564 (2005).
36. Cavallaro, U., Liebner, S. & Dejana, E., *Exp. Cell Res.*, 312, 659-667 (2006).
37. Vickerman, V., Blundo, J., Chung, S., Kamm, R. D. *Lab Chip*, 8(9), 1468-1477 (2008).
38. Chung, S., Sudo, R., Mack, P. J., Wan, C.-R., Vickerman, V., Kamm, R. D. *Lab Chip*, 9, 269-275 (2009).
39. Sudo, R., Chung, S, Zervantonakis, I. K., Vickerman, V., Toshimitsu, Y., Griffith, L. G., Kamm, R. D. *The FASEB Journal*, fj. 08-122820, published online Feb. 26, 2009.

We claim:

1. A microfluidic device, comprising:
an optically transparent material;
a substrate coupled to the optically transparent material; and
a scaffold having dimensions of at least 10 μm in three-dimensional space;
wherein
the substrate comprises a plurality of posts;
the scaffold contacts the substrate, the posts, and the optically transparent material;
the scaffold comprises a solid or semi-solid biological or biocompatible polymer;
the substrate comprises a first fluid-flow path and a second fluid-flow path;
the first fluid-flow path does not intersect with the second fluid-flow path;
the scaffold is disposed between the first fluid-flow path and the second fluid-flow path;
the posts are arranged in a staggered array; and
the staggered array of posts is disposed between the first fluid flow path and the second fluid flow path.

2. The device of claim 1, wherein the first fluid-flow path and the second fluid-flow path are channels in the substrate.

3. The device of claim 1, wherein the substrate comprises plastic.

4. The device of claim 1, wherein the substrate comprises PDMS.

5. The device of claim 1, wherein the substrate is modified.

6. The device of claim 5, wherein the modified substrate is a result of exposure of the substrate to poly-D-lysine, or exposure of the substrate to plasma.

7. The device of claim 1, wherein the scaffold comprises a first biological entity.

8. The device of claim 1, further comprising a pressure regulator.

9. The device of claim 1, wherein the first fluid-flow path or the second fluid-flow path comprises a resistance channel.

10. The device of claim 1, wherein the first fluid-flow path has different dimensions than the second fluid flow path.

11. The device of claim 1, wherein the scaffold comprises a solid or semi-solid biocompatible polymer; and the solid or semi-solid biocompatible polymer allows the passage of a second biological entity.

12. The device of claim 11, wherein the scaffold comprises collagen, agarose, gelatin, fibronectin, fibrin, laminin, or a peptide; and the second biological entity comprises a eukaryotic cell.

13. The device of claim 11, wherein the scaffold comprises collagen; and the second biological entity is selected from the group consisting of a growth factor, a cytokine, a hormone, an antibody, and an enzyme.

14. A method of measuring directed migration of a cell, comprising the steps of:
a) providing a device of claim 1;
b) introducing a cell into the first fluid-flow path;
c) introducing a biological entity into the second fluid-flow path; and
d) measuring the directed migration of the cell into the scaffold.

15. The method of claim 14, wherein the biological entity is selected from the group consisting of prokaryotic cells, eukaryotic cells, growth factors, cytokines, hormones, antibodies, drugs, and enzymes.

16. The method of claim 14, wherein the cell is a neutrophil, and the biological entity is an endothelial cell.

17. The method of claim 14, wherein the cell is an endothelial cell; the biological entity is a second cell; the second cell is a tumor cell.

18. The method of claim 17, wherein the cell and the second cell are obtained from the same subject.

19. A method of measuring blood vessel formation, comprising the steps of:
   a) providing a device of claim 1;
   b) introducing an endothelial cell or endothelial cell precursor into the first fluid-flow path;
   c) introducing a biological entity into the second fluid-flow path; and
   d) measuring the formation of a blood vessel in the scaffold.

20. The method of claim 19, wherein the biological entity is selected from the group consisting of prokaryotic cells, eukaryotic cells, growth factors, cytokines, hormones, antibodies, drugs, and enzymes.

21. A method of measuring permeability, comprising the steps of
   a) providing a device of claim 1;
   b) introducing a first substance into the first fluid-flow path; and
   c) measuring the permeability of the first substance into the scaffold.

22. The method of claim 21, wherein the first substance is a fluid or a small molecule.

23. The method of claim 21, wherein the scaffold comprises a cell monolayer.

24. The method of claim 21, wherein the first substance comprises a cell.

25. The method of claim 24, wherein the cell is an endothelial cell.

26. The method of claim 21, wherein the scaffold comprises a second cell.

27. The method of claim 26, wherein the second cell is a tumor cell.

* * * * *